(12) United States Patent
Settembre et al.

(10) Patent No.: US 9,744,228 B2
(45) Date of Patent: Aug. 29, 2017

(54) METHOD FOR GENERATING A PARVOVIRUS B19 VIRUS-LIKE PARTICLE

(75) Inventors: Ethan Settembre, Lexington, MA (US); Angelica Medina-Selby, San Francisco, CA (US); Doris Coit, Petaluma, CA (US); Philip R. Dormitzer, Weston, MA (US)

(73) Assignee: Norvartis AG, Basel (CH)

( * ) Notice: Subject to any disclaimer, the term of this patent is extended or adjusted under 35 U.S.C. 154(b) by 0 days.

(21) Appl. No.: 13/639,820

(22) PCT Filed: Apr. 7, 2011

(86) PCT No.: PCT/US2011/031630
§ 371 (c)(1),
(2), (4) Date: Feb. 19, 2013

(87) PCT Pub. No.: WO2011/127316
PCT Pub. Date: Oct. 13, 2011

(65) Prior Publication Data
US 2013/0273109 A1    Oct. 17, 2013

Related U.S. Application Data

(60) Provisional application No. 61/321,856, filed on Apr. 7, 2010.

(51) Int. Cl.
| | | |
|---|---|---|
| *A61K 39/00* | (2006.01) | |
| *A61K 39/23* | (2006.01) | |
| *C07K 14/005* | (2006.01) | |
| *C12N 7/00* | (2006.01) | |

(52) U.S. Cl.
CPC ............ *A61K 39/23* (2013.01); *C07K 14/005* (2013.01); *C12N 7/00* (2013.01); *A61K 2039/5258* (2013.01); *A61K 2039/53* (2013.01); *C12N 2750/14222* (2013.01); *C12N 2750/14223* (2013.01); *C12N 2750/14243* (2013.01); *C12N 2830/20* (2013.01); *C12N 2830/34* (2013.01)

(58) Field of Classification Search
CPC .......... C12N 15/86; C12N 2750/14143; C12N 2830/008; A61K 48/00
USPC ........................................................ 424/233
See application file for complete search history.

(56) References Cited

U.S. PATENT DOCUMENTS

| | | | | |
|---|---|---|---|---|
| 6,379,885 B1* | 4/2002 | Brown | ............................... | 435/5 |
| 6,743,772 B1* | 6/2004 | Broliden | .............. | A61K 38/162 424/204.1 |
| 2002/0119527 A1 | 8/2002 | Brown | | |
| 2008/0044438 A1* | 2/2008 | Ostroff | .................. | A61K 39/385 424/209.1 |

FOREIGN PATENT DOCUMENTS

| | | | |
|---|---|---|---|
| JP | 07147986 | 6/1995 | |
| WO | WO03002753 | 1/2003 | |
| WO | 2007084773 | 7/2007 | |
| WO | WO2008040717 | * | 4/2008 |

OTHER PUBLICATIONS

Shelly et al., "Parvovirus B19 VLP Vaccine Manufacturing", 2009, Genetic Engineering & Biotechnology News, 29(16): pdf pp. 1-3.*
O'Reilly, D.R., Miller, L.K., & Luckow, V.A. (1994). Baculovirus expression vectors: A laboratory manual. New York: Oxford University Press: pdf p. 50.*
Ahn et al. "The GC box and TATA transcription control elements in the P38 promoter o fthe minute virus of mice are necessary and sufficient for transactivation by the nonstructural protein NS1", 1992, 66(6):3776-3783.*
Brown et al., "Assembly of empty capsids by using baculovirus recombinants expressing human parvovirus B19 structural proteins", 1991, 65(5):2702-2706.*
Li et al. Construction and characterization of bidirectional expression vectors in *Saccharomyces cerevisiae*. FEMS Yeast Res. Feb. 2008;8(1):6-9. Epub Nov. 20, 2007.*
Kajigaya S et al., Self-assembled B19 parvovirus capsids, produced in a baculovirus system, are antigenically and immunogenically similar to native virions. Proc Natl Acad Sci U S A. 1991. 88(11):4646-50.
Ozawa K et al., Novel transcription map for the B19 (human) pathogenic parvovirus. J Virol. 1987. 61(8):2395-406.
Shelly D and Van Cleave V. Parvovirus B19 VLP vaccine manufacturing. Gen. Eng. Biotech. News. 29:1-3.
European Office Action dated Feb. 10, 2015 from corresponding European Application No. 11716449.1.
Ballou et al., "Safety and Immunogenicity of a Recombinant Parvovirus B19 Vaccine Forulated with MF59C.1," Journal of Infectious Diseases, 187:675-678 (2003).
Japanese Office Action dated Mar. 10, 2015 from corresponding Japanese Application No. 2013-503962.
Brown et al., "Assembly of Empty Capsids by Using Baculovirus Recombinants Expressing Human Parvovirus B19 Structural Proteins," Journal of Virology, 65:2702-2706 (1991).
Vicente, et al., "Large Scale Production and Purification of VLP-Based Vaccines," Journal of Invertebrate Pathology, 107 (2011) 542-548.
Handa, et al. "Requirement for Distal Upstream Sequences for Maximal Transcription in Vitro of Early Region IV of Adenovirus," Molecular and Cellular Biology, Apr. 1984, pp. 791-798, vol. 4, No. 4.

* cited by examiner

*Primary Examiner* — Michelle S Horning
(74) *Attorney, Agent, or Firm* — McDermott Will & Emery LLP

(57) ABSTRACT

The invention provides a process for generating parvovirus VP1/VP2 virus like particles (VLPs). The invention further provides methods for purification of the parvovirus VLPs and imm pCDC7
**used for co-expression of ParvoB19 VP1 and VP2 VLPs in *S.cerevisiae***

Figure 1:
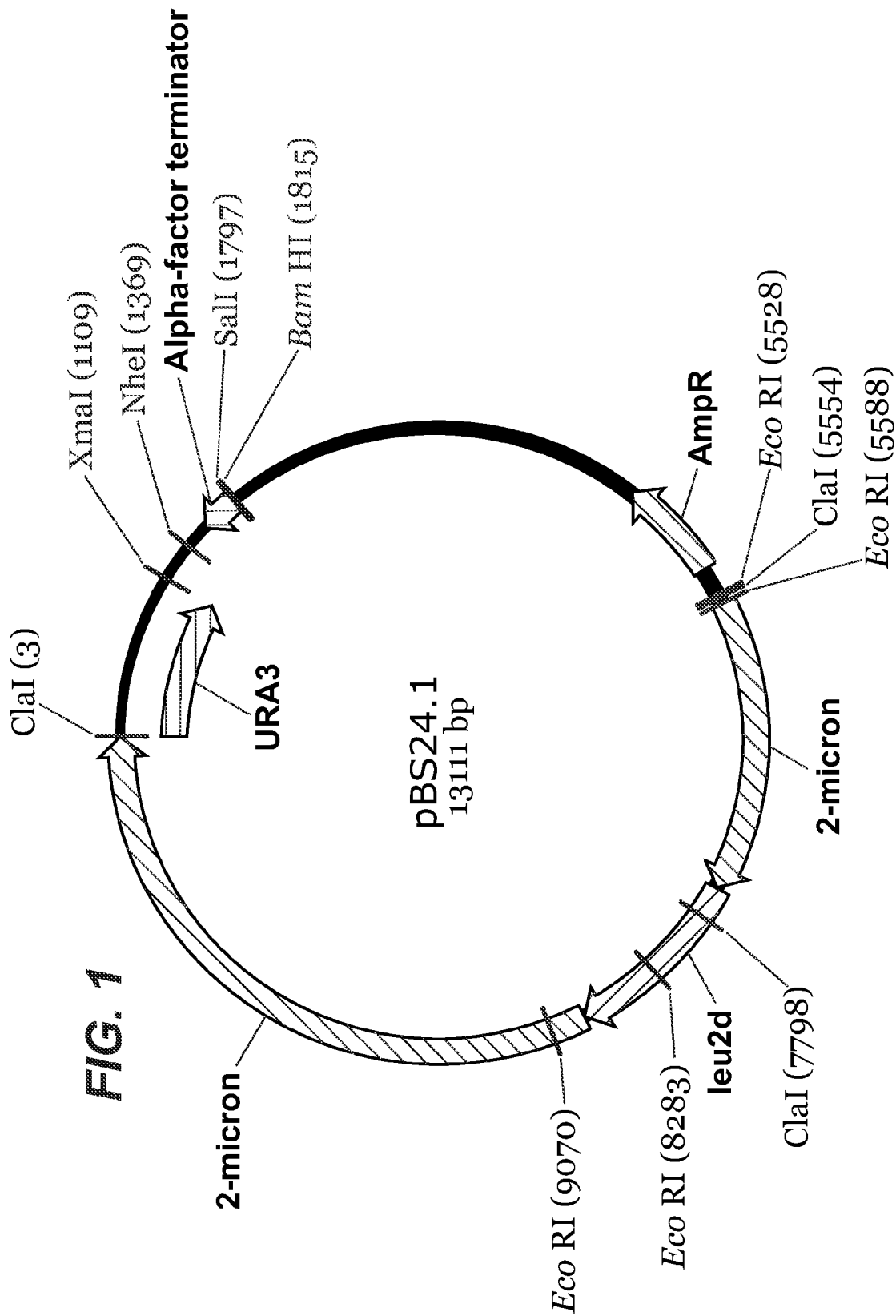

ATCGATAAGCTTTTCAATTCATCATTTTTTTTTATTCTTTTTTTTGATTTCGGTTTCCTTGAAATTTTTTTGAT
TCGGTAATCTCCGAACAGAAGGAAGAACGAAGGAAGGAGCACAGACTTAGATTGGTATATATACGCATATGTAGT
GTTGAAGAAACATGAAATTGCCCAGTATTCTTAACCCAACTGCACAGAACAAAAACCTGCAGGAAACGAAGATAA
ATCATGTCGAAAGCTACATATAAGGAACGTGCTGCTACTCATCCTAGTCCTGTTGCTGCCAAGCTATTTAATATC
ATGCACGAAAAGCAAACAAACTTGTGTGCTTCATTGGATGTTCGTACCACCAAGGAATTACTGGAGTTAGTTGAA
GCATTAGGTCCCAAAATTTGTTTACTAAAAACACATGTGGATATCTTGACTGATTTTCCATGGAGGGCACAGTT
AAGCCGCTAAAGGCATTATCCGCCAAGTACAATTTTTACTCTTCGAAGACAGAAATTTGCTGACATTGGTAAT
ACAGTCAAATTGCAGTACTCTGCGGGTGTATACAGAATAGCAGAATGGGCAGACATTACGAATGCACACGGTGTG
GTGGGCCCAGGTATTGTTAGCGGTTTGAAGCAGGCGGCAGAAGAAGTAACAAAGGAACCTAGAGGCCTTTTGATG
TTAGCAGAATTGTCATGCAAGGGCTCCCTATCTACTGGAGAATATACTAAGGGTACTGTTGACATTGCGAAGAGC
GACAAAGATTTGTTATCGGCTTTATTGCTCAAAGAGACATGGGTGGAAGAGATGAAGGTTACGATTGGTTGATT
ATGACACCCGGTGTGGGTTTAGATGACAAGGGAGCGCATTGGGTCAACAGTATAGAACCGTGGATGATGTGGTC
TCTACAGGATCTGACATTATTATTGTTGGAAGAGGACTATTTGCAAAGGGAAGGGATGCTAAGGTAGAGGGTGAA
CGTTACAGAAAAGCAGGCTGGGAAGCATATTTGAGAAGATGCGGCCAGCAAAACTAAAAAACTGTATTATAAGTA
AATGCATGTATACTAAACTCACAAATTAGAGCTTCAATTTAATTATATCAGTTATTACCCGGG

TTCAATATGCGCACATACGCTGTTATGTTCAAGGTCCCTTCGTTTAAGAACGAA
   AGCGGTCTTCCTTTTGAGGGATGTTTCAAGTTGTTCAAATCTATCAAATTTGCAAATCCC
   CAGTCTGTATCTAGAGCGTTGAATCGGTGATGCGATTTGTTAATTAAATTGATGGTGTCA
   CCATTACCAGGTCTAGATATACCAATGGCAAACTGAGCACAACAATACCAGTCCGGATCA
   ACTGGCACCATCTCTCCCGTAGTCTCATCTAATTTTTCTTCCGGATGAGGTTCCAGATAT
   ACCGCAACACCTTTATTATGGTTTCCCTGAGGGAATAATAGAATGTCCCATTCGAAATCA
   CCAATTCTAAACCTGGGCGAATTGTATTTCGGGTTTGTTAACTCGTTCCAGTCAGGAATG
   TTCCACGTGAAGCTATCTTCCAGCAAAGTCTCCACTTCTTCATCAAATTGtGGAGAATAC
   TCCCAATGCTCTTATCTATGGGACTTCCGGGAAACACAGTACCGATACTTCCCAATTCGT
   CTTCAGAGCTCATTGTTTGTTTGAAGAGACTAATCAAAGAATCGTTTTCTCAAAAAAATT
   AATATCTTAACTGATAGTTTGATCAAAGGGGCAAAACGTAGGGCAAACAAACGGAAAAA
   TCGTTTCTCAAATTTTCTGATGCCAAGAACTCTAACCAGTCTTATCTAAAAATTGCCTTA
   TGATCCGTCTCTCCGGTTACAGCCTGTGTAACTGATTAATCCTGCCTTTCTAATCACCAT
   TCTAATGTTTTAATTAAGGGATTTTGTCTTCATTAACGGCTTTCGCTCATAAAAATGTTA
   TGACGTTTTGCCCGCAGGCGGGAAACCATCCACTTCACGAGACTGATCTCCTCTGCCGGA
   ACACCGGGCATCTCCAACTTATAAGTTGGAGAAATAAGAGAATTTCAGATTGAGAGAATG
   AAAAAAAAAACC

CTTAGTTCATAGGTCCATTCTCTTAGCGCAACTACAGAGAACAGGGGCACAAACAGG
CAAAAAACGGGCACAACCTCAATGGAGTGATGCAACCTGCCTGGAGTAAATGATGACACAA
GGCAATTGACCCACGCATGTATCTATCTCATTTTCTTACACCTTCTATTACCTTCTGCTCT
CTCTGATTTGGAAAAAGCTGAAAAAAAGGTTGAAACCAGTTCCCTGAAATTATTCCCCTAC
TTGACTAATAAGTATATAAAGACGGTAGGTATTGATTGTAATTCTGTAAATCTATTTCTTAAA
CTTCTTAAATTCTACTTTTATAGTTAGTCTTTTTTTTAGTTTTAAAACACCAAGAACTTAG
TTTCGAATAAACACACATAAACAAAC cctaggacttctaagcggccgc

TTTGTTCCCACTGTACTTTTAGCTCGTACAAAATACAATATACTTTTCATTTCT

CCGTAAACAACATGTTTTCCCATGTAATATCCTTTTCTATTTTTCGTTCCGTTACCAACT

TTACACATACTTTATATAGCTATTCACTTCTATACACTAAAAAACTAAGACAATTTTAAT

TTTGCTGCCTGCCATATTTCAATTTGTTATAAATTCCTATAATTTATCCTATTAGTAGCT

AAAAAAGATGAATGTGAATCGAATCCTAAGA

FIG. 3A

```
GCTAGCGCTATATGCGTTGATGCAATTTCTATGCGCACCCGTTCTCGGAGCACTGTCC
GACCGCTTTGGCCGCCGCCCAGTCCTGCTCGCTTCGCTACTTGGAGCCACTATCGACTACGCGATCATGGCGACC
ACACCCGTCCTGTGGATCAGATCCAATTCTCTTAGGATTCGATTCACATTCATCTTTTTTTAGCTACTAATAGGA
TAAATTATAGGAATTTATAACAAATTGAAATATGGCAGGCAGCAAAATTAAAATTGTCTTAGTTTTTTAGTGTAT
AGAAGTGAATAGCTATATAAAGTATGTGTAAAGTTGGTAACGGAACGAAAAATAGAAAAGGATATTACATGGGAA
AACATGTTGTTTACGGAGAAATGAAAAGTATATTGTATTTTGTACGAGCTAAAAGTACAGTGGGAACAAA

GTCGACTTTCACAGGCAACGCGTGTTTGTTTATGTGTGTTTATTCGAAACTAAGTTCTTG
GTGTTTTAAAACTAAAAAAAAGACTAACTATAAAAGTAGAATTTAAGAAGTTTAAGAAAT
AGATTTACAGAATTACAATCAATACCTACCGTCTTTATATACTTATTAGTCAAGTAGGGG
AATAATTTCAGGGAACTGGTTTCAACCTTTTTTTTCAGCTTTTTCCAAATCAGAGAGAGC
AGAAGGTAATAGAAGGTGTAAGAAAATGAGATAGATACATGCGTGGGTCAATTGCCTTGT
GTCATCATTTACTCCAGGCAGGTTGCATCACTCCATTGAGGTTGTGCCCGTTTTTGCCT
GTTTGTGCCCCTGTTCTCTGTAGTTGCGCTAAGAGAATGGACCTATGAACTAAGGGTTTT
TTTTTTTCATTCTCTCAATCTGAAATTCTCTTATTTCTCCAACTTATAAGTTGGAGATGC
CCGGTGTTCCGGCAGAGGAGATCAGTCTCGTGAAGTGGATGGTTTCCCGCCTGCGGGCAA
AACGTCATAACATTTTTATGAGCGAAAGCCGTTAATGAAGACAAAATCCCTTAATTAAAA
CATTAGAATGGTGATTAGAAAGGCAGGATTAATCAGTTACACAGGCTGTAACGGAGAGA
CGGATCATAAGGCAATTTTTAGATAAGACTGGTTAGAGTTCTTGGCATCAGAAAATTTGA
GAAACGATTTTTCCGTTTGTTTGCCCCTACGTTTTGCCCCTTTGATCAAACTATCAGTTA
AGATATTAATTTTTTTGAGAAAACGATTCTTTGATTAGTCTCTTCAAACAAACAATGAGC
TCTGAAGACGAATTGGGAAGTATCGGTACTGTGTTTCCCGGAAGTCCCATAGATAAGAGC
ATTGGGAGTATTCTCCCACAATTTGATGAAGAAGTGGAGACTTTGCTGGAAGATAGCTTC
ACGTGGAACATTCCTGACTGGAACGAGTTAACAAACCCGAAATACAATTCGCCCAGGTTT
AGAATTGGTGATTTCGAATGGGACATTCTATTATTCCCTCAGGGAAACCATAATAAGGT
GTTGCGGTATATCTGGAACCTCATCCGGAAGAAAAATTAGATGAGACTACGGGAGAGATG
GTGCCAGTTGATCCGGACTGGTATTGTTGTGCTCAGTTTGCCATTGGTATATCTAGACCT
GGTAATGGTGACACCATCAATTTAATTAACAAATCGCATCACCGATTCAACGCTCTAGAT
ACAGACTGGGGATTTGCAAATTTGATAGATTTGAACAACTTGAAACATCCCTCAAAAGGA
AGACCGCTTTCGTTCTTAAACGAAGGGACCTTGAACATAACAGCGTATGTGCGCATATTG
AA
GGATCCTCGACCGAT
GCCCTTGAGAGCCTTCAACCCAGTCAGCTCCTTCCGGTGGGCGCGGGGCATGACTATCGTCGCCGCACTTATGAC
TGTCTTCTTTATCATGCAACTCGTAGGACAGGTGCCGGCAGCGCTCTGGGTCATTTCGGCGAGGACCGCTTTCG
CTGGAGCGCGACGATGATCGGCCTGTCGCTTGCGGTATTCGGAATCTTGCACGCCCTCGCTCAAGCCTTCGTCAC
TGGTCCCGCCACCAAACGTTTCGGCGAGAAGCAGGCCATTATCGCCGGCATGGCGGCCGACGCGCTGGGCTACGT
CTTGCTGGCGTTCGCGACGCGAGGCTGGATGGCCTTCCCCATTATGATTCTTCTCGCTTCCGGCGGCATCGGGAT
GCCCGCGTTGCAGGCCATGCTGTCCAGGCAGGTAGATGACGACCATCAGGGACAGCTTCAAGGATCGCTCGCGGC
TCTTACCAGCCTAACTTCGATCATTGGACCGCTGATCGTCACGGCGATTTATGCCGCCTCGGCGAGCACATGGAA
CGGGTTGGCATGGATTGTAGGCGCCGCCCTATACCTTGTCTGCCTCCCCGCGTTGCGTCGCGGTGCATGGAGCCG
GGCCACCTCGACCTGAATGGAAGCCGGCGGCACCTCGCTAACGGATTCACCACTCCAAGAATTGGAGCCAATCAA
TTCTTGCGGAGAACTGTGAATGCGCAAACCAACCCTTGGCAGAACATATCCATCGGTCCGCCATCTCCAGCAGC
CGCACGCGGCGCATCTCGGGCAGCGTTGGGTCCTGGCCACGGGTGCGCATGATCGTGCTCCTGTCGTTGAGGACC
CGGCTAGGCTGGCGGGGTTGCCTTACTGGTTAGCAGAATGAATCACCGATACGCGAGCGAACGTGAAGCGACTGC
TGCTGCAAAACGTCTGCGACCTGAGCAACAACATGAATGGTCTTCGGTTTCCGTGTTTCGTAAAGTCTGGAAACG
CGGAAGTCAGCGCCCTGCACCATTATGTTCCGGATCTGCATCGCAGGATGCTGCTGGCTACCCTGTGGAACACCT
ACATCTGTATTAACGAAGCGCTGGCATTGACCCTGAGTGATTTTCTCTGGTCCCGCCGCATCCATACCGCCAGT
TGTTTACCCTCACAACGTTCCAGTAACCGGGCATGTTCATCATCAGTAACCCGTATCGTGAGCATCCTCTCTCGT
TTCATCGGTATCATTACCCCCATGAACAGAAATCCCCCTTACACGGAGGCATCAGTGACCAAACAGGAAAAAACC
GCCCTTAACATGGCCCGCTTTATCAGAAGCCAGACATTAACGCTTCTGGAGAAACTCAACGAGCTGGACGCGGAT
GAACAGGCAGACATCTGTGAATCGCTTCACGACCACGCTGATGAGCTTTACCGCAGCTGCCTCGCGCGTTTCGGT
GATGACGGTGAAAACCTCTGACACATGCAGCTCCCGGAGACGGTCACAGCTTGTCTGTAAGCGGATGCCGGGAGC
AGACAAGCCCGTCAGGGCGCGTCAGCGGGTGTTGGCGGGTGTCGGGGCGCAGCCATGACCCAGTCACGTAGCGAT
AGCGGAGTGTATACTGGCTTAACTATGCGGCATCAGAGCAGATTGTACTGAGAGTGCACCATATGCGGTGTGAAA
TACCGCACAGATGCGTAAGGAGAAAATACCGCATCAGGCGCTCTTCCGCTTCCTCGCTCACTGACTCGCTGCGCT
CGGTCGTTCGGCTGCGGCGAGCGGTATCAGCTCACTCAAAGGCGGTAATACGGTTATCCACAGAATCAGGGGATA
ACGCAGGAAAGAACATGTGAGCAAAAGGCCAGCAAAAGGCCAGGAACCGTAAAAAGGCCGCGTTGCTGGCGTTTT
TCCATAGGCTCCGCCCCCTGACGAGCATCACAAAAATCGACGCTCAAGTCAGAGGTGGCGAAACCCGACAGGAC
TATAAAGATACCAGGCGTTTCCCCCTGGAAGCTCCCTCGTGCGCTCTCCTGTTCCGACCCTGCCGCTTACCGGAT
ACCTGTCCGCCTTTCTCCCTTCGGGAAGCGTGGCGCTTTCTCATAGCTCACGCTGTAGGTATCTCAGTTCGGTGT
AGGTCGTTCGCTCCAAGCTGGGCTGTGTGCACGAACCCCCCGTTCAGCCCGACCGCTGCGCCTTATCCGGTAACT
ATCGTCTTGAGTCCAACCCGGTAAGACACGACTTATCGCCACTGGCAGCAGCCACTGGTAACAGGATTAGCAGAG
```

FIG. 3B

```
CGAGGTATGTAGGCGGTGCTACAGAGTTCTTGAAGTGGTGGCCTAACTACGGCTACACTAGAAGGACAGTATTTG
GTATCTGCGCTCTGCTGAAGCCAGTTACCTTCGGAAAAAGAGTTGGTAGCTCTTGATCCGGCAAACAAACCACCG
CTGGTAGCGGTGGTTTTTTTGTTTGCAAGCAGCAGATTACGCGCAGAAAAAAAGGATCTCAAGAAGATCCTTTGA
TCTTTTCTACGGGGTCTGACGCTCAGTGGAACGAAAACTCACGTTAAGGGATTTTGGTCATGAGATTATCAAAAA
GGATCTTCACCTAGATCCTTTTAAATTAAAAATGAAGTTTTAAATCAATCTAAAGTATATATGAGTAAACTTGGT
CTGACAGTTACCAATGCTTAATCAGTGAGGCACCTATCTCAGCGATCTGTCTATTTCGTTCATCCATAGTTGCCT
GACTCCCCGTCGTGTAGATAACTACGATACGGGAGGGCTTACCATCTGGCCCCAGTGCTGCAATGATACCGCGAG
ACCCACGCTCACCGGCTCCAGATTTATCAGCAATAAACCAGCCAGCCGGAAGGGCCGAGCGCAGAAGTGGTCCTG
CAACTTTATCCGCCTCCATCCAGTCTATTAATTGTTGCCGGGAAGCTAGAGTAAGTAGTTCGCCAGTTAATAGTT
TGCGCAACGTTGTTGCCATTGCTGCAGGCATCGTGGTGTCACGCTCGTCGTTTGGTATGGCTTCATTCAGCTCCG
GTTCCCAACGATCAAGGCGAGTTACATGATCCCCCATGTTGTGCAAAAAAGCGGTTAGCTCCTTCGGTCCTCCGA
TCGTTGTCAGAAGTAAGTTGGCCGCAGTGTTATCACTCATGGTTATGGCAGCACTGCATAATTCTCTTACTGTCA
TGCCATCCGTAAGATGCTTTTCTGTGACTGGTGAGTACTCAACCAAGTCATTCTGAGAATAGTGTATGCGGCGAC
CGAGTTGCTCTTGCCCGGCGTCAACACGGGATAATACCGCGCCACATAGCAGAACTTTAAAAGTGCTCATCATTG
GAAAACGTTCTTCGGGGCGAAAACTCTCAAGGATCTTACGCTGTTGAGATCCAGTTCGATGTAACCCACTCGTG
CACCCAACTGATCTTCAGCATCTTTTACTTTCACCAGCGTTTCTGGGTGAGCAAAAACAGGAAGGCAAAATGCCG
CAAAAAAGGGAATAAGGGCGACACGGAAATGTTGAATACTCATACTCTTCCTTTTTCAATATTATTGAAGCATTT
ATCAGGGTTATTGTCTCATGAGCGGATACATATTTGAATGTATTTAGAAAAATAAACAAATAGGGGTTCCGCGCA
CATTTCCCCGAAAAGTGCCACCTGACGTCTAAGAAACCATTATTATCATGACATTAACCTATAAAAATAGGCGTA
TCACGAGGCCCTTTCGTCTTCAAGAATTCTCATGTTTGACAGCTTATCATCGATCCACTTGTATATTTGGATGAA
TTTTTGAGGAATTCTGAACCAGTCCTAAAACGAGTAAATAGGACCGGCAATTCTTCAAGCAATAAACAGGAATAC
CAATTATTAAAAGATAACTTAGTCAGATCGTACAATAAAGCTTTGAAGAAAAATGCGCCTTATTCAATCTTTGCT
ATAAAAAATGGCCCAAAATCTCACATTGGAAGACATTTGATGACCTCATTTCTTTCAATGAAGGGCCTAACGGAG
TTGACTAATGTTGGGAAATTGGAGCGATAAGCGTGCTTCTGCCGTGGCCAGGACAACGTATACTCATCAGATA
ACAGCAATACCTGATCACTACTTCGCACTAGTTTCTCGGTACTATGCATATGATCCAATATCAAAGGAAATGATA
GCATTGAAGGATGAGACTAATCCAATTGAGGAGTGGCAGCATATAGAACAGCTAAAGGGTAGTGCTGAAGGAAGC
ATACGATACCCCGCATGGAATGGGATAATATCACAGGAGGTACTAGACTACCTTTCATCCTACATAAATAGACGC
ATATAAGTACGCATTTAAGCATAAACACGCACTATGCCGTTCTTCTCATGTATATATATATACAGGCAACACGCA
GATATAGGTGCGACGTGAACAGTGAGCTGTATGTGCGCAGCTCGCGTTGCATTTTCGGAAGCGCTCGTTTTCGGA
AACGCTTTGAAGTTCCTATTCCGAAGTTCCTATTCTCTAGAAAGTATAGGAACTTCAGAGCGCTTTTGAAAACCA
AAAGCGCTCTGAAGACGCACTTTCAAAAAACCAAAAACGCACCGGACTGTAACGAGCTACTAAAATATTGCGAAT
ACCGCTTCCACAAACATTGCTCAAAAGTATCTCTTTGCTATATATCTCTGTGCTATATCCCTATATAACCTACCC
ATCCACCTTTCGCTCCTTGAACTTGCATCTAAACTCGACCTCTACATTTTTTATGTTTATCTCTAGTATTACTCT
TTAGACAAAAAAATTGTAGTAAGAACTATTCATAGAGTGAATCGAAAACAATACGAAAATGTAAACATTTCCTAT
ACGTAGTATATAGAGACAAAATAGAAGAAACCGTTCATAATTTTCTGACCAATGAAGAATCATCAACGCTATCAC
TTTCTGTTCACAAAGTATGCGCAATCCACATCGGTATAGAATATAATCGGGGATGCCTTTATCTTGAAAAAATGC
ACCCGCAGCTTCGCTAGTAATCAGTAAACGCGGGAAGTGGAGTCAGGCTTTTTTTATGGAAGAGAAAATAGACAC
CAAAGTAGCCTTCTTCTAACCTTAACGGACCTACAGTGCAAAAAGTTATCAAGAGACTGCATTATAGAGCGCACA
AAGGAGAAAAAAGTAATCTAAGATGCTTTGTTAGAAAAATAGCGCTCTCGGGATGCATTTTGTAGAACAAAAA
AGAAGTATAGATTCTTTGTTGGTAAAATAGCGCTC
TCGCGTTGCATTTCTGTTCTGTAAAAATGCAGCTCAGATTCTTTGTTTGAAAAATTAGCGCTCTCGCGTT
GCATTTTGTTTTACAAAAATGAAGCACAGATTCTTCGTTGGTAAAATAGCGCTT
TCGCGTTGCATTTCTGTTCTGTAAAAATGCAGCTCAGATT
CTTTGTTTGAAAAATTAGCGCTCTCGCGTTGCATTTTTGTTCTACAAAATGAAGCACAGATGCTTCGTTAACAAA
GATATGCTATTGAAGTGCAAGATGGAAACGCAGAAAATGAACCGGGGATGCGACGTGCAAGATTACCTATGCAAT
AGATGCAATAGTTTCTCCAGGAACCGAAATACATACATTGTCTTCCGTAAAGCGCTAGACTATATATTATTATAC
AGGTTCAAATATACTATCTGTTTCAGGGAAAACTCCCAGGTTCGGATGTTCAAAATTCAATGATGGGTAACAAG
TACGATCGTAAATCTGTAAAACAGTTTGTCGGATATTAGGCTGTATCTCCTCAAAGCGTATTCGAATATCATTGA
GAAGCTGCATTTTTTTTTTTTTTTTTTTTTTTTTTATATATATTTCAAGGATATACCATTGTAATGTCTG
CCCCTAAGAAGATCGTCGTTTTGCCAGGTGACCACGTTGGTCAAGAAATCACAGCCGAAGCCATTAAGGTTCTTA
AAGCTATTTCTGATGTTCGTTCCAATGTCAAGTTCGATTTCGAAAATCATTTAATTGGTGGTGCTGCTATCGATG
CTACAGGTGTTCCACTTCCAGATGAGGCGCTGGAAGCCTCCAAGAAGGCTGATGCCGTTTTGTTAGGTGCTGTGG
GTGGTCCTAAATGGGGTACCGGTAGTGTTAGACCTGAACAAGGTTTACTAAAAATCCGTAAAGAACTTCAATTGT
ACGCCAACTTAAGACCATGTAACTTTGCATCCGACTCTCTTTTAGACTTATCTCCAATCAAGCCACAATTTGCT
AAAGGTACTGACTTCGTTGTTGTTAGAGAATTAGTGGGAGGTATTTACTTTGGTAAGAGAAAGGAAGACGATGGT
GATGGTGTCGCTTGGGATAGTGAACAATACACCGTTCCAGAAGTGCAAAGAATCACAAGAATGGCCGCTTTCATG
GCCCTACAACATGAGCCACCATTGCCTATTTGGTCCTTGGATAAAGCTAATGTTTTGGCCTCTTCAAGATTATGG
AGAAAAACTGTGGAGGAAACCATCAAGAACGAATTCCCTACATTGAAAGTTCAACATCAATTGATTGATTCTGCC
GCCATGATCCTAGTTAAGAACCCAACCCACCTAAATGGTATTATAATCACCAGCAACATGTTTGGTGATATCATC
TCCGATGAAGCCTCCGTTATCCCAGGCTCCTTGGGTTTGTTGCCATCTGCGTCCTTGGCCTCTTTGCCAGACAAG
AACACCGCATTTGGTTTGTACGAACCATGCCATGGTTCCGCTCCAGATTTGCCAAAGAATAAGGTCAACCCTATC
GCCACTATCTTGTCTGCTGCAATGATGTTGAAATTGTCATTGAACTTGCCTGAAGAAGGTAAAGCCATTGAAGAT
GCAGTTAAAAAGGTTTTGGATGCAGGTATCAGAACTGGTGATTTAGGTGGTTCCAACAGTACCACCGAAGTCGGT
```

*FIG. 3C*

```
GATGCTGTCGCCGAAGAAGTTAAGAAAATCCTTGCTTAAAAAGATTCTCTTTTTTTATGATATTTGTACCAAAAA
AAAAAAAAAAAAAAAAAAAAAAAAAAAAAAAAAAAAAAAAAAAAAAAATGCAGCGTCACATCGGATAATAATGAT
GGCAGCCATTGTAGAAGTGCCTTTTGCATTTCTAGTCTCTTTCTCGGTCTAGCTAGTTTTACTACATCGCGAAGA
TAGAATCTTAGATCACACTGCCTTTGCTGAGCTGGATCAATAGAGTAACAAAAGAGTGGTAAGGCCTCGTTAAAG
GACAAGGACCTGAGCGGAAGTGTATCGTACAGTAGACGGAGTATACTAGTATAGTCTATAGTCCGTGGAATTCTA
AGTGCCAGCTTTATAATGTCATTCTCCTTACTACAGACCCGCCTGAAAGTAGACACATCATCATCAGTAAGCTTT
GACAAAAAGCATTGAGTAGCTAACTCTTCTATGCAATCTATAGCTGTTTTATAAGGCATTCAATGGACAGATTGA
GGTTTTTGAAACATACTAGTGAAATTAGCCTTAATCCCTTCTCGAAGTTAATCATGCATTATGGTGTAAAAAATG
CAACTCGCGTTGCTCTACTTTTTCCCGAATTTCCAAATACGCAGCTGGGGTGATTGCTCGATTTCGTAACGAAAG
TTTTGTTTATAAAAACCGCGAAAACCTTCTGTAACAGATAGATTTTTACAGCGCTGATATACAATGACATCAGCT
GTAATGGAAAATAACTGAAATATGAATGGCGAGAGACTGCTTGCTTGTATTAAGCAATGTATTATGCAGCACTTC
CAACCTATGGTGTACGATGAAAGTAGGTGTGTAATCGAGACGACAAGGGGGACTTTTCCAGTTCCTGACAATTAT
AAGAAATACAAAACGTTAGCATTTGCATTTGTTGGACATGTACTGAATACAGACGACACACCGGTAATTGAAAAA
GAACTGGATTGGCCTGATCCTGCACTAGTGTACAATACAATTGTCGATCGAATCATAAATCACCCAGAATTATCA
CAGTTTATATCGGTTGCATTTATTAGTCAGTTAAAGGCCACCATCGGAGAGGGTTTAGATATTAATGTAAAAGGC
ACGCTAAACCGCAGGGGAAAGGGTATCAGAAGGCCTAAAGGCGTATTTTTAGATACATGGAATCTCCATTTGTC
AATACAAAGGTCACTGCATTCTTCTCTTATCTTCGAGATTATAATAAAATTGCCTCAGAATATCACAATAATACT
AAATTCATTCTCACGTTTTCATGTCAAGCATATTGGGCATCTGGCCCAAACTTCTCCGCCTTGAAGAATGTTATT
AGGTGCTCCATAATTCATGAATACATTTCTAAGTTTGTGGAAAGAGAACAGGATAAAGGTCATATAGGAGATC
AGGAGCTACCGCCTGAAGAGGACCCTTCTCGTGAACTAAACAATGTACAACATGAAGTCAATAGTTTAACGGAAC
AAGATGCGGAGGCGGATGAAGGATTGTGGGGTGAAATAGATTCATTATGTGAAAAATGGCAGTCTGAAGCGGAAG
ATCAAACTGAGGCGGAGATAATAGCCGACAGGATAATTGGAAATAGCCAGAGGATGGCGAACCTCAAAATTCGTC
GTACAAAGTTCAAAAGTGTCTTGTATCATATACTAAAGGAACTAATTCAATCTCAGGGAACCGTAAAGGTTTATC
GCGGTAGTAGTTTTTCACACGATTCGATAAGATAAGCTTACATTATGAAGAGCAGCATATTACAGCCGTATGGG
TCTACTTGACAGTAAAATTTGAAGAGCATTGGAAGCCTGTTGATGTAGAGGTCGAGTTTAGATGCAAGTTCAAGG
AGCGAAAGGTGGATGGGTAGGTTATATAGGGATATAGCACAGAGATATATAGCAAAGAGATACTTTTGAGCAATG
TTTGTGGAAGCGGTATTCGCAATATTTTAGTAGCTCGTTACAGTCCGGTGCGTTTTTGGTTTTTTGAAAGTGCGT
CTTCAGAGCGCTTTTGGTTTTCAAAAGCGCTCTGAAGTTCCTATACTTTCTAGAGAATAGGAACTTCGGAATAGG
AACTTCAAAGCGTTTCCGAAAACGAGCGCTTCCGAAAATGCAACGCGAGCTGCGCACATACAGCTCACTGTTCAC
GTCGCACCTATATCTGCGTGTTGCCTGTATATATATATACATGAGAAGAACGGCATAGTGCGTGTTTATGCTTAA
ATGCGTACTTATATGCGTCTATTTATGTAGGATGAAAGGTAGTCTAGTACCTCCTGTGATATTATCCCATTCCAT
GCGGGGTATCGTATGCTTCCTTCAGCACTACCCTTTAGCTGTTCTATATGCTGCCACTCCTCAATTGGATTAGTC
TCATCCTTCAATGCTATCATTTCCTTTGATATTGGATCATACCCTAGAAGTATTACGTGATTTCTGCCCCTTAC
CCTCGTTGCTACTCTCCTTTTTTTCGTGGGAACCGCTTTAGGGCCCTCAGTGATGGTGTTTTGTAATTTATATGC
TCCTCTTGCATTTGTGTCTCTACTTCTTGTTCGCCTGGAGGGAACTTCTTCATTTGTATTAGCATGGTTCACTTC
AGTCCTTCCTTCCAACTCACTCTTTTTTGCTGTAAACGATTCTCTGCCGCCAGTTCATTGAAACTATTGAATAT
ATCCTTTAGAGATTCCGGGATGAATAAATCACCTATTAAAGCAGCTTGACGATCTGGTGGAACTAAAGTAAGCAA
TTGGGTAACGACGCTTACGAGCTTCATAACATCTTCTTCCGTTGGAGCTGGTGGGACTAATAACTGTGTACAATC
CATTTTTCTCATGAGCATTTCGGTAGCTCTCTTCTTGTCTTTCTCGGGCAATCTTCCTATTATTATAGCAATAGA
TTTGTATAGTTGCTTTCTATTGTCTAACAGCTTGTTATTCTGTAGCATCAAATCTATGGCAGCCTGACTTGCTTC
TTGTGAAGAGAGCATACCATTTCCAATCGAATCAAACCTTTCCTTAACCATCTTCGCAGCAGGCAAAATTACCTC
AGCACTGGAGTCAGAAGATACGCTGGAATCTTCTGCGCTAGAATCAAGACCATACGGCCTACCGGTTGTGAGAGA
TTCCATGGGCCTTATGACATATCCTGGAAAGAGTAGCTCATCAGACTTACGTTTACTCTCTATATCAATATCTAC
ATCAGGAGCAATCATTTCAATAAACAGCCGACATACATCCCAGACGCTATAAGCTGTACGTGCTTTTACCGTCAG
ATTCTTGGCTGTTTCAATGTCGTCCATTTTGGTTTTCTTTTACCAGTATTGTTCGTTTGATAATGTATTCTTGCT
TATTACATTATAAATCTGTCAGATCACATGTCAAAACAACTTTTTATCACAAGATAGTACCGCAAAACGAACC
TGCGGGCCGTCTAAAAATTAAGGAAAAGCAGCAAAGGTGCATTTTTAAAAATATGAAATGAAGATACCGCAGTACC
AATTATTTTCGCAGTACAAATAATGCGCGGCCGGTGCATTTTTCGAAAGAACGCGAGACAAACAGGACAATTAAA
GTTAGTTTTTCGAGTTAGCGTGTTTGAATACTGCAAGATACAAGATAAATAGAGTAGTTGAAACTAGATATCAAT
TGCACACAAGATCGGCGCTAAGCATGCCACAATTTGATATATTATGTAAAACACCACCTAAGGTGCTTGTTCGTC
AGTTTGTGGAAAGGTTTGAAAGACCTTCAGGTGAGAAAATAGCATTATGTGCTGCTGAACTAACCTATTTATGTT
GGATGATTACACATAACGGAACAGCAATCAAGAGAGCCACATTCATGAGCTATAATACTATCATAAGCAATTCGC
TGAGTTTCGATATTGTCAATAAATCACTCCAGTTAAATACAAGACGCAAAAGCAACAATTCTGGAAGCCTCAT
TAAAGAAATTGATTCCTGCTTGGGAATTTACAATTATTCCTTACTATGGACAAAAACATCAATCTGATATCACTG
ATATTGTAAGTAGTTTGCAATTACAGTTCGAATCATCGGAAGAAGCAGATAAGGGAAATAGCCACAGTAAAAAAA
TGCTTAAAGCACTTCTAAGTGAGGGTGAAAGCATCTGGGAGATCACTGAGAAAATACTAAATTCGTTTGAGTATA
CTTCGAGATTTACAAAAACAAAACTTTATACCAATTCCTCTTCCTAGCTACTTTCATCAATTGTGGAAGATTCA
GCGATATTAAGAACGTTGATCCGAAATCATTTAAATTAGTCCAAAATAAGTATCTGGGAGTAATAATCCAGTGTT
TAGTGACAGAGACAAAGACAAGCGTTAGTAGGCACATATACTTCTTTAGCGCAAGGGGTAGGTAGC
```

*FIG. 3D*

ParvoB19.Opti.VP1 acgcgtacaaaacaaaATGTCTAAGAAATCTGGTAAATGGTGGGAATCTGATGATAAATTTGCTAAGGCTGTTTACC
AACAATTTGTTGAATTTTACGAAAAGGTTACTGGTACTGATTTGGAATTGATTCAAATTTTGAAGGATCATTACAAC
ATTTCTTTGGATAATCCATTGGAAAATCCATCTTCATTGTTTGATTTGGTTGCTAGAATTAAGAACAACTTGAAGAA
CTCTCCAGATTTGTATTCTCATCATTTCCAATCTCATGGTCAATTGTCTGATCATCCACATGCTTTATCTTCATCTT
CATCTCATGCTGAACCAAGAGGTGAAAATGCTGTTTTATCTTCTGAAGATTTGCATAAACCAGGTCAAGTTTCTGTT
CAATTGCCAGGTACTAATTACGTTGGTCCAGGTAATGAATTGCAAGCTGGTCCACCACAATCTGCTGTTGATTCTGC
TGCTAGAATTCATGATTTCAGATACTCTCAATTGGCTAAGTTGGGTATTAATCCATATACTCATTGGACTGTTGCTG
ATGAAGAATTGTTGAAGAACATTAAGAATGAAACTGGTTTTCAAGCTCAAGTTGTTAAAGATTACTTCACTTTGAAA
GGTGCTGCTGCTCCAGTTGCTCATTTTCAAGGTTCTTTGCCAGAAGTTCCAGCTTATAACGCTTCTGAAAAATATCC
ATCTATGACATCTGTTAATTCTGCTGAAGCATCTACTGGTGCAGGTGGAGGTGGTTCTAATTCTGTTAAATCTATGT
GGTCTGAAGGTGCTACTTTTTCTGCTAATTCAGTTACTTGTACTTTCTCTAGACAATTCTTGATTCCATATGATCCA
GAACATCATTACAAAGTTTTTCACCAGCTGCTTCATCTTGTCATAATGCTTCAGGTAAAGAAGCTAAGGTTTGTAC
TATTTCTCCAATTATGGGTTATTCTACTCCTTGGAGATACTTGGATTTTAATGCTTTGAACTTGTTTTTTTCTCCAT
TGGAATTTCAACATTTGATTGAAAACTACGGTTCTATTGCTCCAGATGCTTTGACTGTTACTATTTCTGAAATTGCT
GTTAAGGATGTTACTGATAAAACAGGTGGTGGTGTTCAAGTTACTGATTCTACTACTGGTAGATTGTGCATGTTGGT
TGATCATGAATACAAATACCCATACGTTTTGGGTCAAGGTCAAGATACTTTGGCTCCAGAATTGCCAATTTGGGTTT
ATTTTCCACCACAATACGCTTATTTGACTGTTGGTGATGTTAATACTCAAGGTATTTCTGGTGATTCTAAAAAGTTG
GCTTCTGAAGAATCTGCTTTTTACGTTTTGGAACATTCTTCTTTTCAATTGTTGGGTACTGGTGGTACTGCTTCTAT
GTCTTACAAATTTCCACCAGTTCCACCTGAAAATTTGGAAGGTTGTTCTCAACATTTTTACGAAATGTACAATCCAT
TGTATGGTTCTAGATTGGGTGTTCCAGATACTTTGGGTGGTGATCCAAAATTTAGATCTTTGACTCATGAAGATCAT
GCTATTCAACCACAAAATTTCATGCCAGGTCCATTGGTTAATTCTGTTTCTACTAAAGAAGGTGATTCTTCTAATAC
AGGTGCTGGTAAAGCATTGACTGGTTTGTCTACTGGTACTTCTCAAAACACTAGAATTTCTTTAAGACCAGGTCCAG
TTTCACAACCATATCATCATTGGGATACTGATAAGTACGTTACTGGTATTAATGCTATTTCACATGGTCAAACTACT
TATGGTAATGCTGAAGATAAAGAATATCAACAAGGTGTTGGTAGATTTCCAAACGAAAAAGAACAATTGAAACAATT
GCAAGGTTTGAATATGCATACTTACTTTCCAAACAAAGGTACTCAACAATACACTGATCAAATTGAAAGACCATTGA
TGGTTGGTTCTGTTTGGAATAGAAGAGCTTTGCATTATGAATCTCAATTGTGGTCTAAGATTCCAAATTTAGATGAT
TCTTTCAAGACTCAATTTGCTGCTTTGGGTGGTTGGGGTTTGCATCAACCTCCACCACAAATTTTCTTGAAGATTTT
GCCACAATCTGGTCCAATTGGTGGTATTAAATCTATGGGTATTACTACTTTGGTTCAATATGCTGTTGGTATTATGA
CTGTTACAATGACTTTTAAGTTGGGTCCAAGAAAAGCTACAGGTAGATGGAATCCACAACCAGGTGTTTATCCACCA
CATGCTGCTGGTCATTTGCCTTACGTTTTGTATGATCCAACTGCTACTGATGCTAAACAACATCATAGACATGGTTA
TGAAAAACCTGAAGAATTGTGGACTGCTAAATCTAGAGTTCATCCATTGTAATGAgtcgac

FIG. 4

ParvoB19.Opti.VP2 cctaggacaaaacaaaATGACATCTGTTAATTCTGCTGAAGCATCTACTGGTGCAGGTGGAGGTGGTTCTAATTCTG
TTAAATCTATGTGGTCTGAAGGTGCTACTTTTTCTGCTAATTCAGTTACTTGTACTTTCTCTAGACAATTCTTGATT
CCATATGATCCAGAACATCATTACAAAGTTTTTTCACCAGCTGCTTCATCTTGTCATAATGCTTCAGGTAAAGAAGC
TAAGGTTTGTACTATTTCTCCAATTATGGGTTATTCTACTCCTTGGAGATACTTGGATTTTAATGCTTTGAACTTGT
TTTTTTCTCCATTGGAATTTCAACATTTGATTGAAAACTACGGTTCTATTGCTCCAGATGCTTTGACTGTTACTATT
TCTGAAATTGCTGTTAAGGATGTTACTGATAAAACAGGTGGTGGTGTTCAAGTTACTGATTCTACTACTGGTAGATT
GTGCATGTTGGTTGATCATGAATACAAATACCCATACGTTTTGGGTCAAGGTCAAGATACTTTGGCTCCAGAATTGC
CAATTTGGGTTTATTTTCCACCACAATACGCTTATTTGACTGTTGGTGATGTTAATACTCAAGGTATTTCTGGTGAT
TCTAAAAAGTTGGCTTCTGAAGAATCTGCTTTTTACGTTTTGGAACATTCTTCTTTTCAATTGTTGGGTACTGGTGG
TACTGCTTCTATGTCTTACAAATTTCCACCAGTTCCACCTGAAAATTTGGAAGGTTGTTCTCAACATTTTTACGAAA
TGTACAATCCATTGTATGGTTCTAGATTGGGTGTTCCAGATACTTTGGGTGGTGATCCAAAATTTAGATCTTTGACT
CATGAAGATCATGCTATTCAACCACAAAATTTCATGCCAGGTCCATTGGTTAATTCTGTTTCTACTAAAGAAGGTGA
TTCTTCTAATACAGGTGCTGGTAAAGCATTGACTGGTTTGTCTACTGGTACTTCTCAAAACACTAGAATTTCTTTAA
GACCAGGTCCAGTTTCACAACCATATCATCATTGGGATACTGATAAGTACGTTACTGGTATTAATGCTATTTCACAT
GGTCAAACTACTTATGGTAATGCTGAAGATAAAGAATATCAACAAGGTGTTGGTAGATTTCCAAACGAAAAAGAACA
ATTGAAACAATTGCAAGGTTTGAATATGCATACTTACTTTCCAAACAAAGGTACTCAACAATACACTGATCAAATTG
AAAGACCATTGATGGTTGGTTCTGTTTGGAATAGAAGAGCTTTGCATTATGAATCTCAATTGTGGTCTAAGATTCCA
AATTTAGATGATTCTTTCAAGACTCAATTTGCTGCTTTGGGTGGTTGGGGTTTGCATCAACCTCCACCACAAATTTT
CTTGAAGATTTTGCCACAATCTGGTCCAATTGGTGGTATTAAATCTATGGGTATTACTACTTTGGTTCAATATGCTG
TTGGTATTATGACTGTTACAATGACTTTTAAGTTGGGTCCAAGAAAAGCTACAGGTAGATGGAATCCACAACCAGGT
GTTTATCCACCACATGCTGCTGGTCATTTGCCTTACGTTTTGTATGATCCAACTGCTACTGATGCTAAACAACATCA
TAGACATGGTTATGAAAAACCTGAAGAATTGTGGACTGCTAAATCTAGAGTTCATCCATTGTAATGAgcggccgc

*FIG. 5*

ADH2 / GAPDH promoter (as BamHI / HindIII fragment) used in the expression of ParvoB19 VP2

GGATCCTTCAATATGCGCACATACGCTGTTATGTTCAAGGTCCCTTCGTTTAAGAACGAAAGCGGTCTTCCTTTTGA
GGGATGTTTCAAGTTGTTCAAATCTATCAAATTTGCAAATCCCCAGTCTGTATCTAGAGCGTTGAATCGGTGATGCG
ATTTGTTAATTAAATTGATGGTGTCACCATTACCAGGTCTAGATATACCAATGGCAAACTGAGCACAACAATACCAG
TCCGGATCAACTGGCACCATCTCTCCCGTAGTCTCATCTAATTTTTCTTCCGGATGAGGTTCCAGATATACCGCAAC
ACCTTTATTATGGTTTCCCTGAGGGAATAATAGAATGTCCCATTCGAAATCACCAATTCTAAACCTGGGCGAATTGT
ATTTCGGGTTTGTTAACTCGTTCCAGTCAGGAATGTTCCACGTGAAGCTATCTTCCAGCAAAGTCTCCACTTCTTCA
TCAAATTGTgGGAGAATACTCCCAATGCTCTTATCTATGGGACTTCCGGGAAACACAGTACCGATACTTCCCAATTC
GTCTTCAGAGCTCATTGTTTGTTTGAAGAGACTAATCAAAGAATCGTTTTCTCAAAAAAATTAATATCTTAACTGAT
AGTTTGATCAAAGGGGCAAAACGTAGGGGCAAACAAACGGAAAAATCGTTTCTCAAATTTTCTGATGCCAAGAACTC
TAACCAGTCTTATCTAAAAATTGCCTTATGATCCGTCTCTCCGGTTACAGCCTGTGTAACTGATTAATCCTGCCTTT
CTAATCACCATTCTAATGTTTTAATTAAGGGATTTTGTCTTCATTAACGGCTTTCGCTCATAAAAATGTTATGACGT
TTTGCCCGCAGGCGGGAAACCATCCACTTCACGAGACTGATCTCCTCTGCCGGAACACCGGGCATCTCCAACTTATA
AGTTGGAGAAATAAGAGAATTTCAGATTGAGAGAATGAAAAAAAAAAACCCTTAGTTCATAGGTCCATTCTCTTAGC
GCAACTACAGAGAACAGGGGCACAAACAGGCAAAAAACGGGCACAACCTCAATGGAGTGATGCAACCTGCCTGGAGT
AAATGATGACACAAGGCAATTGACCCACGCATGTATCTATCTCATTTTCTTACACCTTCTATTACCTTCTGCTCTCT
CTGATTTGGAAAAAGCTGAAAAAAAAGGTTGAAACCAGTTCCCTGAAATTATTCCCCTACTTGACTAATAAGTATAT
AAAGACGGTAGGTATTGATTGTAATTCTGTAAATCTATTTCTTAAACTTCTTAAATTCTACTTTTATAGTTAGTCTT
TTTTTTAGTTTTAAAACACCAAGAACTTAGTTTCGAATAAACACACATAAACAAACAAGCTT

*FIG. 6*

The "delta As" version of the ADH2 / GAPDH promoter in which 10 bases of GAPDH sequence has been replaced with 14 bases of parvovirus B19 native viral sequence (underlined) as it naturally occurs immediately upstream from the initiating Met of VP1 (highlighted in black)

GGATCCTTCAATATGCGCACATACGCTGTTATGTTCAAGGTCCCTTCGTTTAAGAACGAA
AGCGGTCTTCCTTTTGAGGGATGTTTCAAGTTGTTCAAATCTATCAAATTTGCAAATCCC
CAGTCTGTATCTAGAGCGTTGAATCGGTGATGCGATTTGTTAATTAAATTGATGGTGTCA
CCATTACCAGGTCTAGATATACCAATGGCAAACTGAGCACAACAATACCAGTCCGGATCA
ACTGGCACCATCTCTCCCGTAGTCTCATCTAATTTTTCTTCCGGATGAGGTTCCAGATAT
ACCGCAACACCTTTATTATGGTTTCCCTGAGGGAATAATAGAATGTCCCATTCGAAATCA
CCAATTCTAAACCTGGGCGAATTGTATTTCGGGTTTGTTAACTCGTTCCAGTCAGGAATG
TTCCACGTGAAGCTATCTTCCAGCAAAGTCTCCACTTCTTCATCAAATTGTGGGAGAATA
CTCCCAATGCTCTTATCTATGGGACTTCCGGGAAACACAGTACCGATACTTCCCAATTCG
TCTTCAGAGCTCATTGTTTGTTTGAAGAGACTAATCAAAGAATCGTTTTCTCAAAAAAAT
TAATATCTTAACTGATAGTTTGATCAAAGGGGCAAAACGTAGGGGCAAACAAACGGAAAA
ATCGTTTCTCAAATTTTCTGATGCCAAGAACTCTAACCAGTCTTATCTAAAAATTGCCTT
ATGATCCGTCTCTCCGGTTACAGCCTGTGTAACTGATTAATCCTGCCTTTCTAATCACCA
TTCTAATGTTTTAATTAAGGGATTTTGTCTTCATTAACGGCTTTCGCTCATAAAAATGTT
ATGACGTTTTGCCCGCAGGCGGGAAACCATCCACTTCACGAGACTGATCTCCTCTGCCGG
AACACCGGGCATCTCCAACTTATAAGTTGGAGAAATAAGAGAATTTCAGATTGAGAGAAT
GAAAAAAAAAAACCCTTAGTTCATAGGTCCATTCTCTTAGCGCAACTACAGAGAACAGGG
GCACAAACAGGCAAAAAACGGGCACAACCTCAATGGAGTGATGCAACCTGCCTGGAGTAA
ATGATGACACAAGGCAATTGACCCACGCATGTATCTATCTCATTTTCTTACACCTTCTAT
TACCTTCTGCTCTCTCTGATTTGGAAAAAGCTGAAAAAAAAAGGTTGAAACCAGTTCCCTG
AAATTATTCCCCTACTTGACTAATAAGTATATAAAGACGGTAGGTATTGATTGTAATTCT
GTAAATCTATTTCTTAAACTTCTTAAATTCTACTTTTATAGTTAGTCTTTTTTTTAGTTT
TAAAACACCAAGAACTTAGTTTCGAATAAACACACATAAACAAACAAGCTTTGTAGATTATG

*FIG. 7*

ADH2 / GAPDH promoter (as BamHI / MluI fragment) with TATA deletion, used in expression of ParvoB19 VP1 and VP1mut

GGATCCTTCAATATGCGCACATACGCTGTTATGTTCAAGGTCCCTTCGTTTAAGAACGAA
AGCGGTCTTCCTTTTGAGGGATGTTTCAAGTTGTTCAAATCTATCAAATTTGCAAATCCC
CAGTCTGTATCTAGAGCGTTGAATCGGTGATGCGATTTGTTAATTAAATTGATGGTGTCA
CCATTACCAGGTCTAGATATACCAATGGCAAACTGAGCACAACAATACCAGTCCGGATCA
ACTGGCACCATCTCTCCCGTAGTCTCATCTAATTTTTCTTCCGGATGAGGTTCCAGATAT
ACCGCAACACCTTTATTATGGTTTCCCTGAGGGAATAATAGAATGTCCCATTCGAAATCA
CCAATTCTAAACCTGGGCGAATTGTATTTCGGGTTTGTTAACTCGTTCCAGTCAGGAATG
TTCCACGTGAAGCTATCTTCCAGCAAAGTCTCCACTTCTTCATCAAATTGTGGGAGAATA
CTCCCAATGCTCTTATCTATGGGACTTCCGGGAAACACAGTACCGATACTTCCCAATTCG
TCTTCAGAGCTCATTGTTTGTTTGAAGAGACTAATCAAAGAATCGTTTTCTCAAAAAAAT
TAATATCTTAACTGATAGTTTGATCAAAGGGGCAAAACGTAGGGGCAAACAAACGGAAAA
ATCGTTTCTCAAATTTTCTGATGCCAAGAACTCTAACCAGTCTTATCTAAAAATTGCCTT
ATGATCCGTCTCTCCGGTTACAGCCTGTGTAACTGATTAATCCTGCCTTTCTAATCACCA
TTCTAATGTTTTAATTAAGGGATTTTGTCTTCATTAACGGCTTTCGCTCATAAAAATGTT
ATGACGTTTTGCCCGCAGGCGGGAAACCATCCACTTCACGAGACTGATCTCCTCTGCCGG
AACACCGGGCATCTCCAACTTATAAGTTGGAGAAATAAGAGAATTTCAGATTGAGAGAAT
GAAAAAAAAAAACCCTTAGTTCATAGGTCCATTCTCTTAGCGCAACTACAGAGAACAGGG
GCACAAACAGGCAAAAAACGGGCACAACCTCAATGGAGTGATGCAACCTGCCTGGAGTAA
ATGATGACACAAGGCAATTGACCCACGCATGTATCTATCTCATTTTCTTACACCTTCTAT
TACCTTCTGCTCTCTCTGATTTGGAAAAAGCTGAAAAAAAAAGGTTGAAACCAGTTCCCTG
AAATTATTCCCCTAGCATTGTAATTCTGTAAATCTATTTCTTAAACTTCTTAAATTCTAC
TTTTATAGTTAGTCTTTTTTTTAGTTTAAAACACCAAGAACTTAGTTTCGAATAAACAC
ACATAAACAAACACGCGT

*FIG. 8*

ParvoB19 VP1 with 1SS (synthetic start-stop sequence, underlined) upstream from the junction between the ADH2 / GAPDH promoter and the initiating Met of VP1 (highlighted in black)

ACGCGT<u>ATGATGCCTAGTTAATGAACAAAACAAA</u>ATGTCTAAGAAATCCGGAAAATGGTG
GGAATCTGATGATAAATTTGCTAAGGCTGTTTACCAACAATTTGTTGAATTTTACGAAAA
GGTTACTGGTACTGATTTGGAATTGATTCAAATTTTGAAGGATCATTACAACATTTCTTT
GGATAATCCATTGGAAAATCCATCTTCATTGTTTGATTTGGTTGCTAGAATTAAGAACAA
CTTGAAGAACTCTCCAGATTTGTATTCTCATCATTTCCAATCTCATGGTCAATGTCTGA
TCATCCACATGCTTTATCTTCATCTTCATCTCATGCTGAACCAAGAGGTGAAAATGCTGT
TTTATCTTCTGAAGATTTGCATAAACCAGGTCAAGTTTCTGTTCAATTGCCAGGTACTAA
TTACGTTGGTCCAGGTAATGAATTGCAAGCTGGTCCACCACAATCTGCTGTTGATTCTGC
TGCTAGAATTCATGATTTCAGATACTCTCAATTGGCTAAGTTGGGTATTAATCCATATAC
TCATTGGACTGTTGCTGATGAAGAATTGTTGAAGAACATTAAGAATGAAACTGGTTTTCA
AGCTCAAGTTGTTAAAGATTACTTCACTTTGAAAGGTGCTGCTGCTCCAGTTGCTCATTT
TCAAGGTTCTTTGCCAGAAGTTCCAGCTTATAACGCTTCTGAAAAATATCCATCTATGAC
ATCTGTTAATTCTGCTGAAGCATCTACTGGTGCAGGTGGAGGTGGTTCTAATTCTGTTAA
ATCTATGTGGTCTGAAGGTGCTACTTTTTCTGCTAATTCAGTTACTTGTACTTTCTCTAG
ACAATTCTTGATTCCATATGATCCAGAACATCATTACAAAGTTTTTTCACCAGCTGCTTC
ATCTTGTCATAATGCTTCAGGTAAAGAAGCTAAGGTTTGTACTATTTCTCCAATTATGGG
TTATTCTACTCCTTGGAGATACTTGGATTTTAATGCTTTGAACTTGTTTTTCTCCATT
GGAATTTCAACATTTGATTGAAAACTACGGTTCTATTGCTCCAGATGCTTTGACTGTTAC
TATTTCTGAAATTGCTGTTAAGGATGTTACTGATAAAACAGGTGGTGGTGTTCAAGTTAC
TGATTCTACTACTGGTAGATTGTGCATGTTGGTTGATCATGAATACAAATACCCATACGT
TTTGGGTCAAGGTCAAGATACTTTGGCTCCAGAATTGCCAATTTGGGTTTATTTTCCACC
ACAATACGCTTATTTGACTGTTGGTGATGTTAATACTCAAGGTATTTCTGGTGATTCTAA
AAAGTTGGCTTCTGAAGAATCTGCTTTTTACGTTTTGGAACATTCTTCTTTTCAATTGTT
GGGTACTGGTGGTACTGCTTCTATGTCTTACAAATTTCCACCAGTTCCACCTGAAAATTT
GGAAGGTTGTTCTCAACATTTTTACGAAATGTACAATCCATTGTATGGTTCTAGATTGGG
TGTTCCAGATACTTTGGGTGGTGATCCAAAATTTAGATCTTTGACTCATGAAGATCATGC
TATTCAACCACAAAATTTCATGCCAGGTCCATTGGTTAATTCTGTTTCTACTAAAGAAGG
TGATTCTTCTAATACAGGTGCTGGTAAAGCATTGACTGGTTTGTCTACTGGTACTTCTCA
AAACACTAGAATTTCTTTAAGACCAGGTCCAGTTTCACAACCATATCATCATTGGGATAC
TGATAAGTACGTTACTGGTATTAATGCTATTTCACATGGTCAAACTACTTATGGTAATGC
TGAAGATAAAGAATATCAACAAGGTGTTGGTAGATTTCCAAACGAAAAAGAACAATTGAA
ACAATTGCAAGGTTTGAATATGCATACTTACTTTCCAAACAAAGGTACTCAACAATACAC
TGATCAAATTGAAAGACCATTGATGGTTGGTTCTGTTTGGAATAGAAGAGCTTTGCATTA
TGAATCTCAATTGTGGTCTAAGATTCCAAATTTAGATGATTCTTTCAAGACTCAATTTGC
TGCTTTGGGTGGTTGGGGTTTGCATCAACCTCCACCACAAATTTTCTTGAAGATTTTGCC
ACAATCTGGTCCAATTGGTGGTATTAAATCTATGGGTATTACTACTTTGGTTCAATATGC
TGTTGGTATTATGACTGTTACAATGACTTTTAAGTTGGGTCCAAGAAAAGCTACAGGTAG
ATGGAATCCACAACCAGGTGTTTATCCACCACATGCTGCTGGTCATTTGCCTTACGTTTT
GTATGATCCAACTGCTACTGATGCTAAACAACATCATAGACATGGTTATGAAAAACCTGA
AGAATTGTGGACTGCTAAATCTAGAGTTCATCCATTGTAATGAGTCGAC

*FIG. 9*

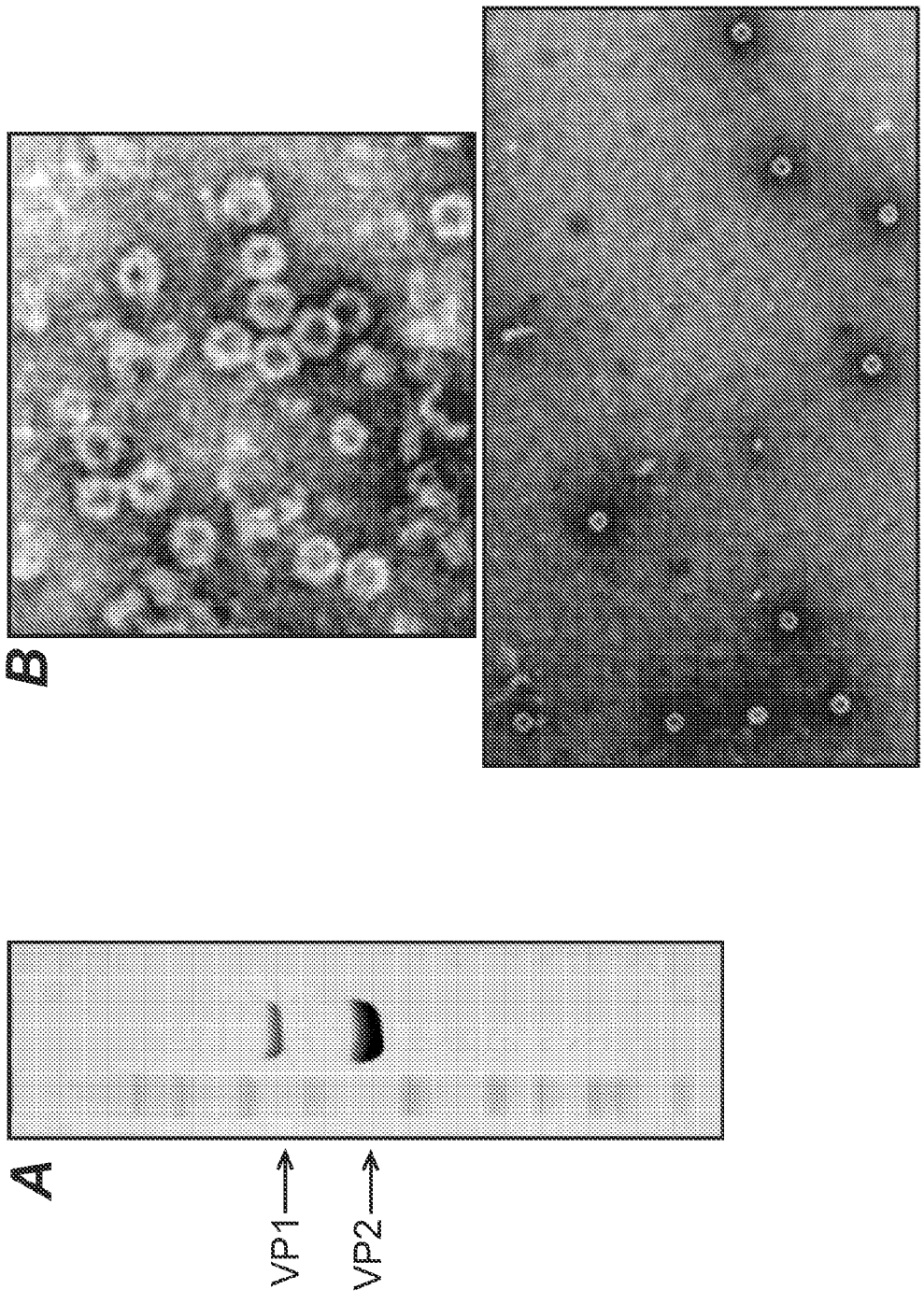

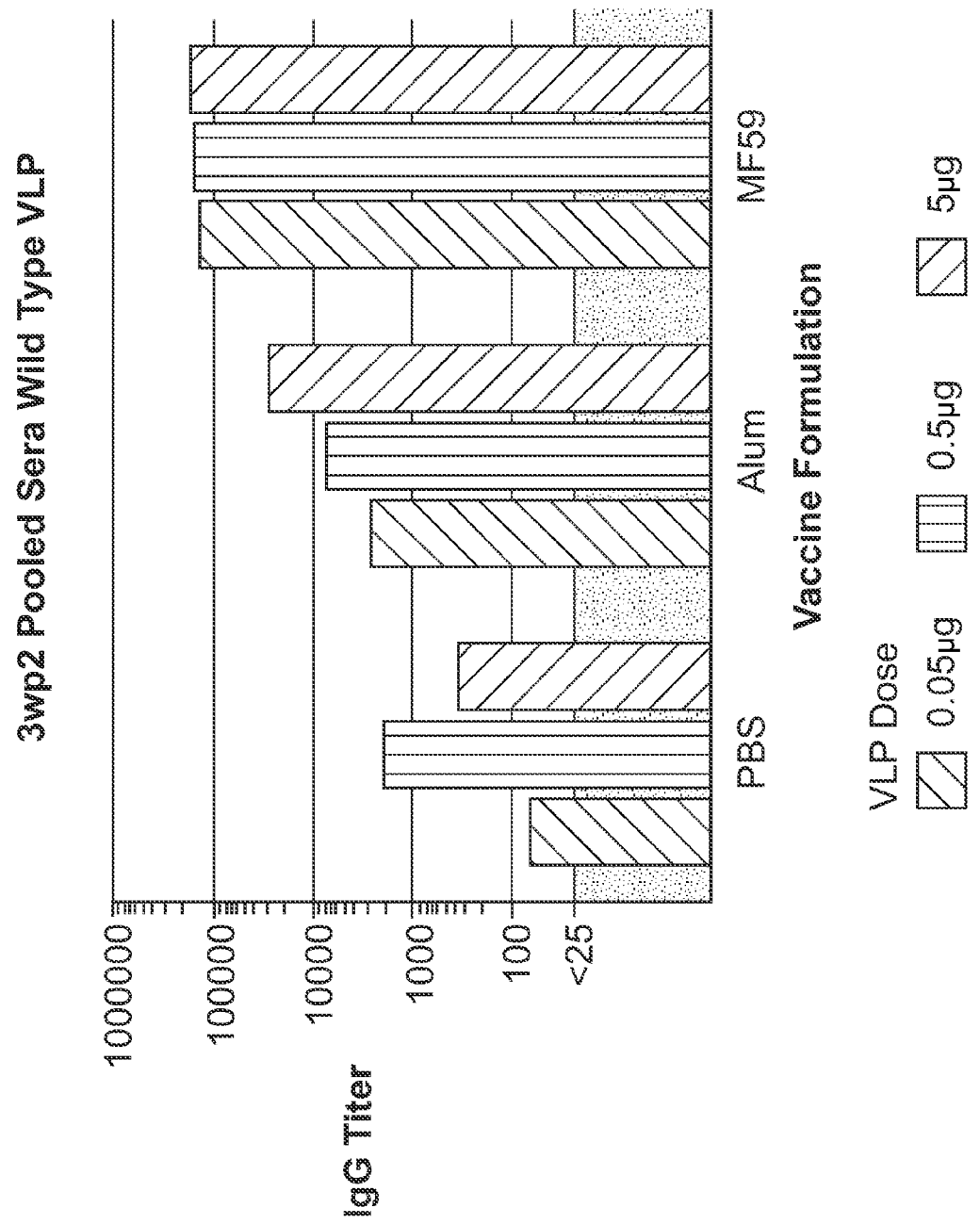

VP1 wild type amino acid sequence

Amino Acids :781
Molecular Weight : 84 kDa

MSKKSGKWWESDDKFAKAVYQQFVEFYEKVTGTDLELIQILKDHYNISLDNPLENPSSLF
DLVARIKNNLKNSPDLYSHHFQSHGQLSDHPHALSSSSSHAEPRGENAVLSSEDLHKPGQ
VSVQLPGTNYVGPGNELQAGPPQSAVDSAARIHDFRYSQLAKLGINPYTHWTVADEELLK
NIKNETGFQAQVVKDYFTLKGAAAPVAHFQGSLPEVPAYNASEKYPSMTSVNSAEASTGA
GGGGSNSVKSMWSEGATFSANSVTCTFSRQFLIPYDPEHHYKVFSPAASSCHNASGKEAK
VCTISPIMGYSTPWRYLDFNALNLFFSPLEFQHLIENYGSIAPDALTVTISEIAVKDVTD
KTGGGVQVTDSTTGRLCMLVDHEYKYPYVLGQGQDTLAPELPIWVYFPPQYAYLTVGDVN
TQGISGDSKKLASEESAFYVLEHSSFQLLGTGGTASMSYKFPPVPPENLEGCSQHFYEMY
NPLYGSRLGVPDTLGGDPKFRSLTHEDHAIQPQNFMPGPLVNSVSTKEGDSSNTGAGKAL
TGLSTGTSQNTRISLRPGPVSQPYHHWDTDKYVTGINAISHGQTTYGNAEDKEYQQGVGR
FPNEKEQLKQLQGLNMHTYFPNKGTQQYTDQIERPLMVGSVWNRRALHYESQLWSKIPNL
DDSFKTQFAALGGWGLHQPPPQIFLKILPQSGPIGGIKSMGITTLVQYAVGIMTVTMTFK
LGPRKATGRWNPQPGVYPPHAAGHLPYVLYDPTATDAKQHHRHGYEKPEELWTAKSRVHP
L

VP2 amino acid sequence

Amino Acids :554
Molecular Weight : 58 kDa

MTSVNSAEASTGAGGGGSNSVKSMWSEGATFSANSVTCTFSRQFLIPYDPEHHYKVFSPA
ASSCHNASGKEAKVCTISPIMGYSTPWRYLDFNALNLFFSPLEFQHLIENYGSIAPDALT
VTISEIAVKDVTDKTGGGVQVTDSTTGRLCMLVDHEYKYPYVLGQGQDTLAPELPIWVYF
PPQYAYLTVGDVNTQGISGDSKKLASEESAFYVLEHSSFQLLGTGGTASMSYKFPPVPPE
NLEGCSQHFYEMYNPLYGSRLGVPDTLGGDPKFRSLTHEDHAIQPQNFMPGPLVNSVSTK
EGDSSNTGAGKALTGLSTGTSQNTRISLRPGPVSQPYHHWDTDKYVTGINAISHGQTTYG
NAEDKEYQQGVGRFPNEKEQLKQLQGLNMHTYFPNKGTQQYTDQIERPLMVGSVWNRRAL
HYESQLWSKIPNLDDSFKTQFAALGGWGLHQPPPQIFLKILPQSGPIGGIKSMGITTLVQ
YAVGIMTVTMTFKLGPRKATGRWNPQPGVYPPHAAGHLPYVLYDPTATDAKQHHRHGYEK
PEELWTAKSRVHPL

FIG. 16

METHOD FOR GENERATING A PARVOVIRUS B19 VIRUS-LIKE PARTICLE

This application is the U.S. National Phase of International Application No. PCT/US2011/031630, filed Apr. 7, 2011 and published in English, which claims priority from U.S. provisional patent application 61/321,856, filed Apr. 7, 2010, the complete contents of which are incorporated herein by reference.

The instant application contains a Sequence Listing which has been submitted via EFS-Web and is hereby incorporated by reference in its entirety. The ASCII copy, created on Jun. 28, 2013, is named USPTOsubseq13639820forPAT054048-US-PCT.txt, and is 53,248 bytes in size.

Parvovirus B19 produces mild, self-limiting illness in immunocompetent, hematologically normal individuals, however, it may cause serious illness in people with sickle-cell disease or other types of chronic anemia. In such people, parvovirus B19 can cause an acute, severe anemia. The ill person may be pale, weak, and tired. Furthermore, people who have problems with their immune systems may also develop a chronic anemia with parvovirus B19 infection that requires medical treatment. People who have leukemia or cancer, those born with immune deficiencies, who have received an organ transplant, or who have human immunodeficiency virus (HIV) infection are at risk for serious illness due to parvovirus B19 infection. Hematologically normal individuals who contract parvovirus B19 initially as an adult can present with arthalgias that last for weeks. Parvovirus B19 infection in pregnant women is also associated with hydrops fetalis due to severe fetal anemia, sometimes leading to miscarriage or stillbirth. Acquisition of parvovirus B19 by blood transfusion in those with acute anemias due to blood loss or other causes can prevent correction of the anemia by hematopoiesis.

Parvovirus B19 most commonly causes a childhood exanthem called fifth disease or erythema infectiosum, commonly known as slapped cheek syndrome. A person infected with parvovirus B19 is contagious during the early part of the illness, before the rash appears. Parvovirus B19 has been found in the respiratory secretions (e.g., saliva, sputum or nasal mucus) of infected persons before the onset of rash, when they appear to "just have a cold." The virus is probably spread from person to person by direct contact with those secretions. Parvovirus B19 is now considered a serious disease because of the complications that can occur, especially for pregnant women and their fetuses, or for people with unhealthy immune systems.

The symptoms of parvovirus B19 infection include a mild nonspecific prodromal illness that may consist of fever, malaise, headache, myalgia, nausea, and rhinorrhea. Symptoms typically begin 5-7 days after initial infection. These symptoms correspond to the initial viremia and dissipate in 2-3 days. Approximately one week later, a bright red macular exanthema appears on the cheeks and is often associated with circumoral pallor. A diffuse maculopapular rash can appear 1-4 days later and fades to a lacy eryhematous rash, which may be pruritic and may spread gradually toward the distal extremeties.

Parvovirus B19 belongs to the Erythroviruses genus of the Parvoviridae family of small DNA viruses. It is a non-enveloped, icosahedral virus that contains a single-stranded linear DNA genome. The parvovirus B19 virion is 20-25 nm in diameter and has a genome of 5.6 kb (Clewley, 1984, Cotmore & Tattersall, 1984). The parvovirus B19 capsid consists of an 83 kDa minor structural protein, VP1, and a 58 kDa major structural protein, VP2. It has a non-segmented single stranded DNA genome surrounded by a protein shell containing two structural proteins, VP1 and VP2 in a ~5% to ~95% ratio (Ozawa et al., 1987). The sequences of the two proteins are co-linear, with VP2 being identical to the carboxyl-terminal region of VP1; however, VP1 comprises an additional 227 amino acids at the amino-terminus. Long lasting antibody responses are directed to both VP1 and VP2 proteins and thus these proteins alone are expected to raise a significant immune response.

The expression and purification in insect cells of parvovirus B19 VP1/VP2 VLPs has been previously described (U.S. Pat. No. 5,508,186). Despite what is known about parvovirus B19, there is no vaccine or practical medicine that prevents parvovirus B19 infection. Human immunoglobulin-containing preparations are sometimes used to treat chronic parvovirus B19 infections in immunodeficient individuals. However, immunoglobulin injections are not sufficiently practical, long lasting, or affordable for widespread or routine prophylactic use. Excluding those with fifth disease from social interaction, e.g., at work, child care centers, or schools, is not an effective way to prevent the spread of the virus, because individuals are contagious well before they develop the signatory rash. Thus, a need exists for an improved parvovirus B19 vaccine development approach that allows for efficient preparation of parvovirus B19 immunogenic materials.

SUMMARY OF THE INVENTION

The present invention, in part, provides methods for generating parvovirus virus-like particles, such as parvovirus B19 virus-like particles. In some aspects, the methods of the invention comprise providing a host cell with a recombinant nucleic acid, such as an expression vector, comprising both parvovirus VP1 and parvovirus VP2 and maintaining the host cell under conditions whereby the VP1 and VP2 proteins are expressed and assembled into parvovirus VLPs. In another aspect, the method of the invention comprises providing a bicistronic nucleic acid vaccine that leads to expression of parvovirus VP2 and lower levels of parvovirus VP1 in a host, such that VLPs form in the immunized host.

The invention relates to a method of producing a parvovirus virus like particle (VLP), comprising: (a) providing a host cell that contains a recombinant nucleic acid molecule that comprises a nucleotide sequence encoding parvovirus VP1 that is operably linked to a first control element, and a nucleotide sequence encoding parvovirus VP2 protein that is operably linked to a second control element, and (b) maintaining the host cell under conditions whereby the VP1 and VP2 proteins are expressed and assembled into VLPs. In a preferred method, VP1 is produced in lower abundance than VP2. Preferably, soluble VP1 is produced in lower abundance than soluble VP2. In a particular aspect, VLPs that contain VP1 and VP2 are produced. Preferably, the recombinant nucleic acid molecule is a bicistronic vector. In a particular aspect, the first control element is a variant of the second control element, and the variant comprises a modification that transcriptionally, translationally or transcriptionally and translationally decreases production of VP1 relative to VP2. For example, the first control element can comprise a deletion of at least a portion of the TATA box upstream of the nucleic acid encoding VP1, deletion of a junction site upstream of the nucleic acid encoding VP1, introduction of a transcription start or stop site upstream of the nucleic acid encoding VP1, or combinations thereof. In a particular aspect, the second control element is the ADH2/GAPDH promoter (SEQ ID NO: 19).

The host cell can be a yeast cell, insect cell, mammalian cell, avian cell, bacterium, Tetrahymena cell or combinations thereof. In one aspect, the host cells are maintained under culture conditions suitable for production of VP1 and VP2 and assembly of the proteins into VLPs. The method can further comprising isolating the VLPs. The VLPs can be isolated from host cell conditioned media, host cell lysate, host cell homogenate, or combinations thereof. Optionally, the isolated VLPs can be further purified. The isolated VLPs may be purified using a purification method selected from the group consisting of sucrose cushion, sucrose gradient centrifugation, chromatographic methods and combinations thereof.

The invention also relates to a parvovirus virus like particle (VLP) that contains VP1 and VP2 produced according to any of the methods described herein.

The invention also relates to an immunogenic composition comprising a parvovirus VLP.

The invention also relates to a recombinant nucleic acid comprising a nucleotide sequence encoding parvovirus VP1 that is operably linked to a first control element, and a nucleotide sequence encoding parvovirus VP2 protein that is operably linked to a second control element, wherein when equivalent amounts of the sequence that encodes VP1 and the sequence that encodes VP2 are present in a suitable host cell, VP1 is expressed in lower abundance relative to VP2. Preferably, soluble VP1 is produced in lower abundance than soluble VP2. In one aspect, the first control element is a weak promoter and the second control element is a strong promoter. The first control element can be a variant of the second control element, and the variant can comprise a modification that transcriptionally, translationally or transcriptionally and translationally decreases production of VP1 relative to VP2. The modification can be deletion of at least a portion of the TATA box upstream of the nucleic acid encoding VP1, deletion of a junction site upstream of the nucleic acid encoding VP1, introduction of a transcription start or stop site upstream of the nucleic acid encoding VP1, or combinations thereof. The second control element can be the ADH2/GAPDH promoter (SEQ ID NO: 19). The nucleic acid can be in the form of DNA, or RNA, and can be either single or double stranded. The recombinant nucleic acid can be a plasmid. The plasmid can include a detectable marker.

The invention also relates to a host cell comprising a recombinant nucleic acid as described herein. The recombinant nucleic acid can be integrated into the genome of the host cell or can be carried on an extra-chromosomal element. The host cell can be a yeast cell, insect cell, mammalian cell, avian cell, bacteria, Tetrahymena cells or combinations thereof.

The invention also relates to a method of using a parvovirus virus like particle (VLP) that contains VP1 and VP2, produced according to the method described herein for therapeutic and diagnostic purposes, for example as an antigen in a diagnostic kit.

BRIEF DESCRIPTION OF THE DRAWINGS

FIG. 1 is a diagram of yeast expression vector pBS24.1. This vector is suitable to produce VLPs in *S. cerevisiae.*

FIG. 2 is a diagram of a bicistronic yeast expression vector pCDC.7, based on pBS24.1. This vector is suitable for co-expression of parvovirus B19 VP1 and VP2 VLPs in *S. cerevisiae.*

FIGS. 3A-3D show the nucleotide sequence (SEQ ID NO: 16) of pCDC.7 used for co-expression of parvovirus B19 VP1 and VP2 VLP's in *S. cerevisiae.*

FIG. 4 shows the nucleotide sequence (SEQ ID NO: 17) of the optimized parvovirus B19 VP1.

FIG. 5 shows the nucleotide sequence (SEQ ID NO: 18) of the optimized parvovirus B19 VP2.

FIG. 6 shows the nucleotide sequence (SEQ ID NO: 19) of the ADH2/GAPDH promoter (as BamHI/HindIII fragment) used in the expression of parvovirus B19 VP2.

FIG. 7 shows the nucleotide sequence (SEQ ID NO: 20) of the "delta As" version of the ADH2/GAPDH promoter in which ten bases of GAPDH sequence has been replaced with 14 bases of parvovirus B19 native viral sequence (underlined) as it naturally occurs immediately upstream from the initiating methionine of VP1 (bold).

FIG. 8 shows the nucleotide sequence (SEQ ID NO: 21) of the ADH2/GAPDH promoter (as BamHI/MluI fragment) with TATA deletion used in the expression of parvovirus B19 VP1.

FIG. 9 shows the nucleotide sequence (SEQ ID NO: 22) of parvovirus B19 VP1 with 1SS (synthetic start-stop sequence, underlined) upstream from the junction between the ADH2/GAPDH promoter and the initiating methionine of VP1 (bold).

FIG. 10 shows the variation in relative amounts of soluble VP1 and soluble VP2 produced in yeast on a Western blot using antibodies to VP2. The upper band represents VP1 and the lower, darker band represents VP2. The labels describe what is in the plasmid or the type of modification that has been made. For example, lane 7 shows that one start/stop decreases the level of VP1 relative to VP2, and lane 8 shows two start/stops decrease the level even more.

FIG. 11 shows (A) Coomassie gels representing purified parvovirus B19 VLP and (B) electron micrographs of parvovirus B19 VLPs.

FIG. 12 shows three graphs that represent ELISA data which demonstrate the immunogenicity of parvovirus B19 VLPs. Highest titers were demonstrated with the MF59™ formulations and were similar for each dose concentration.

FIG. 13 is a diagram of a VP1 delta TATA/VP2 construct. This construct is suitable for use in the protein purification and experiments described in this application.

FIG. 14 shows the amino acid sequences of parvovirus B19 VP1 (SEQ ID NO: 23) and VP2 (SEQ ID NO: 24). VP1 is 781 amino acids long, and has a molecular weight of 84 kDa. VP2 is 554 amino acids long and has a molecular weight of 58 kDa.

FIG. 15 shows (A) SDS-PAGE and (B) Western of the sucrose shelf fractions from VP1/VP2 VLP expression.

FIG. 16 shows a (A) Coomassie stained SDS-PAGE and (B) α-VP1/VP2 antibody probed Western (B) analysis of fractions from a Capto Q elution of parvovirus B19 VP1/VP2 VLPs.

FIG. 17 shows a size exclusion chromatography (SEC) (S-200) chromatogram of purified VP1/VP2 VLPs.

DETAILED DESCRIPTION OF THE INVENTION

The present invention is, in part, based on the discovery that although parvovirus B19 VP1 and VP2 can be expressed in the same host cell to produce VLPs that contain both proteins, production of VLPs is inefficient. It has now been discovered that when VP1 and VP2 are expressed in the same host cell (e.g., a yeast cell), the expression of VP1 suppresses the expression of VP2 and the formation of VLPs. This results in inefficient VLP formation, and production of increased amount of insoluble material.

The present invention provides a solution to the problem of inefficient production of VLPs that contain parvovirus VP1 and VP2 proteins. The method provides a better way to produce VLPs that contain parvovirus VP1 and VP2 proteins by producing VP1 and VP2 in a host cell, such that VP1 is produced in lower abundance relative to VP2. Preferably, soluble VP1 is produced in lower abundance than soluble VP2. The invention provides recombinant nucleic acids that encode VP1 and VP2 and drive expression of the proteins in host cells in desired amounts. For example, the expression of VP1 and VP2 can be controlled by separate promoters, allowing for controlled expression of each protein at desired ratios. The invention also provides methods for producing parvovirus VLPs that contain VP1 and VP2 using host cells that contain the recombinant nucleic acids. These methods provide improved VLP production efficiency and reduce the variability and quality control issues associated with the prior methods that used separate vectors for expression of VP1 and VP2, and mixed them together to produce host cells, including variability in transfection efficiency (e.g., cell to cell variability and batch to batch variability), variability in the expression of VP1 relative to VP2, and suppression of VP2 expression by VP1.

Other aspects of the present invention include recombinant nucleic acids, host cells, methods for producing VLPs and immunogenic compositions that contain VLPs.

I. Definitions

All scientific and technical terms used in this application have meanings commonly used in the art unless otherwise specified. As used in this application, the following words or phrases have the meanings specified.

It must be noted that, as used in this specification and the appended claims, the singular forms "a", "an" and "the" include plural references unless the content clearly dictates otherwise. Thus, for example, reference to "a polynucleotide" includes a mixture of two or more such polynucleotides, and the like.

The term "about" in relation to a numerical value x means, for example, x+10%.

As used herein, the terms "parvovirus" refers to all parvoviruses associated with mammalian species (e.g., human, canine, chicken, feline, murine, porcine, raccoon, mink, kilham rat, lapine) and broadly to all genus of the Parvoviridae family (i.e., Parvovirus (e.g., canine parvovirus), Dependovirus (e.g., adeno-associated virus), Erythrovirus (e.g., parvovirus B19) and Bocavirus). Preferably, the parvovirus infects humans, i.e., is of the Dependovirus, Erythrovirus, or Bocavirus genus. Most preferably, the parvovirus is parvovirus B19. In some embodiments, the parvovirus is from the Parvovirus genus. The term parvovirus also includes isolates not characterized at the time of filing.

The parvovirus B19 species is subdivided into three distinct genotypes (Gallinella et al., 2003; Hokynar et al., 2002; Nguyen et al. 2002; Servant et al. 2002). The nucleotide divergency between the genotypes is approximately 10% and in the promoter region more than 20%. All viruses previously known as B19V were classified as genotype 1. Genotype 2 is found relatively infrequently. When genotype 2 is found, it is identified at a much higher frequency in individuals older than approximately 40 years of age. Genotype 3 viruses cluster into two subtypes represented by the protype strains V9 (Genbank accession no. AX003421) and D91.1 (Genbank accession no. AY083234) (Parsyan et al., 2007). Genotype 3 virus has been shown to be endemic in Ghana West Africa (Candotti et al., 2004) and may be present in a certain region of Brazil.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

"Substantially purified" generally refers to isolation of a substance (compound, polynucleotide, protein, polypeptide, polypeptide composition) such that the substance comprises the majority percent of the sample in which it resides. Typically in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

"Recombinant" as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

The term "transformation" refers to the insertion of an exogenous polynucleotide into a host cell, irrespective of the method used for the insertion. For example, direct uptake, transfection, transduction or f-mating are included. The exogenous polynucleotide may be maintained as a non-integrated vector, for example, a plasmid, or alternatively, may be integrated into the host genome.

"Recombinant host cells", "host cells," "cells", "cell lines," "cell cultures", and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence can be determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA or RNA, and even synthetic DNA sequences. A transcription termination sequence may be located 3' to the coding sequence.

Typical "control elements," include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

The term "nucleic acid" includes DNA and RNA, and also their analogs, such as those containing modified backbones (e.g. phosphorothioates, etc.), and also peptide nucleic acids (PNA), etc. The invention includes nucleic acids comprising sequences complementary to those described above (e.g. for antisense or probing purposes).

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Encoded by" refers to a nucleic acid sequence which codes for a polypeptide sequence, wherein the polypeptide sequence or a portion thereof contains an amino acid sequence of at least 3 amino acids.

"Expression cassette" or "expression construct" refers to an assembly which is capable of directing the expression of the sequence(s) or gene(s) of interest. An expression cassette generally includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

"Purified polynucleotide" refers to a polynucleotide of interest or fragment thereof which is essentially free, e.g., contains less than about 50%, preferably less than about 70%, and more preferably less than about at least 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as viral vectors.

As used herein, the term "epitope" generally refers to the site on an antigen which is recognised by a T-cell receptor and/or an antibody. Preferably it is a short peptide derived from or as part of a protein antigen. However the term is also intended to include peptides with glycopeptides and carbohydrate epitopes and protein surfaces comprised of peptides (with or without modifications, such as glycosylation) that are discontinuous in primary sequence but which are located in proximity to each other in the final folded structure. Several different epitopes may be carried by a single antigenic molecule. An epitope can be made from more than one molecule that associates covalently or non-covalently with one or more other molecules. The term "epitope" also includes modified sequences of amino acids or carbohydrates which stimulate responses which recognise the whole organism. It is advantageous if the selected epitope is an epitope of an infectious agent, which causes the infectious disease.

As used herein, the term "T cell epitope" refers generally to those features of a peptide structure which are capable of inducing a T cell response and a "B cell epitope" refers generally to those features of a peptide structure which are capable of inducing a B cell response.

An "immunological response" to an antigen or composition is the development in a subject of a humoral and/or a cellular immune response to an antigen present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

An immunogenic composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art.

See, e.g., Erickson et al., J. Immunol. (1993) 151:4189-4199; Doe et al., Eur. J. Immunol. (1994) 24:2369-2376. Recent methods of measuring cell-mediated immune response include measurement of intracellular cytokines or cytokine secretion by T-cell populations, or by measurement of epitope specific T-cells (e.g., by the tetramer technique) (reviewed by McMichael, A. J., and O'Callaghan, C. A., J. Exp. Med. 187(9)1367-1371, 1998; Mcheyzer-Williams, M. G., et al., Immunol. Rev. 150:5-21, 1996; Lalvani, A., et al., J. Exp. Med. 186:859-865, 1997).

Thus, an immunological response as used herein may be one that stimulates the production of antibodies (e.g., neutralizing antibodies that block bacterial toxins and pathogens such as viruses entering cells and replicating by binding to toxins and pathogens, typically protecting cells from infection and destruction). The antigen of interest may also elicit production of CTLs. Hence, an immunological response may include one or more of the following effects: the production of antibodies by B-cells; and/or the activation of suppressor T-cells and/or memory/effector T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art. (See, e.g., Montefiori et al. (1988) J Clin Microbiol. 26:231-235; Dreyer et al. (1999) AIDS Res Hum Retroviruses (1999) 15(17):1563-1571). The innate immune system of mammals also recognizes and responds to molecular features of pathogenic organisms via activation of Toll-like receptors and similar receptor molecules on immune cells. Upon activation of the innate immune system, various non-adaptive immune response cells. are activated to, e.g., produce various cytokines, lymphokines and chemokines Cells activated by an innate immune response include immature and mature dendritic cells of the moncyte and plamsacytoid lineage (MDC, PDC), as well as gamma, delta, alpha and beta T cells and B cells and the like. Thus, the present invention also contemplates an immune response wherein the immune response involves both an innate and adaptive response.

An "immunogenic composition" is a composition that comprises an antigenic molecule where administration of the composition to a subject results in the development in the subject of a humoral and/or a cellular immune response to the antigenic molecule of interest.

The terms "immunogenic" protein or polypeptide refer to an amino acid sequence which elicits an immunological response as described above. An "immunogenic" protein or polypeptide, as used herein, includes the full-length natural or recombinant sequence of the protein in question, including the precursor and mature forms, analogs thereof, or immunogenic fragments thereof.

A parvovirus polynucleotide, oligonucleotide, nucleic acid, protein, polypeptide, or peptide, as defined above, is a molecule derived from a parvovirus, respectively, including, without limitation, any of the various isolates of parvovirus. The molecule need not be physically derived from the particular isolate in question, but may be synthetically or recombinantly produced.

In particular, the parvovirus B19 genome contains three open reading frames: a non-structural 77 kDa protein, NS1, is encoded by nucleotides 436-2451; the minor structural protein, VP1 is encoded by nucleotides 2444-4787, and the major structural protein, VP2, is encoded by nucleotides 3125-4787 (Corcoran et al., *J. Med. Microb.*, 2004). Parvovirus B19 uses a single promoter, p6, which is capable of expressing structural and non-structural genes differentially (Blundell et al., 1987, Ozawa et al., 1987). Although the foregoing numbering is relative to the nucleotide sequence of the parvovirus B19 genome, it is to be understood that the corresponding positions in sequences obtained from other genotypes and isolates of parvovirus are also intended to be encompassed by the present invention. Any one of the nucleic acids encoding VP1 or VP2, as well as variants thereof, such as immunogenic fragments thereof, and polypeptides encoded by such nucleic acids can be used in the practice of the invention.

As used herein, the terms "minor structural protein" or "minor structural polypeptide" or "minor capsid protein" or "minor capsid polypeptide" or "VP1" in reference to a parvovirus refer to a polypeptide comprising a sequence homologous or identical to the ORF2-encoded polypeptide of a parvovirus, and includes sequences displaying at least about 80-100% sequence identity thereto, including any percent identity within these ranges, such as 81, 82, 83, 84, 85, 86, 87, 88, 89, 90, 91, 92, 93, 94, 95, 96, 97, 98, 99, 100% sequence identity thereto.

As used herein, the terms "major structural protein" or "major structural polypeptide" or "major capsid protein" or "major capsid polypeptide" or "VP2" in reference to a Parvovirus refer to a polypeptide comprising a sequence homologous or identical to the ORF3-encoded polypeptide of a Parvovirus, and include sequences displaying at least about 80-100% sequence identity thereto, including any percent identity within these ranges, such as 81, 82, 83, 84, 85, 86, 87, 88, 89, 90, 91, 92, 93, 94, 95, 96, 97, 98, 99, 100% sequence identity thereto.

As used herein, the term "virus-like particle" or "VLP" refers to a nonreplicating, noninfectious viral shell that contains a viral capsid but lacks all or part of the viral genome, in particular, the replicative components of the viral genome. VLPs are generally composed of one or more viral proteins, such as, but not limited to those proteins referred to as capsid, coat, shell, surface, structural proteins (e.g., VP1, VP2). Parvovirus VLPs can form spontaneously upon recombinant expression of VP2 in an appropriate expression system. Methods for producing particular VLPs are known in the art and discussed more fully below. The presence of VLPs following recombinant expression of viral proteins can be detected using conventional techniques known in the art, such as by electron microscopy, biophysical characterization, and the like. For example, VLPs can be isolated by density gradient centrifugation and/or identified by characteristic density banding. Alternatively, cryoelectron microscopy can be performed on vitrified aqueous samples of the VLP preparation in question, and images recorded under appropriate exposure conditions.

As used herein, a "biological sample" refers to a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components. In particular, parvovirus may be obtained from biological samples such as aerosol or respiratory secretions or blood from individuals infected with the viruses.

By "subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

By "therapeutically effective amount" in the context of the immunogenic compositions is meant an amount of an immunogen (e.g., immunogenic polypeptide, fusion protein, polyprotein, VLP, or nucleic acid encoding an antigen) which will induce an immunological response, either for antibody production or for treatment or prevention of parvovirus infection. Such a response will generally result in the development in the subject of an antibody-mediated and/or a secretory or cellular immune response to the composition. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell and/or γδT cell populations.

For purposes of the present invention, an "effective amount" of an adjuvant will be that amount which enhances an immunological response to a coadministered antigen or nucleic acid encoding an antigen.

As used herein, "treatment" refers to any of (i) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

II. Modes of Carrying out the Invention

Before describing the present invention in detail, it is to be understood that this invention is not limited to particularly exemplified molecules or process parameters as such may, of course, vary. It is also to be understood that the terminology used herein is for the purpose of describing particular embodiments of the invention only, and is not intended to be limiting. In addition, the practice of the present invention will employ, unless otherwise indicated, conventional methods of virology, microbiology, molecular biology, recombinant DNA techniques and immunology all of which are within the ordinary skill of the art. Such techniques are explained fully in the literature. See, e.g., Sambrook, et al., Molecular Cloning: A Laboratory Manual (3rd Edition, 2000); DNA Cloning: A Practical Approach, vol. I & II (D. Glover, ed.); Oligonucleotide Synthesis (N. Gait, ed., 1984); A Practical Guide to Molecular Cloning (1984); and Fundamental Virology, 4th Edition, 2001 (B. N. Fields and D. M. Knipe, eds.); Handbook of Experimental Immunology, Vols. I-IV (D. M. Weir and C. C. Blackwell eds., Blackwell Scientific Publications); A. L. Lehninger, Biochemistry (Worth Publishers, Inc., current edition); Methods In Enzymology (S. Colowick and N. Kaplan eds., Academic Press, Inc.). Although a number of methods and materials similar or equivalent to those described herein can be used in the practice of the present invention, the preferred materials and methods are described herein. In addition, all publications, patents and patent applications cited herein, whether supra or infra, are hereby incorporated by reference in their entireties.

A. Nucleic Acids

The invention relates to recombinant nucleic acid molecules that encode parvovirus VP1 and parvovirus VP2. The encoded VP1 and VP2 can be from any desired parvovirus, or any desired combination. Preferably, the encoded VP1 and VP2 are from a parvovirus that infects humans, i.e., a parvovirus of the Dependovirus, Erythrovirus, or Bocavirus genus. Most preferably, the parvovirus is parvovirus B19. In some aspects, the sequence that encodes VP1 and the sequence that encodes VP2, and their respective control elements, are on separate nucleic acid molecules, for example, on separate vectors. Preferably, the sequence that encodes VP1 and the sequence that encodes VP2, and their respective control elements, are components of a single nucleic acid molecule, such as a bicistronic vector.

The parvovirus VP1 and VP2 proteins can have the same or substantially the same amino acid sequence as the naturally occurring protein, such as the amino acid sequence of naturally occurring VP1 of parvovirus B19. If desired, in some embodiments, the amino acid sequence can differ from a naturally occurring sequence by one or more amino acid substitutions, additions and/or deletions. Preferably, less than about 10% or less than about 5% of the amino acid residues in VP1 or VP2 are substituted, added or deleted. Preferably, the amino acid sequence of the VP1 or VP2 protein is at least about 80%, at least about 85%, at least about 90%, at least about 95%, at least about 96%, at least about 97%, at least about 98%, or at least about 99% identical to a naturally occurring parvovirus VP1 or VP2 protein. Amino acid sequence variation is generally permitted in areas that are not conserved among VP1 or VP2 proteins, and therefore does not interfere with the ability of the proteins to form VLPs. If desired, mutations (e.g., amino acid substitutions, additions or deletions) can be introduced to alter certain functions, for example, VP1 can be mutated to inactivate its phospholipase activity. For example, the amino acid sequence of VP1 may contain a point mutation (e.g., His153Ala), or any of the mutations described in WO 06/032697, EP 1791858 or US 20070286870.

The recombinant nucleic acids of the invention provide independent regulation of transcription and/or translation of VP1 and VP2, so that when equivalent amounts of the sequence that encodes VP1 and the sequence that encodes VP2 are present in a suitable host cell, VP1 is expressed in lower abundance relative to VP2. Preferably, soluble VP1 is produced in lower abundance than soluble VP2. In some embodiments, the codon usage in the nucleotide sequence that encodes VP1 and in the nucleotide sequence that encodes VP2 are selected so that when equivalent amounts of the sequence that encodes VP1 and the sequence that encodes VP2 are present in a suitable host cell, VP1 is expressed in lower abundance relative to VP2. Preferably, soluble VP1 is produced in lower abundance than soluble VP2. This can be accomplished, for example, using a codon optimized nucleotide sequence that encodes VP2 and a nucleotide sequence that is not codon optimized, or that is codon deoptimized, that encodes VP1.

In other embodiments, the nucleotide sequence that encodes VP1 and the nucleotide sequence that encodes VP2 are operably linked to different control elements, so that when equivalent amounts of the sequence that encodes VP1 and the sequence that encodes VP2 are present in a suitable host cell, VP1 is expressed in lower abundance relative to VP2. Preferably, soluble VP1 is produced in lower abundance than soluble VP2. The control elements for VP1 and VP2 expression are selected so that VP1 is produced by the desired host cell in lower abundance than VP2 when equivalent amounts of sequences that encode VP1 and VP2 are present in the desired host cell. This is generally accomplished using control elements that affect transcription, translation, or transcription and translation of VP1 and VP2. For example, the nucleotide sequence encoding VP2 can be operably linked to a strong promoter, and the nucleotide sequence encoding VP1 can be operably linked to a weak promoter. The promoters used may be any promoters that allows for independent regulation of VP1 and VP2 expression. An exemplary strong promoter for expression in yeast is the ADH2/GAPDH promoter, which is incorporated into pBS24.1 (FIG. 1). An exemplary weak promoter for expression in yeast is the YPTI constitutively active promoter. See, Sears et al., Yeast 14:783-790 (1998). Other suitable strong and weak promoters for use in yeasts or other host cells are known in the art. For example, a strong promoter for expression in mammalian cells is the CMV promoter. An exemplary strong promoter for expression in bacteria is the recA promoter. An exemplary weak promoter for expression in bacteria is the araBAD promoter.

In some embodiments, a nucleotide sequence encoding VP2 is operably linked to a promoter suitable for expression in a desired host cell, and a nucleotide sequence encoding VP1 is operably linked to a variant of that promoter, such as an expression de-optimized variant. The variant promoter can be modified relative to the parental promoter in a variety of ways to reduce the expression of VP1 relative to VP2 (e.g., soluble VP1 is produced in lower abundance than soluble VP2). For example, the variant promoter can be modified by alteration of the sequence of, or deletion of a portion of, transcriptional elements upstream of the nucleic acid encoding VP1, such as alteration or deletion of all or a portion of the TATA box or the junction site, by introduction of one or more transcription start sites upstream of the nucleic acid encoding VP1, by introduction of one or more transcription stop sites upstream of the nucleic acid encoding VP1, or by any combination thereof. These functional portions of promoters are well-known in the art and can be readily identified and modified in any desired promoter. The recombinant nucleic acids can contain other regulatory elements, such as enhancer binding sites, ribosome binding sites, polyadenylation sites, inducible promoters, repressors, elements that affect RNA stability, siRNA, splice sites, and the like and deletions and alterations thereof, if desired, so that VP1 is produced by the desired host cell in lower abundance than VP2 when equivalent amounts of sequences that encode VP1 and VP2 are present in the desired host cell.

In some embodiments, the recombinant nucleic acid contains a nucleotide sequence that encodes VP2 that is operably linked to the ADH2/GAPDH promoter (FIG. 6, SEQ ID NO: 19), and a nucleotide sequence that encodes VP1 that is operably linked to a variant of the ADH2/GAPDH promoter that results in decreased expression of VP1 relative to VP2 (e.g., soluble VP1 is produced in lower abundance than soluble VP2). Examples of variant ADH2/GAPDH promoters that are suitable for use in the invention include variants in which one or more portions of the promoter (e.g., portions of about 1 to about 20 nt) are replaced with portions of the native parvovirus sequence, such as the "delta As" variant (FIG. 7, SEQ ID NO: 20), variants in which the TATA box is deleted or altered in whole or in part, such as the TATA deletion variant (FIG. 8, SEQ ID NO: 21), variants that contain one or more transcription start and/or stop sequences, such as the 1SS variant (FIG. 9, SEQ ID NO: 22), and promoters that contain any combination of these modifications. In other embodiments, a nucleotide sequence that encodes VP2 is codon optimized for expression in a desired host cell, and a nucleotide sequence that encodes VP1 is not codon optimized for expression in a desired host cell or is codon deoptimized, for example, through the use of non-preferred codons.

The expression control elements that control expression of VP1 and VP2 can be selected to produce any desired VP1:VP2 expression ratio (%:%) such as about 49:51, about 40:60, about 30:70, about 25:75, about 20:80, about 15:85, about 10:90, about 9:91, about 8:92, about 7:93, about 6:94, about 5:95, about 4:96, about 3:97, about 2:98, about 1:99, about 2:98 to about 20:80, about 5:95 to about 20:80, about 5:95 to about 15:85, or about 7:93 to about 12:88. Preferably, the expression ratio is the ratio of soluble VP1:soluble VP2.

Without wishing to be bound by any particular theory, it is believed that lowered VP1 expression relative to VP2 expression reduces VP1-mediated suppression of VP2 expression, assembly and/or stability and results in more efficient production and higher yield of VLPs that contain VP1 and VP2.

A nucleic acid encoding a parvovirus protein can be constructed using any suitable method (e.g. by chemical synthesis, using recombinant DNA technology) and can take various forms (e.g. single-stranded, double-stranded, vectors, etc.). Many suitable methods for producing recombinant constructs are well-known and conventional in the art. For example, the recombinant nucleic acids can be produced from two or more oligonucleotides comprising sequences encoding portions of the VP1 or VP2 protein or by ligating oligonucleotides to form a coding sequence for the full-length VP1 or VP2 protein using standard molecular biology techniques. See, e.g., U.S. Pat. Nos. 6,632,601 and 6,630,298. Preferably, nucleic acids are prepared in substantially pure form (i.e. substantially free from other host cell or non host cell nucleic acids).

Polynucleotides that encode VP1 and/or VP2 proteins of interest can be isolated from a genomic library derived from viral RNA, present in, for example, respiratory secretions or blood from an infected individual. Alternatively, parvovirus nucleic acids can be isolated from infected humans or other mammals or from respiratory secretions or blood collected from infected individuals. An amplification method such as PCR can be used to amplify polynucleotides from either parvovirus genomic RNA or cDNA encoding parvovirus. Alternatively, polynucleotides can be chemically synthesized. The nucleotide sequence can be designed with the appropriate codons for the particular amino acid sequence desired. Preferably, synthetic constructs will contain codons optimized for expression in the intended host cell in which the VP2 or VP1/VP2 protein will be produced. The complete sequence of the polynucleotide of interest can be assembled from overlapping oligonucleotides prepared by standard methods and assembled into a complete coding sequence. See, e.g., Edge (1981) Nature 292:756; Nambair et al. (1984) Science 223:1299; Jay et al. (1984) J. Biol. Chem. 259:6311; Stemmer et al. (1995) Gene 164:49-53. The polynucleotides can be RNA or single- or double-stranded DNA. Preferably, the polynucleotides are isolated free of other components, such as proteins and lipids.

Alternatively, particular nucleotide sequences can be obtained from vectors harboring the desired sequences or synthesized completely or in part using various oligonucleotide synthesis techniques known in the art, such as site-directed mutagenesis and polymerase chain reaction (PCR) techniques where appropriate. See, e.g., Sambrook, supra. In particular, one method of obtaining nucleotide sequences encoding the desired amino acid sequences is by annealing complementary sets of overlapping synthetic oligonucleotides, followed by ligation with an appropriate DNA ligase and amplification of the ligated nucleotide sequence via PCR. See, e.g., Jayaraman et al. (1991) *Proc. Natl. Acad. Sci. USA* 88:4084-4088. Additionally, oligonucleotide directed synthesis (Jones et al. (1986) *Nature* 54:75-82), oligonucleotide directed mutagenesis of pre-existing nucleotide regions (Riechmann et al. (1988) *Nature* 332:323-327 and Verhoeyen et al. (1988) *Science* 239:1534-1536), and enzymatic filling-in of gapped oligonucleotides using T4 DNA polymerase (Queen et al. (1989) *Proc. Natl. Acad. Sci. USA* 86:10029-10033) can be used.

Recombinant constructs encoding VP1 and/or VP2 proteins can be prepared in suitable vectors, such as expression vectors, using conventional methods. Preferred recombinant constructs, such as an expression vector, include a nucleic acid sequence which encodes a parvovirus VP1 protein and a nucleic acid sequence which encodes a parvovirus VP2 protein. The recombinant construct can be in the form of DNA, RNA, or a combination of RNA and DNA and can be either single or double stranded. For example, the construct can be in the form of a plasmid, linear DNA or RNA, mRNA, self replicating RNA (e.g., an alpha virus-based replicon), and the like.

A number of suitable vectors for expression of recombinant proteins in a desired host cell are well-known and conventional in the art. Suitable vectors can contain a number of components, including, but not limited to one or more of the following: an origin of replication; a selectable marker gene; one or more expression control elements, such as a transcriptional control element (e.g., a promoter, an enhancer, a terminator), and/or one or more translation signals; and a signal sequence or leader sequence for targeting to the secretory pathway in a selected host cell (e.g., of mammalian origin or from a heterologous mammalian or non-mammalian species). For example, for expression in insect cells a suitable baculovirus expression vector, such as pFastBac (Invitrogen), can be used to produce recombinant baculovirus particles. The baculovirus particles are amplified and used to infect insect cells to express recombinant protein. For expression in mammalian cells, a vector that will drive expression of the construct in the desired mammalian host cell (e.g., Chinese hamster ovary cells) is used. Similarly, for expression in yeast, a vector that will drive expression in the desired yeast host cell (e.g., *Saccharomyces cerevisiae, Candida albicans, Candida maltosa, Hansenual polymorphs, Kluyveromyces fragilis, Kluyveromyces lactis, Pichia guillerimondii, Pichia pastoris, Schizosaccharomyces pombe* and *Yarrowia lipolytica*) is used.

Viral vectors can be used for the production of VLPs of the invention in eukaryotic cells, such as those derived from the pox family of viruses, including vaccinia virus and avian poxvirus. Additionally, a vaccinia based infection/transfection system, as described in Tomei et al., *J. Virol.* (1993) 67:4017-4026 and Selby et al., *J. Gen. Virol.* (1993) 74:1103-1113, will also find use with the present invention. In this system, cells are first infected in vitro with a recombinant vaccinia virus that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the recombinant vaccinia virus transcribes the transfected DNA into RNA which is then translated into protein by the host translational machinery. Alternately, T7 can be added as a purified protein or enzyme as in the "progenitor" system (Studier and Moffatt, *J. Mol. Biol.* (1986) 189:113-130). The method provides for high level, transient, cytoplasmic production of large quantities of RNA and its translation product(s).

A recombinant nucleic acid may comprise a first nucleic acid sequence encoding parvovirus B19 VP1 protein and a second nucleic acid sequence encoding parvovirus B19 VP2 protein, wherein each nucleic acid sequence is controlled by a separate promoter. The parvovirus B19 VP1 and VP2 proteins and their respective control sequences can appear in any desired orientation or order in the recombinant nucleic acid (e.g., plasmid), and are not limited by the language "first nucleic acid" and "second nucleic acid" as used herein.

The recombinant nucleic acid may be a plasmid that comprises a modification that transcriptionally and/or translationally decrease expression of parvovirus B19 VP1 relative to Parvovirus B19 VP2. A modification may be deletion or alteration of the sequence of all or a portion of the TATA box, deletion or alteration of the sequence of a junction site upstream of the nucleic acid encoding parvovirus B19 VP1, introduction of one or more transcription start and/or stop sites upstream of the nucleic acid encoding parvovirus B19 VP1, or any combination of these modifications. For example, the modification may be deletion of a portion of the TATA box and deletion of a junction site upstream of the nucleic acid encoding parvovirus B19 VP1, or the modification may be introduction of two or more transcription start and/or stop sites upstream of the nucleic acid encoding parvovirus B 19 VP1.

If desired, the recombinant nucleic acid may be a vector that can include a detectable marker. For example, the detectable marker can be a polypeptide that confers resistance to one or more antibiotics.

B. Host Cells

The invention provides recombinant host cells that contain a recombinant nucleic acid molecule, as described herein, that encode parvovirus VP1 and parvovirus VP2. In some embodiments, the nucleotide sequence that encodes VP1 and the nucleotide sequence that encodes VP2, and their respective control elements, are on separate nucleic acid molecules, for example, on separate vectors. In these embodiments, the host cell contains two different recombinant nucleic acid molecules. Preferably, the host cell contains substantially equal amounts of the nucleotide sequence that encodes VP1 and the nucleotide sequence that encodes VP2 (e.g., substantially equal amounts of two different recombinant nucleic acids). More preferably, the nucleotide sequence that encodes VP1, the nucleotide sequence that encodes VP2, and their respective control elements, are components of a single nucleic acid molecule, such as a bicistronic vector. In these embodiments, the host cell contains a single recombinant nucleic acid molecule, which may be present in multiple copies.

The recombinant host cells can contain any of the nucleic acid molecules described herein. Suitable host cells include, for example, yeast cells (e.g., *Saccharomyces cerevisiae, Candida albicans, Candida maltosa, Hansenual polymorphs, Kluyveromyces fragilis, Kluyveromyces lactis, Pichia guillerimondii, Pichia pastoris, Schizosaccharomyces pombe* and *Yarrowia lipolytica*), insect cells (e.g., *Aedes aegypti, Autographa californica, Bombyx mori, Drosophila melanogaster, Spodoptera frugiperda*, and *Trichoplusia ni*), mammalian cells (e.g., human, non-human primate, horse, cow, sheep, dog, cat, and rodent (e.g., hamster), avian cells (e.g., chicken, duck, and geese, bacteria (e.g., *E. coli, Bacillus subtilis*, and *Streptococcus* spp.), Tetrahymena cells (e.g., *Tetrahymena thermophila*) or combinations thereof. Suitable yeast strains include, for example, the AD2, JSC310, AD3 and AD4 strains of *S. cerevisiae*.

Many suitable insect cells and mammalian cells are well-known in the art. Suitable insect cells include, for example, Sf9 cells, Sf21 cells, Tn5 cells, Schneider S2 cells, and High Five cells (a clonal isolate derived from the parental *Trichoplusia ni* BTI-TN-5B1-4 cell line (Invitrogen)). Suitable mammalian cells include, for example, Chinese hamster ovary (CHO) cells, human embryonic kidney cells (HEK293 cells, typically transformed by sheared adenovirus type 5 DNA), NIH-3T3 cells, 293-T cells, Vero cells, HeLa cells, PERC.6 cells (ECACC deposit number 96022940), Hep G2 cells, MRC-5 (ATCC CCL-171), WI-38 (ATCC CCL-75), fetal rhesus lung cells (ATCC CL-160), Madin-Darby bovine kidney ("MDBK") cells, Madin-Darby canine kidney ("MDCK") cells (e.g., MDCK (NBL2), ATCC CCL34; or MDCK 33016, DSM ACC 2219), baby hamster kidney (BHK) cells, such as BHK21-F, HKCC cells, and the like. Suitable avian cells include, for example, chicken embryonic stem cells (e.g., EBx® cells), chicken embryonic fibroblasts, chicken embryonic germ cells, duck cells (e.g., AGE1.CR and AGE1.CR.pIX cell lines (ProBioGen) which are described, for example, in *Vaccine* 27:4975-4982 (2009) and WO2005/042728), EB66 cells, and the like.

Suitable insect cell expression systems, such as baculovirus systems, are known to those of skill in the art and described in, e.g., Summers and Smith, *Texas Agricultural Experiment Station Bulletin* No. 1555 (1987). Materials and methods for baculovirus/insect cell expression systems are commercially available in kit form from, inter alia, Invitrogen, San Diego Calif. Avian cell expression systems are also known to those of skill in the art and described in, e.g., U.S. Pat. Nos. 5,340,740; 5,656,479; 5,830,510; 6,114,168; and 6,500,668; European Patent No. EP 0787180B; European Patent Application No. EP03291813.8; WO 03/043415; and WO 03/076601. Similarly, yeast, bacterial and mammalian cell expression systems are also known in the art and described in, e.g., *Yeast Genetic Engineering* (Barr et al., eds., 1989) Butterworths, London.

C. Production of Virus-like Particles (VLPs)

The invention provides a process for producing a parvovirus VLP that contains VP1 and VP2. The VLP can contain VP1 and VP2 from any desired parvovirus, or any desired combination. As described herein, the VP1 and VP2 proteins can have an amino acid sequence that is the same as or substantially the same as a naturally occurring parvovirus VP1 or VP2, or can contain one or more amino acid substitutions, deletions or additions. For example, VP1 can be mutated to inactivate its phospholipase activity. For example, the amino acid sequence of VP1 may contain a point mutation (e.g., His153Ala), or any of the mutations described in WO 06/032697, EP 1791858 or US 20070286870. Preferably, the VLP contains VP1 and VP2 are from a parvovirus that infects humans, i.e., a parvovirus of the Dependovirus, Erythrovirus, or Bocavirus genus. Most preferably, the VLP contains parvovirus B19 VP1 and parvovirus B19 VP2. The process includes maintaining a host cell that produces VP1 and VP2, as described herein, under conditions whereby the VP1 and VP2 proteins encoded by the recombinant nucleic acid are produced and assembled into VLPs that contain VP1 and VP2. In the method of the invention, VP1 is produced by the host cell in lower abundance relative to VP2. Preferably, soluble VP1 is produced in lower abundance than soluble VP2. Optionally, the process further includes isolating or purifying the VLPs from the culture media, from a cell lysate or homogenate, or from any combination thereof.

In some aspects, the method comprises culturing a host cell that contains a recombinant nucleic acid that encodes VP1 and VP2 protein under conditions suitable for expression of VP1 and VP2 and self-assembly of VP1 and VP2 to form VLPs. Conditions suitable for the formation of VLPs are well-known and can be easily determined by a person of ordinary skill in the art. See, e.g., U.S. Pat. No. 7,527,801, which describes the production of viral particles in yeast cells (*Saccharomyces cerevisiae*) and insect cells (SF9), and Taube, S. et al, *Archives of Virology*, 150:1425-1431 (2005), which describes the production of VLPs in HEK293T cells. If desired, the method can further include the step of isolating or purifying the parvovirus VLP from the culture media, cells (e.g., from a cell lysate or homogenate) or a combination thereof. In some preferred embodiments, the host cell used to produce the VLPs are yeast cells, mammalian cells, insect cell, or combinations thereof, and the host cells produce less VP1 relative to VP2.

As described herein, the host cells produce VP1 in lower abundance relative to VP2 (e.g., soluble VP1 is produced in lower abundance than soluble VP2), as a result of the individual control elements that are operably linked to the nucleic acids that encode VP1 and VP2 and/or as a result of other features of the recombinant nucleic acids that encode VP1 and VP2, such as optimized codon usage and deoptimized codon usage. Such control elements (e.g., promoters) and features (e.g., codon usage) allow for the relative production of VP1 and VP2 to be controlled. Any suitable host cell that permits VP1 to be produced in lower abundance than VP2 can be used in the method. For example, yeast cells (e.g., *Saccharomyces cerevisiae, Candida albicans, Candida maltosa, Hansenual polymorphs, Kluyveromyces fragilis, Kluyveromyces lactis, Pichia guillerimondii, Pichia pastoris, Schizosaccharomyces pombe* and *Yarrowia lipolytica*), insect cells (e.g., *Aedes aegypti, Autographa californica, Bombyx mori, Drosophila melanogaster, Spodoptera frugiperda,* and *Trichoplusia ni*), mammalian cells (e.g., human, non-human primate, horse, cow, sheep, dog, cat, and rodent (e.g., hamster), avian cells (e.g., chicken, duck, and geese, bacteria (e.g., *E. coli, Bacillus subtilis,* and *Streptococcus* spp.), Tetrahymena cells (e.g., Tetrahymena thermophile) or combinations thereof, can be used. Suitable methods for maintaining such host cells to permit expression of recombinant nucleic acids, including small scale and large scale culture conditions, are known in the art. In some embodiments, the host cell is a yeast cell, mammalian cell or insect cell. In more particular embodiments, the host cell is a yeast cell, such as the *S. cerevisiae* strain AD2, JSC310, AD3, AD4 or combinations thereof.

In some embodiments, the provided host cell contains two different recombinant nucleic acid molecules, one that encodes VP1 and one that encodes VP2. In other embodiments the provided host cell contains a single recombinant nucleic acid molecule (which may be present in multiple copies) that includes a sequence that encodes VP1, a sequence that encodes VP2, and their respective control elements. For example, in these embodiments, the recombinant nucleic acid can be a bicistronic vector in which a nucleotide sequence that encodes VP1 is operably linked to a first control sequence, and a nucleotide sequence that encodes VP2 is operably linked to a second control sequence. For example, the nucleotide sequence encoding VP2 can be operably linked to a strong promoter, and the nucleotide sequence encoding VP1 can be operably linked to a weak promoter. An exemplary strong promoter for expression in yeast is the ADH2/GAPDH promoter, which is incorporated into pBS24.1 (FIG. 1). An exemplary weak promoter for expression in yeast is the YPTI constitutively active promoter. See, Sears et al., *Yeast* 14:783-790 (1998).

Other suitable strong and weak promoters for use in yeasts or other host cells are known in the art. The promoters used may be any promoters that allow for independent regulation of VP1 and VP2 expression.

In some embodiments, the host cell contains a recombinant nucleic acid in which a nucleotide sequence encoding VP2 is operably linked to a promoter suitable for expression in a desired host cell, and a nucleotide sequence encoding VP1 is operably linked to a variant of that promoter, such as an expression de-optimized variant. The variant promoter can be modified relative to the parental promoter in a variety of ways to reduce the expression of VP1 relative to VP2 (e.g, soluble VP1 is produced in lower abundance than soluble VP2). For example, the variant promoter can be modified by deletion of a portion of transcriptional elements upstream of the nucleic acid encoding VP1, such as deletion or alteration of the sequence of all or a portion of the TATA box, the junction site, by introduction of one or more transcription start sites upstream of the nucleic acid encoding VP1, by introduction of one or more transcription stop sites upstream of the nucleic acid encoding VP1, by any combination thereof. These functional portions of promoters are well-known in the art and can be readily identified and modified in any desired promoter. The recombinant nucleic acids can contain other regulatory elements, such as enhancer binding sites, ribosome binding sites, polyadenylation sites, and the like and deletions and alterations thereof, if desired, so that VP1 is produced by the desired host cell in lower abundance than VP2 when equivalent amounts of sequences that encode VP1 and VP2 are present in the desired host cell.

In some embodiments, the host cell comprises a recombinant nucleic acid that contains a nucleotide sequence that encodes VP2 that is operably linked to the ADH2/GAPDH promoter (FIG. 6, SEQ ID NO: 19), and a nucleotide sequence that encodes VP1 that is operably linked to a variant of the ADH2/GAPDH promoter that results in decreased expression of VP1 relative to VP2. Examples of variant ADH2/GAPDH promoters that are suitable for use in the invention include variants in which one or more portions of the promoter (e.g., portions of about 1 to about 20 bases) are replaced with portions of the native parvovirus sequence, such as the "delta As" variant (FIG. 7, SEQ ID NO: 20), variants in which the TATA box is deleted or altered in whole or in part, such as the TATA deletion variant (FIG. 8, SEQ ID NO: 21), variants that contain one or more transcription start and/or stop sequences, such as the 1SS variant (FIG. 9, SEQ ID NO: 22), and promoters that contain any combination of these modifications. In other embodiments, the host cell comprises a recombinant nucleic acid that contains a nucleotide sequence encoding VP2 that is codon optimized for expression is a desired host cell, and a nucleotide sequence encoding VP1 that is not codon optimized for expression is a desired host cell or is codon deoptimized, for example, through the use of non-preferred codons.

The host cell provided can contain a recombinant nucleic acid in which the expression control elements that control expression of VP1 and VP2 are selected to produce any desired VP1:VP2 expression ratio. For example, the host cell can produce VP1 and VP2 with a VP1:VP2 expression ratio (%:%) of about 49:51, about 40:60, about 30:70, about 25:75, about 20:80, about 15:85, about 10:90, about 9:91, about 8:92, about 7:93, about 6:94, about 5:95, about 4:96, about 3:97, about 2:98, about 1:99, about 2:98 to about 20:80, about 5:95 to about 20:80, about 5:95 to about 15:85, or about 7:93 to about 12:88. Preferably, the expression ratio is the ratio of soluble VP1:soluble VP2.

In particular embodiments of the method, the host cell comprises an expression vector that encodes VP1 and VP2, preferably parvovirus B19 VP1 and parvovirus B19 VP2. For example, the expression vector can be a plasmid comprising a regulatory element that is operably linked to a nucleotide sequence encoding VP2, and a variant of that regulatory element that is operably linked to a nucleotide sequence encoding VP1. The variant regulatory element transcriptionally, translationally or transcriptionally and translationally decreases expression of VP1 relative to VP2. The variant regulatory element may, for example, have a portion of the TATA box sequence altered or deleted, a portion of the junction site upstream of the VP1 gene deleted, or a combination thereof. The variant regulatory element may alternatively or in addition contain one or more introduced transcription start/stop sites upstream of the VP1 coding sequence. Such variant regulatory elements, and others described herein, allow for the efficient production of VP1/VP2 VLPs. When a variant regulatory element is operably linked to the nucleotide sequence that encodes VP1, the variant regulatory element can contain any one or more of the particular modifications described herein in any desired combination, (e.g., deletion or alteration of all or a portion of the TATA box sequence, deletion or alteration of all or a portion of the A-rich junction region, introduction of one or more transcription start sites and/or transcription stop sites upstream of the VP1 coding sequence, and any combinations thereof). For example, the variant regulatory element is operably linked to the nucleotide sequence that encodes VP1 can include i) deletion or alteration of all or a portion of the TATA box sequence and deletion or alteration of all or a portion of the A-rich junction region; ii) deletion or alteration of all or a portion of the TATA box sequence and one or more introduced transcription start sites and/or transcription stop sites upstream of the VP1 coding sequence; or iii) deletion or alteration of all or a portion of the A-rich junction region and one or more introduced transcription start sites and/or transcription stop sites upstream of the VP1 coding sequence.

In some aspects, the method further comprises isolating or purifying the VLPs from host cell culture media (e.g., conditioned media), host cells (e.g., cell lysate, cell homogenate) or a combination thereof. Preferably, the VLPs are isolated or purified directly from the host cell culture media, i.e., conditioned culture media. However, if desired, the host cells can be recovered, for example by centrifugation, a host cell homogenate or lysate can be formed using any suitable methods, and VLPs can be isolated from the homogenate or lysate. Suitable chemical, physical or mechanical methods that can be used to lyse cells but keep VLPs substantially intact are known in the art and are described in, e.g., *Protein Purification Applications: A Practical Approach*, (E. L. V. Harris and S. Angal, Eds., 1990).

VLPs can be isolated from culture media or host cells, e.g., a cell lysate or homogenate, using any suitable method. Suitable methods that maintain the integrity of VLPs, such as, density gradient centrifugation, e.g., sucrose gradients, PEG-precipitation, pelleting, and the like (see, e.g., Kirnbauer et al. *J. Virol*. (1993) 67:6929-6936), as well as standard purification techniques including chromatography, e.g., ion exchange and gel filtration chromatograph, can be used. Centrifugation, on a sucrose cushion or sucrose gradient is a convenient method for isolating VLPs from VP1 and VP2 monomers or oligomers and from other cellular components. These methods can be used singly, consecutively or integrated into a larger purification scheme. For example, VLPs that are purified on a sucrose cushion or gradient can then be further purified if desired, for example, using ion exchange chromatography, size exclusion chromatography, filtration techniques or any other suitable method.

In one embodiment, the invention provides a method of isolating parvovirus VLPs from host cells, comprising preparing a host cell lysate or homogenate; separating said VLPs from the host cell lysate or homogenate using any suitable method; and further purifying said VLPs. The purification of the VLPs according to this aspect of the invention can, for example, include purification through a sucrose gradient.

The present invention further provides VLPs made using the methods described herein. In some embodiments, the method comprises culturing a host cell that contains a recombinant nucleic acid that encodes VP1 and VP2 protein under conditions suitable for expression of VP1 and VP2 and self-assembly of VP1 and VP2 to form VLPs. If desired, the method can further comprise isolating or purifying the VLPs from host cell culture media (e.g., conditioned media), host cells (e.g., cell lysate, cell homogenate) or a combination thereof.

D. Immunogenic Composition

The invention also provides immunogenic compositions comprising a parvovirus VLP that contains VP1 and VP2 produced by the methods described herein, and immunogenic compositions that contain a recombinant nucleic acid that encodes parvovirus VP1 and VP2 as described herein.

The immunogenic compositions may comprise a single type of VLP or a mixture of two or more different VLPs and one or more additional antigens, if desired. Antigens may be administered individually or in combination, in e.g., prophylactic (i.e., to prevent infection) or therapeutic (to treat infection) immunogenic compositions. The immunogenic composition may be given more than once (e.g., a "prime" administration followed by one or more "boosts") to achieve the desired effects. The same composition can be administered in one or more priming and one or more boosting steps. Alternatively, different compositions can be used for priming and boosting. For example, a nucleic acid composition can be administered for priming and a VLP composition can be administered for boosting, or vise versa.

In the immunogenic compositions that contain a recombinant nucleic acid that encodes parvovirus VP1 and VP2, the recombinant nucleic acid can be any recombinant nucleic acid described herein, for example, linear DNA or RNA, plasmid DNA, mRNA, self replicating RNA and the like. If desired, the nucleic acid can contain one or more modified bases to improve stability and/or resistance to nuclease degradation. If desired, the immunogenic nucleic acid can also include one or more components to facilitate uptake of the nucleic acid by cells and/or reduce nuclease degradation, such as, cationic microparticles or nanoparticles, cationic lipids and the like.

The immunogenic compositions generally include one or more "pharmaceutically acceptable excipients or vehicles" such as water, saline, glycerol, ethanol, and the like singly or in combination. Immunogenic compositions will typically, in addition to the components mentioned above, comprise one or more "pharmaceutically acceptable carriers." These include any carrier which does not itself induce the production of antibodies harmful to the individual receiving the composition. Suitable carriers typically are large, slowly metabolized macromolecules such as proteins, polysaccharides, polylactic acids, polyglycolic acids, polymeric amino acids, amino acid copolymers, and lipid aggregates (such as oil droplets or liposomes). Such carriers are well known to those of ordinary skill in the art. Additionally, an auxiliary substance, such as a wetting or emulsifying agent, pH buffering substance, and the like, may be present. A thorough discussion of pharmaceutically acceptable components is available in Gennaro (2000) Remington: *The Science and Practice of Pharmacy*. 20th Ed., ISBN: 0683306472.

Pharmaceutically acceptable salts can also be used in immunogenic compositions of the invention, for example, mineral salts such as hydrochlorides, hydrobromides, phosphates, or sulfates, as well as salts of organic acids such as acetates, proprionates, malonates, or benzoates.

If desired, antigens can be adsorbed to, entrapped within or otherwise associated with liposomes and particulate carriers such as poly(D,L-lactide co-glycolide) (PLG) microparticles or nanoparticles. Antigens can be conjugated to a carrier protein in order to enhance immunogenicity. See Ramsay et al. (2001) Lancet 357(9251):195-196; Lindberg (1999) Vaccine 17 Suppl 2:S28-36; Buttery & Moxon (2000) J R Coll Physicians Lond 34:163-168; Ahmad & Chapnick (1999) Infect Dis Clin North Am 13:113-133, vii; Goldblatt (1998) J. Med. Microbiol. 47:563-567; European patent 0 477 508; U.S. Pat. No. 5,306,492; WO98/42721; Conjugate Vaccines (eds. Cruse et al.) ISBN 3805549326, particularly vol. 10:48-114; Hermanson (1996) Bioconjugate Techniques ISBN: 0123423368 or 012342335X.

Immunogenic compositions of the present invention may be administered in conjunction with other immunoregulatory agents. For example, an immunogenic composition of the invention can include an adjuvant. Preferred adjuvants include, but are not limited to, one or more of the following types of adjuvants described below. Immunogenic compositions of the present invention may also be pre-mixed with an adjuvant before administration.

In one embodiment, an immunogenic composition comprises a parvovirus B19 VLP (e.g., 0.05, 0.5, 5 µg protein/ml) and a MF59C™.1 adjuvant, wherein 50% of the final volume is MF59C™.1 adjuvant. In a specific embodiment an immunogenic composition comprises 0.8 mg/ml of parvovirus B19 VLP and MF59C™.1 as an adjuvant, at a final volume of 1:1.

Alum

In one embodiment, the adjuvant for use in the present invention is alum (aluminum potassium sulfate (AlK(SO$_4$)$_2$)), or an alum derivative, such as that formed in-situ by mixing an antigen in phosphate buffer with alum, followed by titration and precipitation with a base such as ammonium hydroxide or sodium hydroxide.

Retinoic Acid

In one embodiment, the adjuvant for use in the present invention is retinoic acid, the oxidized form of Vitamin A, with only partial vitamin A function.

MF59C™.1

In one embodiment, the adjuvant for use in the present invention is MF59C™.1, an oil-in-water emulsion (squalene) in citrate buffer. MF59C™.1 has been shown to be an effective adjuvant and enhance the production of high titers of neutralizing antibodies against parvovirus B19 (Ballou et al., JID, 187:675-678 (2003)).

Mineral-containing Compositions

Mineral containing compositions suitable for use as adjuvants in the invention include mineral salts, such as aluminum salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of *Vaccine Design* . . . (1995) eds. Powell & Newman. ISBN: 030644867X. Plenum.], or mixtures of different mineral compounds, with the compounds taking any suitable form (e.g. gel, crystalline, amorphous, etc.), and with adsorption being preferred. The mineral containing compositions may also be formulated as a particle of metal salt.

The adjuvants known as "aluminium hydroxide" are typically aluminium oxyhydroxide salts, which are usually at least partially crystalline. Aluminium oxyhydroxide, which can be represented by the formula AlO(OH), can be distinguished from other aluminium compounds, such as aluminium hydroxide Al(OH)$_3$, by infrared (IR) spectroscopy, in particular by the presence of an adsorption band at 1070 cm$^{-1}$ and a strong shoulder at 3090-3100 cm$^{-1}$ [chapter 9 of *Vaccine Design* . . . (1995) eds. Powell & Newman. ISBN: 030644867X. Plenum.] The degree of crystallinity of an aluminum hydroxide adjuvant is reflected by the width of the diffraction band at half height (WHH), with poorly-crystalline particles showing greater line broadening due to smaller crystallite sizes. The surface area increases as WHH increases, and adjuvants with higher WHH values have been seen to have greater capacity for antigen adsorption. A fibrous morphology (e.g. as seen in transmission electron micrographs) is typical for aluminum hydroxide adjuvants. The pI of aluminium hydroxide adjuvants is typically about 11 i.e. the adjuvant itself has a positive surface charge at physiological pH. Adsorptive capacities of between 1.8-2.6 mg protein per mg Al$^{+++}$ at pH 7.4 have been reported for aluminium hydroxide adjuvants.

The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt. Hydroxyphosphates generally have a PO$_4$/Al molar ratio between 0.3 and 1.2. Hydroxyphosphates can be distinguished from strict AlPO$_4$ by the presence of hydroxyl groups. For example, an IR spectrum band at 3164 cm$^{-1}$ (e.g. when heated to 200° C.) indicates the presence of structural hydroxyls [ch. 9 of Vaccine Design . . . (1995) eds. Powell & Newman. ISBN: 030644867X. Plenum.].

The PO$_4$/Al$^{3+}$ molar ratio of an aluminium phosphate adjuvant will generally be between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with PO$_4$/Al molar ratio between 0.84 and 0.92, included at 0.6 mg Al$^{3+}$/ml. The aluminium phosphate will generally be particulate (e.g. plate-like morphology as seen in transmission electron micrographs). Typical diameters of the particles are in the range 0.5-20 μm (e.g. about 5-10 μm) after any antigen adsorption. Adsorptive capacities of between 0.7-1.5 mg protein per mg Al$^{+++}$ at pH 7.4 have been reported for aluminium phosphate adjuvants.

The point of zero charge (PZC) of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

Suspensions of aluminium salts used to prepare compositions of the invention may contain a buffer (e.g. a phosphate or a histidine or a Tris buffer), but this is not always necessary. The suspensions are preferably sterile and pyrogen-free. A suspension may include free aqueous phosphate ions e.g. present at a concentration between 1.0 and 20 mM, preferably between 5 and 15 mM, and more preferably about 10 mM. The suspensions may also comprise sodium chloride.

In one embodiment, an adjuvant component includes a mixture of both an aluminium hydroxide and an aluminium phosphate. In this case there may be more aluminium phosphate than hydroxide e.g. a weight ratio of at least 2:1 e.g. ≥5:1, ≥6:1, ≥7:1, ≥8:1, ≥9:1, etc.

The concentration of Al$^{+++}$ in a composition for administration to a patient is preferably less than 10 mg/ml e.g. ≤5 mg/ml, ≤4 mg/ml, ≤3 mg/ml, ≤2 mg/ml, ≤1 mg/ml, etc. A preferred range is between 0.3 and 1 mg/ml. A maximum of <0.85 mg/dose is preferred.

Oil Emulsions

Oil emulsion compositions suitable for use as adjuvants in the invention include squalene-water emulsions, such as MF59™ [Chapter 10 of *Vaccine Design* . . . (1995) eds. Powell & Newman. ISBN: 030644867X. Plenum.] (5% Squalene, 0.5% TWEEN™ 80, and 0.5% SPAN™ 85, formulated into submicron particles using a microfluidizer). Complete Freund's adjuvant (CFA) and incomplete Freund's adjuvant (IFA) may also be used.

Various suitable oil-in-water emulsions are known, and they typically include at least one oil and at least one surfactant, with the oil(s) and surfactant(s) being biodegradable (metabolisable) and biocompatible. The oil droplets in the emulsion are generally less than 5 μm in diameter, and advantageously the emulsion comprises oil droplets with a sub-micron diameter, with these small sizes being achieved with a microfluidiser to provide stable emulsions. Droplets with a size less than 220 nm are preferred as they can be subjected to filter sterilization.

The invention can be used with oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoid known as squalene, 2,6,10,15,19,23-hexamethyl-2,6,10,14,18,22-tetracosahexaene. Other preferred oils are the tocopherols (see below). Oil in water emulsions comprising sqlauene are particularly preferred. Mixtures of oils can be used.

Surfactants can be classified by 'HLB' (hydrophile/lipophile balance). Preferred surfactants of the invention have a HLB of at least 10, preferably at least 15, and more preferably at least 16. The invention can be used with surfactants including, but not limited to: the polyoxyetlylene sorbitan esters surfactants (commonly referred to as the TWEEN™), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (TRITON™ X-100, or t-octylphenoxypolyethoxyethanol) being of particular interest; (octylphenoxy)polyethoxyethanol (IGEPAL CA-630/NP-40); phospholipids such as phosphatidylcholine (lecithin); polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPAN™), such as sorbitan trioleate (SPAN™ 85) and sorbitan monolaurate. Preferred surfactants for including in the emulsion are TWEEN™ 80 (polyoxyethylene sorbitan monooleate), SPAN™ 85 (sorbitan trioleate), lecithin and TRITON™ X-100. As mentioned above, detergents such as TWEEN™ 80 may contribute to the thermal stability seen in the examples below.

Mixtures of surfactants can be used e.g. TWEEN™ 80/SPAN™ 85 mixtures. A combination of a polyoxyethylene sorbitan ester such as polyoxyethylene sorbitan monooleate (TWEEN™ 80) and an octoxynol such as t-octylphehoxypolyethoxyethanol (TRITON™ X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as TWEEN™ 80) 0.01 to 1%; in particular about 0.1%; octyl- or nonylphenoxy polyoxyethanols (such as TRITON™ X-100, or other detergents in the TRITON™ series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Specific oil-in-water emulsion adjuvants useful with the invention include, but are not limited to:

A submicron emulsion of squalene, TWEEN™ 80, and SPAN™ 85. The composition of the emulsion by volume can be about 5% squalene, about 0.5% polysorbate 80 and about 0.5% SPAN™ 85. In weight terms, these ratios become 4.3% squalene, 0.5% polysorbate 80 and 0.48% SPAN™ 85. This adjuvant is known as 'MF59™'. The MF59™ emulsion advantageously includes citrate ions e.g. 10 mM sodium citrate buffer.

An emulsion comprising squalene, an α-tocopherol, and polysorbate 80. These emulsions may have from 2 to 10% squalene, from 2 to 10% tocopherol and from 0.3 to 3% TWEEN™ 80, and the weight ratio of squalene tocopherol is preferably ≤1 (e.g. 0.90) as this provides a more stable emulsion, Squalene and TWEEN™ 80 may be present volume ratio of about 5:2, or at a weight ratio of about 11:5. One such emulsion can be made by dissolving TWEEN™ 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm.

An emulsion of squalene, a tocopherol, and a TRITON™ detergent (e.g. TRITON™ X-100). The emulsion may also include a 3d-MPL™(see below). The emulsion may contain a phosphate buffer.

An emulsion comprising a polysorbate (e.g. polysorbate 80), a TRITON™ detergent (e.g. TRITON™ X-100) and a tocopherol (e.g. an α-tocopherol succinate). The emulsion may include these three components at a mass ratio of about 75:11:10 (e.g. 750 µg/ml polysorbate 80, 110 µg/ml TRITON™ X-100 and 100 µg/ml α-tocopherol succinate), and these concentrations should include any contribution of these components from antigens. The emulsion may also include squalene. The emulsion may also include a 3d-MPL™ (see below). The aqueous phase may contain a phosphate buffer.

An emulsion of squalane, polysorbate 80 and poloxamer 401 ("PLURONIC™ L121"). The emulsion can be formulated in phosphate buffered saline, pH 7.4. This emulsion is a useful delivery vehicle for muramyl dipeptides, and has been used with threonyl-MDP in the "SAF-1" adjuvant (0.05-1% Thr-MDP, 5% squalane, 2.5% Pluronic L121 and 0.2% polysorbate 80). It can also be used without the Thr-MDP, as in the "AF" adjuvant (5% squalane, 1.25% Pluronic L121 and 0.2% polysorbate 80). Microfluidisation is preferred.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'SPAN™ 80'). The emulsion is preferably thermoreversible and/or has at least 90% of the oil droplets (by volume) with a size less than 200 nm. The emulsion may also include one or more of: alditol; a cryoprotective agent (e.g. a sugar, such as dodecylmaltoside and/or sucrose); and/or an alkylpolyglycoside. Such emulsions may be lyophilized.

An emulsion having from 0.5-50% of an oil, 0.1-10% of a phospholipid, and 0.05-5% of a non-ionic surfactant. Preferred phosoholipid components are phosphatidylcholine, phosphatidyletethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, TWEEN™ 80 or SPAN™ 80). Additives may be included, such as QuilA saponin, cholesterol, a saponin-lipophile conjugate (such as GPI-0100, produced by addition of aliphatic amine to desacylsaponin via the carboxyl group of glucuronic acid), dimethyldioctadecyalammonium bromide and/or N,N-dioctadecyl-N,N-bis(2-hydroxyethyl)propanediamine.

An emulsion comprising a mineral oil, a non ionic lipophilic ethoxylated fatty alcohol, and a non-ionic hydrophilic surfactant (e.g. an ethoxylated fatty alcohol and/or polyoxyethylene-polyoxypropylene block copolymer) (see WO2006/113373).

An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer) (see WO2006/113373).

An emulsion in which a saponin (e.g. QuilA or QS21) and a sterol (e.g. a cholesterol) are associated as helical micelles.

Antigens (VLPs) and adjuvants in a composition will typically be in admixture at the time of delivery to a patient. The emulsions may be mixed with antigen (VLP) during manufacture, or extemporaneously, at the time of delivery. Thus the adjuvant and antigen (VLP) may be kept separately in a packaged or distributed vaccine, ready for final formulation at the time of use. The antigen (VLP) will generally be in an aqueous form, such that the vaccine is finally prepared by mixing two liquids. The volume ratio of the two liquids for mixing can vary (e.g. between 5:1 and 1:5) but is generally about 1:1.

Saponin formulations (see chapter 22 of *Vaccine Design* . . . (1995) eds. Powell & Newman. ISBN: 030644867X. Plenum.)

Saponin formulations may also be used as adjuvants in the invention. Saponins are a heterogeneous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornate* (sarsaparilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as STIMULON™.

Saponin compositions have been purified using HPLC and RP-HPLC. Specific purified fractions using these techniques have been identified, including QS7, QS 17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol.

Combinations of saponins and cholesterols can be used to form unique particles called immunostimulating complexes (ISCOMs) (chapter 23 of *Vaccine Design* . . . (1995) eds. Powell & Newman. ISBN: 030644867X. Plenum.). ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in WO96/33739. Optionally, the ISCOMS may be devoid of additional detergent.

Virosomes and Virus-like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1).

Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL™) and 3-O-deacylated MPL™ (3dMPL™). 3dMPL™ is a mixture of 3 de-O-acylated monophosphoryl lipid A with 4, 5 or 6 acylated chains. A preferred "small particle" form of 3 De-O-acylated monophosphoryl lipid A is disclosed in EP-A-0689454. Such "small particles" of 3dMPL™ are small enough to be sterile filtered through a 0.22 µm membrane (EP-A-0689454). Other non-toxic LPS derivatives include monophosphoryl lipid A mimics, such as aminoalkyl glucosaminide phosphate derivatives e.g. RC-529.

Lipid A derivatives include derivatives of lipid A from *Escherichia coli* such as OM-174. OM-174 is described for example in Meraldi et al. (2003) *Vaccine* 21:2485-2491 and Pajak et al. (2003) *Vaccine* 21:836-842.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References Kandimalla et al. (2003) *Nucleic Acids Research* 31:2393-2400; WO02/26757, and WO99/62923 disclose possible analog substitutions e.g. replacement of guanosine with 2'-deoxy-7-deaza-guanosine. The adjuvant effect of CpG oligonucleotides is further discussed in Krieg (2003) Nature Medicine 9:831-835; McCluskie et al. (2002) FEMS Immunology and Medical Microbiology 32:179-185; WO98/40100; U.S. Pat. Nos. 6,207,646; 6,239,116; and 6,429,199.

The CpG sequence may be directed to TLR9, such as the motif GTCGTT or TTCGTT (Kandimalla et al. (2003) *Biochemical Society Transactions* 31 (part 3):654-658). The CpG sequence may be specific for inducing a Th1 immune response, such as a CpG-A ODN, or it may be more specific for inducing a B cell response, such a CpG-B ODN. CpG-A and CpG-B ODNs are discussed in Blackwell et al. (2003) J Immunol 170:4061-4068; Krieg (2002) Trends Immunol 23:64-65 and WO01/95935. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, Kandimalla et al. (2003) *Biochemical Society Transactions* 31 (part 3):654-658 & Kandimalla et al. (2003) BBRC 306: 948-953; Bhagat et al. (2003) BBRC 300:853-861 and WO03/035836

A particularly useful adjuvant based around immunostimulatory oligonucleotides is known as IC-31™ (Schellack et al. (2006) *Vaccine* 24:5461-72). Thus an adjuvant used with the invention may comprise a mixture of (i) an oligonucleotide (e.g. between 15-40 nucleotides) including at least one (and preferably multiple) CpI motifs (i.e. a cytosine linked to an inosine to form a dinucleotide), and (ii) a polycationic polymer, such as an oligopeptide (e.g. between 5-20 amino acids) including at least one (and preferably multiple) Lys-Arg-Lys tripeptide sequence(s). The oligonucleotide may be a deoxynucleotide comprising 26-mer sequence 5'-(IC)$_{13}$-3' (SEQ ID NO: 1). The polycationic polymer may be a peptide comprising 11-mer amino acid sequence KLKLLLLLKLK (SEQ ID NO: 2).

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or *pertussis* ("PT"). The use of detoxified ADP-ribosylating toxins as mucosal adjuvants is described in WO95/17211 and as parenteral adjuvants in WO98/42375. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in Beignon et al. (2002) Infect Immun 70:3012-3019; Pizza et al. (2001) Vaccine 19:2534-2541; Pizza et al. (2000) Int J Med Microbiol 290:455-461; Scharton-Kersten et al. (2000) Infect Immun 68:5306-5313; Ryan et al. (1999) Infect Immun 67:6270-6280; Partidos et al. (1999) Immunol Lett 67:209-216; Peppoloni et al. (2003) Expert Rev Vaccines 2:285-293; Pine et al. (2002) J Control Release 85:263-270 and Tebbey et al. (2000) Vaccine 18:2723-34. A useful CT mutant is or CT-E29H. Numerical reference for amino acid substitutions is preferably based on the alignments of the A and B subunits of ADP-ribosylating toxins set forth in Domenighini et al. (1995) *Mol Microbiol* 15:1165-1167, specifically incorporated herein by reference in its entirety.

Human Immunomodulators

Human immunomodulators suitable for use as adjuvants in the invention include cytokines, such as interleukins (e.g. IL-1, IL-2, IL-4, IL-5, IL-6, IL-7, IL-12, etc.) (WO99/40936 and WO99/44636), interferons (e.g. interferon-γ), macrophage colony stimulating factor, and tumor necrosis factor. A preferred immunomodulator is IL-12.

Bioadhesives and Mucoadhesives

Bioadhesives and mucoadhesives may also be used as adjuvants in the invention. Suitable bioadhesives include esterified hyaluronic acid microspheres (Singh et al] (2001) *J Cont Release* 70:267-276) or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention (WO99/27960).

Microparticles

Microparticles may also be used as adjuvants in the invention. Microparticles (i.e. a particle of ~100 nm to ~150 μm in diameter, more preferably ~200 nm to 30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

Liposomes (Chapters 13 & 14 of *Vaccine Design* . . . (1995) eds. Powell & Newman. ISBN: 030644867X. Plenum.)

Examples of liposome formulations suitable for use as adjuvants are described in U.S. Pat. Nos. 6,090,406, 5,916, 588 and EP A 0626169.

Polyoxyethylene Ether and Polyoxyethylene Ester Formulations

Adjuvants suitable for use in the invention include polyoxyethylene ethers and polyoxyethylene esters (WO99/52549). Such formulations further include polyoxyethylene sorbitan ester surfactants in combination with an octoxynol (WO01/21207) as well as polyoxyethylene alkyl ethers or ester surfactants in combination with at least one additional non-ionic surfactant such as an octoxynol (WO01/21152). Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

Polyphosphazene (PCPP)

PCPP formulations are described, for example, in Andrianov et al. (1998) *Biomaterials* 19:109-115 and Payne et al. (1998) *Adv Drug Delivery Review* 31:185-196.

Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

Imidazoquinolone Compounds

Examples of imidazoquinolone compounds suitable for use adjuvants in the invention include Imiquamod and its homologues (e.g. "Resiquimod 3M"), described further in Stanley (2002) *Clin Exp Dermatol* 27:571-577 and Jones (2003) *Curr Opin Investig Drugs* 4:214-218.

The invention may also comprise combinations of aspects of one or more of the adjuvants identified above. For example, the following adjuvant compositions may be used in the invention: (1) a saponin and an oil-in-water emulsion (WO99/11241); (2) a saponin (e.g. QS21)+a non-toxic LPS derivative (e.g. 3dMPL™) (WO94/00153); (3) a saponin (e.g. QS21)+a non-toxic LPS derivative (e.g. 3dMPL™)+a cholesterol; (4) a saponin (e.g. QS21)+3dMPL™+IL-12 (optionally+a sterol) (WO98/57659); (5) combinations of 3dMPL™ with, for example, QS21 and/or oil-in-water emulsions (European patent applications 0835318, 0735898 and 0761231 ); (6) SAF, containing 10% squalane, 0.4% TWEEN™ 80™, 5% pluronic-block polymer L121, and thr-MDP™, either microfluidized into a submicron emulsion or vortexed to generate a larger particle size emulsion; (7) RIBI™ adjuvant system (RAS), (Ribi Immunochem) containing 2% squalene, 0.2% TWEEN™ 80, and one or more bacterial cell wall components from the group consisting of monophosphorylipid A (MPL), trehalose dimycolate (TDM), and cell wall skeleton (CWS), preferably MPL™+CWS (Detox™); and (8) one or more mineral salts (such as aluminum salt)+a non-toxic derivative of LPS (such as 3dMPL™).

Other substances that act as immunostimulating agents are disclosed in chapter 7 of *Vaccine Design* . . . (1995) eds. Powell & Newman. ISBN: 030644867X. Plenum. The use of an aluminium hydroxide and/or aluminium phosphate adjuvant is useful, particularly in children, and antigens are generally adsorbed to these salts. Squalene-in-water emulsions are also preferred, particularly in the elderly. Useful adjuvant combinations include combinations of Th1 and Th2 adjuvants such as CpG and alum or resiquimod and alum. A combination of aluminium phosphate and 3dMPL may be used.

In some embodiments, the invention is an immunogenic composition that contains a parvovirus VLP that contains VP1 and VP2, as described herein, and an adjuvant, such as MF59™. The VLP and the adjuvant (e.g. MF59™) can be premixed and provided as a single composition, or can be provided as a separate components that are to be mixed prior to administration.

E. Administration

Compositions of the invention will generally be administered directly to a patient. Direct delivery may be accomplished by parenteral injection (e.g. subcutaneously, intraperitoneally, intravenously, intramuscularly, or to the interstitial space of a tissue) for example using a syringe and hypodermic needle, or mucosally, such as by rectal, oral (e.g. tablet, spray), vaginal, topical, transdermal (See e.g. WO99/27961) or transcutaneous (See e.g. WO02/074244 and WO02/064162), intranasal (See e.g. WO03/028760), ocular, aural, pulmonary or other mucosal administration. Immunogenic compositions can also be administered topically by direct transfer to the surface of the skin. Topical administration can be accomplished without utilizing any devices, or by contacting naked skin with the immunogenic composition utilizing a bandage or a bandage-like device (see, e.g., U.S. Pat. No. 6,348,450).

Preferably the mode of administration is parenteral, mucosal or a combination of mucosal and parenteral immunizations. Even more preferably, the mode of administration is parenteral, mucosal or a combination of mucosal and parenteral immunizations in a total of 1-2 vaccinations 1-3 weeks apart. Preferably the route of administration includes but is not limited to oral delivery, intra-muscular delivery and a combination of oral and intramuscular delivery. A particularly preferred mode of administration is by intramuscular injection, for example using a syringe and hypodermic needle. Preferably the immunogenic composition is administered in two doses intramuscularly.

Compositions of the invention may be administered concomitantly with routine childhood immunizations or with human papillomavirus and/or group B strep vaccinations delivered to adolescent females.

It has already been demonstrated that mucosal and systemic immune responses to antigens from mucosal pathogens, such as *Helicobacter pylori* antigens can be enhanced through mucosal priming followed by systemic boosting immunizations (see Vajdy et al. (2003) Immunology 110: 86-94). In some embodiments, the method for treating or preventing an infection by a parvovirus, comprises mucosally administering to a subject in need thereof a first immunogenic composition comprising one or more parvovirus antigens followed by parenterally administering a therapeutically effective amount of a second immunogenic composition comprising one or more parvovirus antigens.

The immunogenic composition may be used to elicit systemic and/or mucosal immunity, preferably to elicit an enhanced systemic and/or mucosal immunity.

Preferably the immune response is characterized by the induction of a serum IgG and/or intestinal IgA immune response.

As noted above, prime-boost methods are preferably employed where one or more gene delivery vectors and/or polypeptide antigens are delivered in a "priming" step and, subsequently, one or more second gene delivery vectors and/or polypeptide antigens are delivered in a "boosting" step. In certain embodiments, priming and boosting with one or more gene delivery vectors or polypeptide antigens described herein is followed by additional boosting with one or more polypeptide-containing compositions (e.g., polypeptides comprising parvovirus antigens). A VLP is a polypeptide-containing composition. VLPs may be formed in a host immunized with a suitable gene delivery vector.

In any method involving co-administration, the various compositions can be delivered in any order. Thus, in embodiments including delivery of multiple different compositions or molecules, the nucleic acids need not be all delivered before the polypeptides. For example, the priming step may include delivery of one or more polypeptides and the boosting comprises delivery of one or more nucleic acids and/or one or more polypeptides. Multiple polypeptide administrations can be followed by multiple nucleic acid administrations or polypeptide and nucleic acid administrations can be performed in any order. Thus, one or more of the gene delivery vectors described herein and one or more of the polypeptides described herein can be co-administered in any order and via any administration route. Therefore, any combination of polynucleotides and polypeptides described herein can be used to elicit an immune reaction.

(i). Dosage Regime

Dosage treatment can be according to a single dose schedule or a multiple dose schedule. Multiple doses may be used in a primary immunization schedule and/or in a booster immunization schedule. In a multiple dose schedule, the various doses may be given by the same or different routes, e.g. a parenteral prime and mucosal boost, a mucosal prime and parenteral boost, etc. For example, a multiple dose schedule may comprise a prime, followed by two boosts. The prime and/or boost dose will preferably be co-administered with an adjuvant.

Preferably the dosage regime enhances the avidity of the antibody response leading to antibodies with a neutralizing characteristic. An in-vitro neutralization assay may be used to test for neutralizing antibodies (see for example Asanaka et al. (2005) *J of Virology* 102: 10327; Wobus et al. (2004) *PLOS Biology* 2(12); e432; and Dubekti et al. (2002) *J Medical Virology* 66: 400).

There is a strong case for a correlation between serum antibody levels and protection from disease caused by parvovirus.

Parvovirus VLPs as described above can be administered to a mammal, such as a mouse, baboon, chimpanzee, or human, to activate parvovirus-specific T cells in vivo. Administration can be by any means known in the art, including parenteral, intranasal, intramuscular or subcutaneous injection, including injection using a needle or syringe.

A composition of the invention comprising a parvovirus VLP is administered in a manner compatible with the particular composition used and in an amount which is effective to induce an immune response (e.g., a T cell response and/or a humoral response), preferably a protective immune response.

Parvovirus-specific T cell responses can be measured by, inter alia, a 51Cr release assay, a lymphoproliferation assay, or by intracellular staining for IFN-γ. The proteins can be administered either to a mammal which is not infected with a parvovirus or can be administered to a parvovirus-infected mammal. The particular dosages of the protein in a composition will depend on many factors including, but not limited to the species, age, and general condition of the mammal to which the composition is administered, and the mode of administration of the composition. An effective amount of the composition of the invention can be readily determined using only routine experimentation. In vitro and in vivo models can be employed to identify appropriate doses. Generally, 0.5, 0.75, 1.0, 1.5, 2.0, 2.5, 5, 10, 20 or 50 mg of a parvovirus polypeptide or VLP will be administered to a large mammal, such as a baboon, chimpanzee, or human. If desired, co-stimulatory molecules or adjuvants can also be provided before, after, or together with the compositions.

Immune responses of the mammal generated by the delivery of a composition of the invention, including activation of parvovirus-specific T cells, can be enhanced by varying the dosage, route of administration, or boosting regimens. Compositions of the invention may be given in a single dose schedule, or preferably in a multiple dose schedule in which a primary course of vaccination includes 1-10 separate doses, followed by other doses given at subsequent time intervals required to maintain and/or reinforce an immune response, for example, at 1-4 months for a second dose, and if needed, a subsequent dose or doses after several months.

F. Tests to Determine the Efficacy of an Immune Response

One way of assessing efficacy of therapeutic treatment involves monitoring infection after administration of a composition of the invention. One way of assessing efficacy of prophylactic treatment involves monitoring immune responses against the antigens in the compositions of the invention after administration of the composition.

Another way of assessing the immunogenicity of the component proteins of the immunogenic compositions of the present invention is to express the proteins recombinantly and to screen patient sera or mucosal secretions by immunoblot. A positive reaction between the protein and the patient serum indicates that the patient has previously mounted an immune response to the protein in question—that is, the protein is an immunogen. This method may also be used to identify immunodominant proteins and/or epitopes.

Another way of checking efficacy of therapeutic treatment involves monitoring infection after administration of the compositions of the invention. One way of checking efficacy of prophylactic treatment involves monitoring immune responses systemically (such as monitoring the level of IgG1 and IgG2a production) and/or mucosally (such as monitoring the level of IgA production) against the antigens in the compositions of the invention after administration of the composition. Typically, serum specific antibody responses are determined post-immunization but pre-challenge whereas mucosal specific antibody body responses are determined post-immunization and post-challenge.

There is currently no accepted animal model for evaluating protective immunity induced by the human parvovirus (e.g., parvovirus B19) immunogenic compositions of the present invention. However, the capacity of such compositions to induce an immune response can be assessed in suitable animals, as described herein. Other, non-human parvovirus, immunogenic compositions of the present invention can be evaluated in in vitro and in vivo animal models prior to host, e.g., human, administration. Particularly useful mouse models include those in which intraperitoneal immunization is followed by either intraperitoneal challenge or intranasal challenge.

The efficacy of immunogenic compositions of the invention can also be determined in vivo by challenging animal models of infection, e.g., guinea pigs or mice or rhesus macaques, with the immunogenic compositions. The immunogenic compositions may or may not be derived from the same strains as the challenge strains. Preferably the immunogenic compositions are derivable from the same strains as the challenge strains.

The immune response may be one or both of a TH1 immune response and a TH2 response. The immune response may be an improved or an enhanced or an altered immune response. The immune response may be one or both of a systemic and a mucosal immune response. Preferably the immune response is an enhanced systemic and/or mucosal response.

An enhanced systemic and/or mucosal immunity is reflected in an enhanced TH1 and/or TH2 immune response. Preferably, the enhanced immune response includes an increase in the production of IgG1 and/or IgG2a and/or IgA. Preferably the mucosal immune response is a TH2 immune response. Preferably, the mucosal immune response includes an increase in the production of IgA.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 production.

A TH1 immune response may include one or more of an increase in CTLs, an increase in one or more of the cytokines associated with a TH1 immune response (such as IL-2, IFNγ, and TNFβ), an increase in activated macrophages, an increase in NK activity, or an increase in the production of IgG2a. Preferably, the enhanced TH1 immune response will include an increase in IgG2a production.

Immunogenic compositions of the invention, in particular, immunogenic composition comprising one or more antigens of the present invention may be used either alone or in combination with other antigens optionally with an immunoregulatory agent capable of eliciting a Th1 and/or Th2 response.

The immune response may be an antibody-mediated immune mechanism. Preferably, the antibody is a serum antibody, more preferably, a neutralizing serum antibody. The immunogenic compositions of the present invention may be tested primarily by assessing antibody titers (e.g., total antibody and/or neutralizing antibody), using any suitable method, such as western blots or ELISA for evaluation of immunoreactivity against parvovirus VP1 and/or VP2 (Wong et al., J. of Virology, 82(5):2470-2476 (2008); Bostic et al., J. Infectious Disease, 179:619-626 (1999)).

The immunogenic compositions of the invention will preferably elicit both a cell mediated immune response as well as a humoral immune response in order to effectively address an infection. This immune response will preferably induce long lasting (e.g., neutralizing) antibodies and a cell mediated immunity that can quickly respond upon exposure to one or more infectious antigens. By way of example, evidence of neutralizing antibodies in patients blood samples is considered as a surrogate parameter for protection since their formation is of decisive importance for virus elimination in parvovirus infections (see Young and Brown, NEJM 350:586-97, 2004).

The invention also comprises an immunogenic composition comprising one or more immunoregulatory agent, such as a mineral salt, such as an aluminium salt and an oligonucleotide containing a CpG motif. Most preferably, the immunogenic composition includes both an aluminium salt and an oligonucleotide containing a CpG motif. Alternatively, the immunogenic composition includes an ADP ribosylating toxin, such as a detoxified ADP ribosylating toxin and an oligonucleotide containing a CpG motif. Preferably, the one or more immunoregulatory agents include an adjuvant. The adjuvant may be selected from one or more of the group consisting of a TH1 adjuvant and TH2 adjuvant, further discussed above.

G. Use of the Immunogenic Compositions as Medicaments

The invention also provides a composition of the invention for use as a medicament. The medicament is preferably able to raise an immune response in a mammal (i.e. it is an immunogenic composition) and is more preferably a vaccine. The invention also provides the use of the compositions of the invention in the manufacture of a medicament for raising an immune response in a mammal. The medicament is preferably a vaccine. Preferably the vaccine is used to prevent and/or treat an erythema infectiosum in children, transient aplastic crisis in patients with red blood cell dyscrasias, usually sickle cell anemia, hemolytic anemia or hereditary spherocytosis, chronic red blood cell aplasia and anemia in immunodeficient patients, persistent infection in immunosuppressed individuals, persistent arthropathy in adults, persistent and sometimes lethal cytopenias in immunocomprised patients, exacerbation of anemia during co-infection with *Plasmodium*, exacerbated anemia in malaria and hydrops fetalis or spontaneous abortion in pregnant women.

The invention provides methods for inducing or increasing an immune response using the compositions described herein. The immune response is preferably protective and can include antibodies and/or cell-mediated immunity (including systemic and mucosal immunity). Immune responses include booster responses.

The invention also provides a method for raising an immune response in a mammal comprising the step of administering an effective amount of a composition of the invention. The immune response is preferably protective and preferably involves antibodies and/or cell-mediated immunity. Preferably, the immune response includes one or both of a TH1 immune response and a TH2 immune response. The method may raise a booster response.

The mammal is preferably a human. Where the immunogenic composition, preferably a vaccine is for prophylactic use, the human is preferably a child (e.g. a toddler or infant, preferably pre-school, preferably one year or less or from three years (preferably 1-4 years) onwards) or a teenager (an adolescent); where the vaccine is for therapeutic use, the human is preferably a teenager or an adult. A vaccine intended for children may also be administered to adults, e.g. to assess safety, dosage, immunogenicity, etc. Preferably, the human is a teenager (an adolescent). More preferably, the human is a pre-adolescent teenager. Even more preferably, the human is a pre-adolescent female or male. Preferably the pre-adolescent male or female is around 9-12 years of age. Preferably the adolescent male or female is around 15-19 years of age. Preferably the male or female is around 20-49 years of age. Preferably the male or female is over 49 years of age. Preferably the human is elderly, preferably around 60-80 years of age.

Other populations who can benefit from the immunogenic compositions (e.g., vaccines) of the present invention include: children aged six to ten years; day care children; school-aged children and pediatric and/or elderly populations as discussed above; chronic anemia patients; children with sickle cell anemia; children with hereditary spherocytosis; female children, adolescent or adult females of childbearing age, e.g., for prevention of congenital infection (fetal infection); children living in geographic areas at risk for malaria or hookworm (e.g. areas where malaria or hookworm are endemic); children or adults who will become immunosuppressed (e.g., cancer patients, patients awaiting transplantation); children or adults who are planning surgical procedures that are likely to involve blood loss and require transfusion; transplant recipients, and immunocompromised individuals.

H. Kits

The invention also provides kits comprising one or more containers of immunogenic compositions of the invention. Compositions can be in liquid form or can be lyophilized, as can individual antigens. Suitable containers for the compositions include, for example, bottles, vials, syringes, and test tubes. Containers can be formed from a variety of materials, including glass or plastic. A container may have a sterile access port (for example, the container may be an intravenous solution bag or a vial having a stopper pierceable by a hypodermic injection needle).

The kit can further comprise a second container comprising a pharmaceutically-acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery device. The kit may further include a third component comprising an adjuvant.

The kit can also comprise a package insert containing written instructions for methods of inducing immunity or for treating infections. The package insert can be an unapproved draft package insert or can be a package insert approved by the Food and Drug Administration (FDA) or other regulatory body.

The invention also provides a delivery device pre-filled with the immunogenic compositions of the invention, such as a syringe with or without a hypodermic needle.

The invention also provides diagnostic kits that use VLPs produced by the method described above as antigens to determine seropositivity for parvovirus. The diagnostic kit can contain a parvovirus VLP as described herein, and one or more ancillary reagents to determine whether an individual is seropositive for antibodies that bind parvovirus. Suitable ancillary reagents include, for example, buffers, secondary or detecting antibodies (e.g., a labeled anti-human Ig antibody, a labeled anti-dog Ig antibody), detection agents and the like. In one example, the kit contains a parvovirus VLP and ancillary reagents for performing an ELISA or other suitable immunoassay. The kit can further comprise instructions for performing the diagnostic assay.

III. Exemplification

Below are examples of specific embodiments for carrying out the present invention. The examples are offered for illustrative purposes only, and are not intended to limit the scope of the present invention in any way.

The initial plasmid containing VP1 and VP2 under the control of two equal strength promoters was generated using traditional molecular biological techniques. The promoter preceding VP1 was then modified as mentioned above (e.g. TATA deletions, various deletions of the A-rich upstream sequence, introduction of start/stop sites upstream of the VP1 start codon).

TABLE 1

List of oligonucleotides used in the different cloning steps:

| | |
|---|---|
| C489G_A490C | 5'-CTGCTGTTGATTCTGCTGCTAGAATTGCTGATTTCAGATACTCTCAATT-3' (SEQ ID NO: 3) |
| VP1-MS1: | 5'-AGATCTACGCGTACAAAACAAAATGTCTAAGAAATCTGGTAAATGG -3' (SEQ ID NO: 4) |
| VP1-MS2 | 5'-AGATCTGTCGACTCATTACAATGGATGAACTCTAGATTTAGCAGTCC-3' (SEQ ID NO: 5) |
| VP2-AN1: | 5'-AGATCTCCTAGGACAAAACAAAATGACATCTGTTAATTCTGCTGAAGC-3' (SEQ ID NO: 6) |
| VP2-AN2: | 5'-AGATCTGCGGCCGCTCATTACAATGGATGAACTCTAGATTTAGCAGTC-3' (SEQ ID NO: 7) |
| dTATA.1: | 5'-AGATCTGGATCCTTCAATATGCGCACATACGCTG-3' (SEQ ID NO: 8) |
| dTATA.2: | 5'-TCTAGACCTAGGGGAATAATTTCAGGGAACTGGTTTCAACC-3' (SEQ ID NO: 9) |
| am-1: | 5'-CTAGCATTGTAATTCTGTAAATCTATTTCTTAAACTTC-3' (SEQ ID NO: 10) |
| am-2: | 5'-TTAAATTCTACTTTTATAGTTAGTCTTTTTTTTAGTTTTAAAAC-3' (SEQ ID NO: 11) |
| am-3: | 5'-ACCAAGAACTTAGTTTCGAATAAACACACATAAACAAACA-3' (SEQ ID NO: 12) |
| am-4: | 5'-CGCGTGTTTGTTTATGTGTGTTTATTCGAAACTAAGTTCTTGGTGTTTT AAAACTAAAAAAAAGAC-3' (SEQ ID NO: 13) |
| am-5: | 5'-TAACTATAAAAGTAGAATTTAAGAAGTTTAAGAAATAGATTTACAGAATTA CAATG-3' (SEQ ID NO: 14) |

Figure 2:
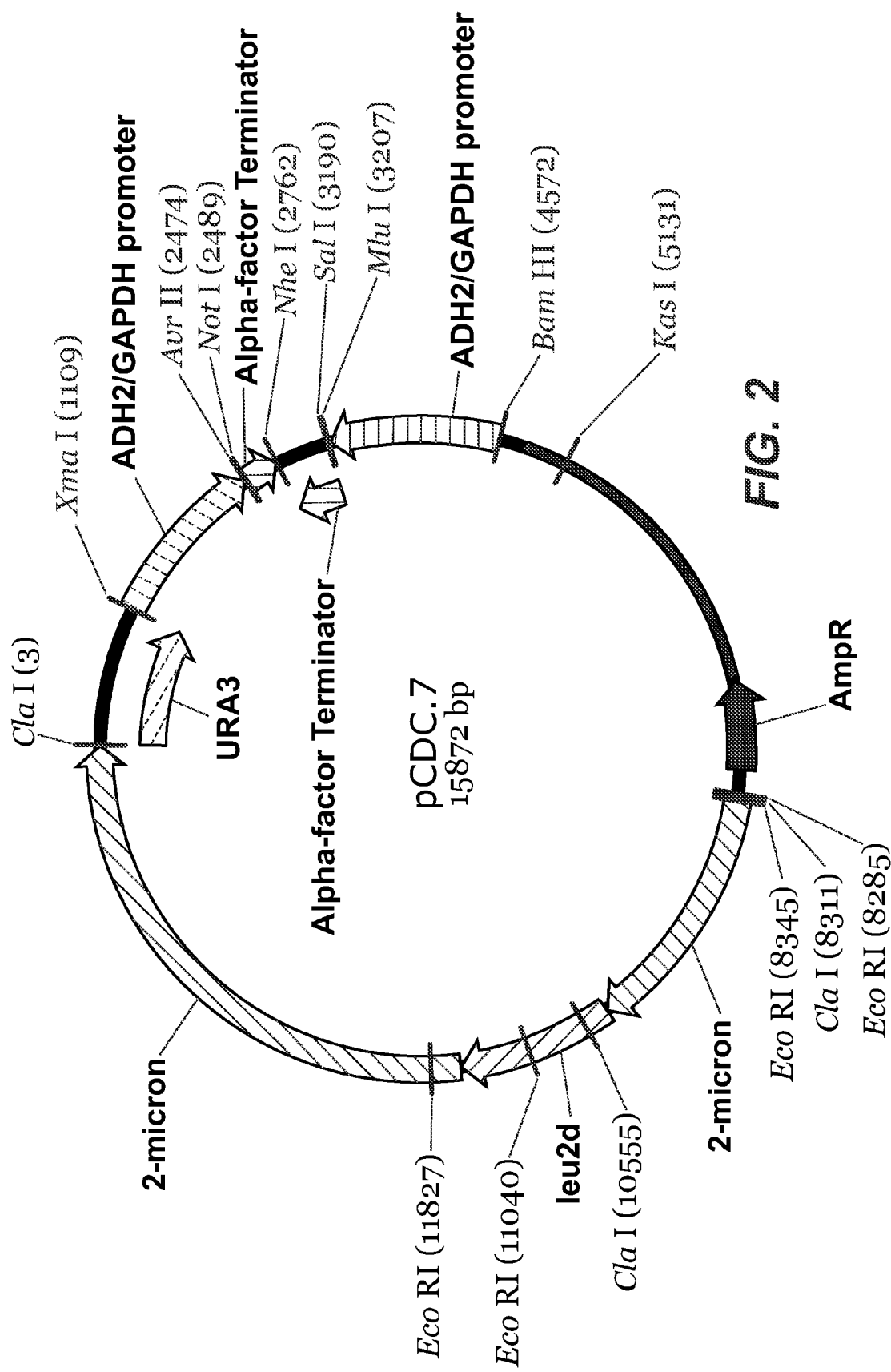
Figure 10:
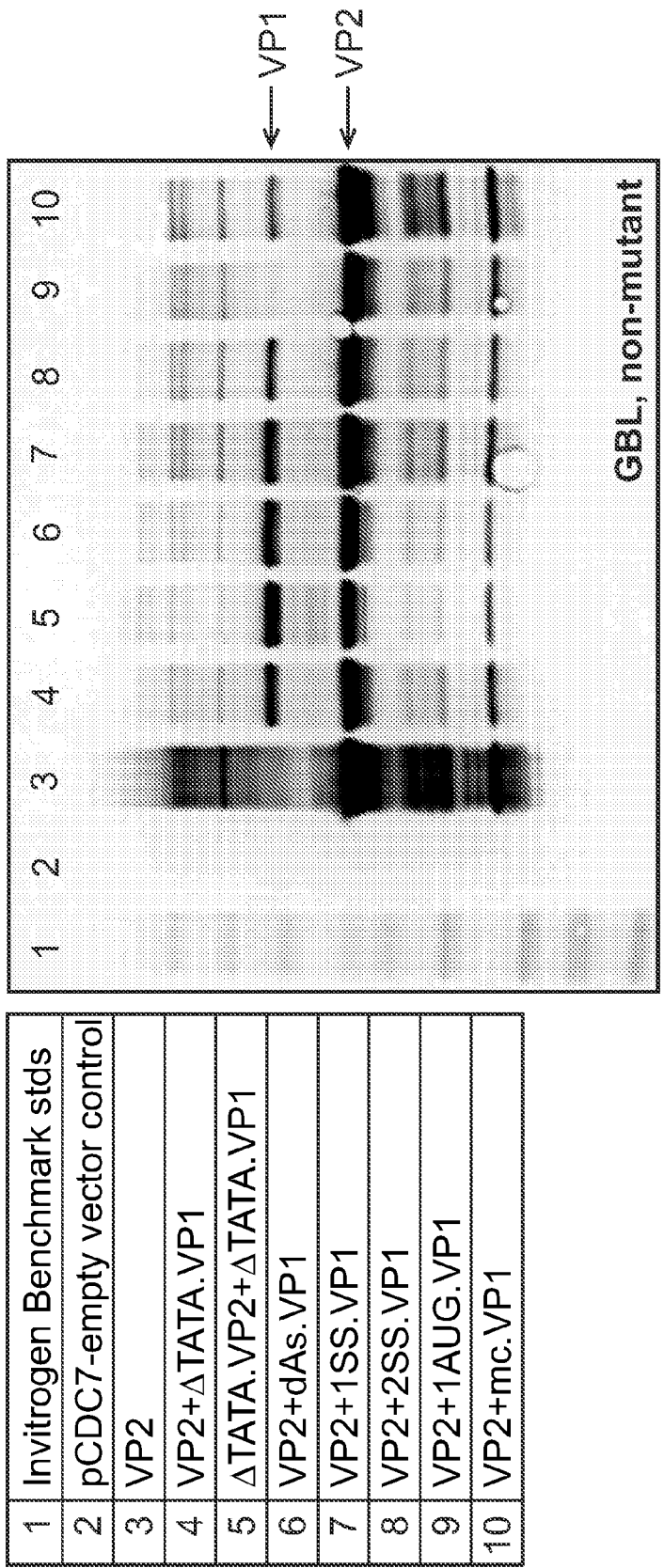

The first step was to generate PCR products for VP1 with MluI-SalI restriction ends appropriate for cloning in the pCDC7 yeast expression vector (FIG. 2) and for VP2 with AvrII-NotI restriction ends appropriate for cloning into the second expression cassette of pCDC7. In addition, an ACAAAACAAA (SEQ ID NO: 15) sequence was introduced between the 5' end restriction site and the initiating Met of the VP1 or VP2 sequence.

For VP2, the PCR amplification reaction contained 100 ng pMK-RG_parvo_shade_vp1, 50 pmoles each of primers VP2-AN1 and VP2-AN2, 10 ul of 10× Buffer with MgCl$_2$, 16 ul of dNTPs 1.25 mM each, H2O up to 100 ul and 0.75 ul DNA polymerase from Roche EXPAND HIGH FIDELITY™ PCR kit. Amplification conditions: 5' 95° C., 35 cycles: 30" 95° C., 1' 60° C., 2' 72° C., followed by a single 7' 72° C. extension cycle and a 4° C. hold.

The VP2 PCR reaction was purified using the Promega WIZARD™ PCR Preps DNA Purification System and digested with AvrII and NotI for 3 hours at 37° C., with 120 u of each enzyme in a 300 ul final volume. The 1685 bp AvrII-NotI fragment was then purified from 1% agarose GTG (genetic technology grade) using the Qiagen MINELUTE™ Gel Extraction Kit.

15 ng of the VP2 AvrII-NotI gel-purified PCR product was ligated to a dephosphorylated, gel-purified pT7Blue2 AvrII-NotI vector using the Roche Rapid DNA Ligation kit. After 20' at RT° the ligation reaction was used to transform competent HB101, then plated on LB agar plates containing 100 ug/ml ampicillin. Miniprep plasmid DNA was prepared from single ampicillin resistant colonies grown in Terrific Broth containing 100 ug/ml ampicillin; a portion of the DNA was digested with AvrII+NotI to confirm the presence of the VP2 insert. The plasmid from 3 positive clones was analyzed with sequencing.

For VP1, the PCR amplification reaction contained 100 ng pMK-RG_parvo_shade_vp1, 50 pmoles each of primers VP1-MS1 and VP1-MS2, 40 ul of 5' Hot Master Mix (2.5×) and H2O up to 100 ul. Amplification conditions: 5' 95° C., 35 cycles: 30" 95° C., 1' 60° C., 2' 72° C., followed by a single 7' 72° C. extension cycle and a 4° C. hold.

The VP1 PCR reactions were purified using the Promega WIZARD™ PCR Preps DNA Purification System and digested with MluI and SalI for 3 hours at 37° C., with 120u of each enzyme in a 300 ul final volume. The 2366 bp MluI-SalI fragments were then purified from 1% agarose GTG (genetic technology grade) using the Qiagen MinElute Gel Extraction kit.

An aliquot of VP1 MluI-SalI gel-purified PCR product was ligated to a dephosphorylated, gel-purified pGEM4Z MluI-SalI vector using the Roche Rapid DNA Ligation kit. After 20' at RT° the ligation reaction was used to transform competent HB101, then plated on LB agar plates containing 100 ug/ml ampicillin. Miniprep plasmid DNA was prepared from single ampicillin resistant colonies grown in Terrific Broth containing 100 ug/ml ampicillin; a portion of the DNA was digested with MluI+SalI to confirm the presence of the VP1 insert. The plasmid from 3 or 4 positive clones was analyzed with sequencing.

Next, the VP2 and the VP1 restriction fragments were prepared from sequence confirmed subclones. For VP2, 10 ug of pT7Blue2.AvrII.NotI.Parvo.VP2 #11 were digested for 2.5 hours at 37° C. with 80 units each of AvrII and NotI in a 200 ul final volume. For VP1, 12 ug of pGEM4Z.opti.Parvo.VP1 #3 was digested for 3 hours at 37° C. with 100 u each MluI and SalI in a 300 ul final volume. PvuI enzyme was included in the VP1 prep digest in order to prevent contamination of the VP1 fragment with vector. The VP2 and VP1 fragments were purified from 1% agarose GTG using the Qiagen MinElute Gel Extraction kit.

The bicistronic yeast expression vector pCDC7 was digested with AvrII+NotI, dephosphorylated with calf intestine alkaline phosphatase and then purified from 1% agarose GTG using the Qiagen MinElute Gel Extraction kit. Approximately 90 ng of the VP2 AvrII-NotI fragment was ligated to ~30 ng of the AvrII-NotI pCDC7 vector in a 20 ul reaction using the Roche Rapid DNA Ligation kit. After 20' at RT° the ligation reaction was used to transform competent HB101, then plated on LB agar plates containing 100 ug/ml ampicillin. Miniprep plasmid DNA was prepared from single ampicillin resistant colonies grown in Terrific Broth containing 100 ug/ml ampicillin; the plasmid DNA was digested with AvrII+NotI to confirm the presence of the VP2 insert.

To prepare a vector for the cloning of VP1 into the second expression cassette of pCDC7, approximately 10 ug of pCDC7.ParvoB19.VP2 #11 plasmid DNA from were digested for 3 hours at 37° C. with 100 u each of MluI and SalI in a 200 ul final volume. The digested plasmid was then dephosphorylated with 7 u calf intestine alkaline phosphatase for 1 hour at 37°. Next, the vector was purified from 1% agarose GTG using the Qiagen MinElute Gel Extraction kit.

Finally, ~100 ng of gel-purified VP1 MluI-SalI fragment was ligated to ~60 ng of the pCDC7.ParvoB19.VP2 #11 MluI-SalI vector in two separate 20 ul ligation reactions using the Roche Rapid Ligation kit. After 20' at RT° the ligation reaction was used to transform competent HB101, then plated on LB agar plates containing 100 ug/ml ampicillin. Miniprep plasmid DNA was prepared from single ampicillin resistant colonies grown in Terrific Broth containing 100 ug/ml ampicillin; the plasmid DNA was digested with MluI+SalI to confirm the presence of the VP1insert. pCDC7.ParvoB19.VP2.VP1 #2 was selected for amplification in 100 ml Terrific Broth containing 100 ug/ml ampicillin and subsequent plasmid DNA purification using a Qiagen MaxiPrep kit.

Next, the ΔTATA promoter restriction fragment was prepared from the sequence confirmed subclone. Approximately 8 ug of pT7Blue2.ΔTATA #9 was digested for 4 hours at 37° C., with 120 units each of BamHI and MluI in a 300 ul final volume. A BamHI-MluI yeast expression vector was prepared by digesting 5 ug pCDC7.ParvoB19.VP2.VP1 #2 with 80 units each of BamHI and MluI in a 200 ul reaction volume, followed by a 1 hour 37° C., dephosphorylation with 10 u calf intestine alkaline phosphatase. The promoter and the vector fragments were both purified from 1% agarose GTG using the Qiagen MinElute Gel Extraction kit.

Finally, ~20 ng of the 1333 bp BamHI-MluI ΔTATA promoter fragment was ligated to ~20 ng of BamHI-MluI pCDC7 vector (described in the previous paragraph) in a 20 ul reaction using the Roche Rapid DNA Ligation kit. After 20' at RT° the ligation reaction was used to transform competent HB101, then plated on LB agar plates containing 100 ug/ml ampicillin. Miniprep plasmid DNA was prepared from single ampicillin resistant colonies grown in Terrific Broth containing 100 ug/ml ampicillin; the DNA was digested with BamHI+MluI to confirm the presence of the 1333 bp ΔTATA promoter. pCDC7.ParvoB19.VP2+ΔTATA.VP1 #16 was selected for amplification in 100 ml Terrific Broth containing 100 ug/ml ampicillin and subsequent plasmid DNA purification using a Qiagen MaxiPrep kit.

EXAMPLE 1

Expression of Parvovirus B19 in Yeast

Parvovirus B19 VP2 and VP1 genes were co-expressed in *S. cerevisiae* AD3, characterized as follows: MATa, leu2, ura3-52, prb1-1122, pep4-3, prc1-407, gal2, [cir°]::pDM15 (pGAP/ADR1::G418R),::Yip5ΔleuAD.

The yeast are streaked on YEPD plates before selecting a single colony for preparation of competent cells for transformation. Yeast transformation was performed using the Invitrogen S.C. EASYCOMP™ Transformation kit. Transformants were obtained on ura-8% glucose selective plates. Several transformants were streaked for single colonies on ura-8% glucose selective plates. Single colonies were then patched on leu-8% glucose selective plates in order to increase plasmid copy number.

A small-scale expression check was done for several of the single colony patches. First, a 3 ml overnight culture in leu-7.1% glucose media was grown. Then, the leu-culture was diluted 1:20 into YEPD or Veggie YEPD. The culture was shaken at 30° C. or 25° C. for 48-72 hours. Induction occurred upon depletion of the glucose from the media.

The cell pellets were thawed, washed in water and pelleted in a graduated tube so that an estimate could be made for the packed cell volume. Each pellet was then resuspended in a volume of cold lysis buffer (10 mM NaPO4 pH7.5, 0.1% TRITON™ X-100, 0.5 M NaCl) equal to the packed cell volume, in order to normalize for differences in the density of different expression cultures. An aliquot of the cell/buffer suspension was lysed with washed glass beads (Sigma G8772) by vortexing at top speed for 1 hr. at 4°. The crude lysates were centrifuged at 13K for 30 min in a 4° C. microfuge to pellet the insoluble fraction. After the protein concentration of the supernatants was determined, 300 ug samples were prepared in 150 ul SDS sample buffer+50 mM DTT. Meanwhile, the insoluble pellet fraction (IP) was resuspended in 1 ml SDS sample buffer+50 mM DTT. The samples for soluble and insoluble fractions were boiled before loading onto 4-20% Tris-Glycine gels. For the soluble fraction, 10 µl (20 ug total protein) were loaded; for the insoluble pellet, 5 ul were loaded.

Gels were run in duplicate—one for Coomassie staining (Invitrogen SIMPLYBLUE™ safe stain) and one for western blot which was probed with a mouse monoclonal antibody to parvovirus B19 (Santa Cruz sc-58178).

Using the same protocol, four different colonies were analyzed to get a sense of the variability from colony to colony. Four 72 hour shake-flask expression cultures were inoculated with cells from four single-colony Leu-patches. The western blot in FIG. 9*b*. shows the range of variability for soluble VP2 and VP1 from four colonies of each construct.

EXAMPLE 2

Parvovirus B19 Purification Protocol

BCA Protein Assay (Pierce) using bovine serum alumin (BSA) was used as a standard reference for protein concentration determination. In some cases UV absorbance at 280 nm was used, assuming 1 absorbance unit=1 mg/ml as indicated by calibrated with BCA results.

SDS-PAGE was performed with gels from Invitrogen (NUPAGE™ 4-12% Bis-Tris cat#NP0322BOX) and NUPAGE™ MES SDS Running Buffer (cat#NP0002-02). Markers used for SDS-PAGE were the Full range RAIN- BOW™ molecular weight marker (GE Healthcare, cat# RPN800E). NATIVEPAGE™ 3-12% Bis-Tris Gels were used (Invitrogen cat# BN1003BOX) with the NATIVEPAGE™ Running buffer kit (Invitrogen cat# BN2007 and NATIVEPAGE™ Markers (Invitrogen cat#151-1901). SDS PAGE gels were stained using Coomassie Blue R-250 Stain Solution from Teknova (cat# C1050).

The SDS-PAGE gel was blotted on a nitro-cellulose membrane 1-BLOT™ System (Invitrogen) for purity and identity by western blot analysis. For yeast contaminant determinations a Yeast Whole Cell ELISA kit was used (*S. cerevisiae* HCP ELISA kit-CYGNUS Technologies, #F135).

Parvovirus B19 virus-like particles (VLPs) were purified from yeast cells expressing both VP1 and VP2. Yeast cells were resuspended in lysis buffer and the cells were broken open with multiple high pressure (25,000 psi) passes in a MICROFLUIDIZER™. Following a low speed spin (15,000×g) to separate cellular debris, the supernatant was subjected to a four hour high speed spin (100,000×g) into a 20%/70% sucrose step cushion. The cushion was fractionated and the fractions containing VLPs were diluted with a buffer (20 mM Tris pH 7.5, 100 mM NaCl). The VLPs were loaded onto a CAPTO™ Q column and eluted with high salt. The eluted fractions containing the VLPs were concentrated and buffer exchanged into a lower salt buffer (20 mM Tris pH 7.5, 100 mM NaCl) and stored at 4° C.

Parvovirus B19 VP1/VP2 VLPs were purified to greater than 90% purity and appeared to be identically sized (~26 nm) (FIG. 11A, 11B). The gels are based on the VP2/VP1 (delta TATA) VLPs. Additional VLPs were constructed that contained a site specific mutant.

Sucrose Shelf Cushion and Fractionation

A sucrose shelf was prepared in a 38 mL Polyallomer tube (Seton Scientific). The sucrose shelf has two layers: 5 mL of 20% sucrose and 26 mL of 70% sucrose. 6 mL of clarified lysate was added gently atop the sucrose. This step has been performed with up to 8 mL of clarified lysate with 2 mLs less 70% sucrose being used. The sucrose shelf was centrifuged for 4 hours at 100,000×g in a JS-24 rotor at 4° C.

The sucrose shelf was fractionated from the top with a Piston Gradient FRACTIONATOR™ (BioComp) into 1 mL fractions. The VLPs of interest were found at the 20%:70% sucrose interface. The fractions that contained the VLPs were at a Brix value between 28.5 and 38.5 (generally between fractions 12 and 14). Westerns with a commercial antibody that recognizes both VP1 and VP2 (Santa Cruz BioTech cat# sc-71852) were performed to check for the location and concentration of the VLPs. This material was stored at 4° C., for at least 1 week with no protein degradation.

Capto Q Chromatography

A Western analysis with VP1/VP2 specific antibody (Santa Cruz BioTech cat# sc-71852) identified the fractions from the sucrose shelf that contained the greatest amount of protein. These fractions were either pooled or kept separate (based on a particular run). These fractions were diluted 1:4 in Buffer A (25 mM Tris, 100 mM NaCl pH 7.5) and loaded over a pre-washed and pre-equilibrated column at 6 cm/hr. The sucrose still present in the loaded protein partially prevented the protein from binding to the column at faster flow rates (i.e. 60 cm/hr). A NaCl gradient was used to elute the bound protein. Chromatography was run as follows:

Buffer A: 25 mM Tris, 100 mM NaCl pH 7.5; Buffer B: 25 mM Tris, 2 M NaCl pH 7.5; Washing: 5 CV with Buffer A; Gradient: 0-40% B (10 CV); Washing: 100% B 5CV; Flow: 0.2 ml/min. Fractions: 1 ml during elution. Pool from ~5% B to ~10% B. 11.6.

Buffer Exchange and Concentration

The Capto Q fractions were selected such that there was no band of greater or equal intensity to the VP1 band. These fractions were pooled and buffer exchanged into 25 mM Tris, 100 mM NaCl through a concentration and dilution method using 50 kDa cutoff Ultra 4 (Millipore-regenerated cellulose) concentrator. The final concentration was ~0.8 mg/mL. This process resulted in material that is >95% pure with low to not detectable levels of endotoxin. This material could be stored for >1 month prior to use. General yields were approximately 1.5 mg of purified material for 20 grams of biomass (the result of a 1 L shake flask).

TABLE 2

VP1/VP2 VLP production inoculation ranging.

| Lot | | |
|---|---|---|
| Inoc OD | .1 | .9 |
| Wet Weight per Liter (g) | 0.3 | 1.2 |
| Percent VP1 to VP2 | 1 | 6 |
| Yield (μg protein/g Wet Weight cells) | 6 | 8 |
| Purity | 95% | 95% |
| Endotoxin level (EU/10 μg dose) | .264 | .734 |

EXAMPLE 3

Analysis of Parvovirus B19 VLPs

VLP Purity

VLP purity was shown by Coomassie and western analysis. An example of a Coomassie stained SDS-PAGE and corresponding western is shown in FIG. 16

VLP Identification

VLP identification was carried out using two antibodies. One antibody (Santa Cruz BioTech cat# sc-71852) recognizes the common VP2 region and hence can identify both VP1 and VP2 (α-VP1/VP2 antibody). A second antibody (USBio P3113-81D) recognizes just the VP1 unique region and hence can identify VP1 only. A dimer of VP2 is still visible if the fractions are not fully boiled are reduced. As expected, the VP2 band is not present but the same VP1 band is visible when the α-VP1 antibody is used to probe the membrane.

VLP Characteristics

Figure 17:
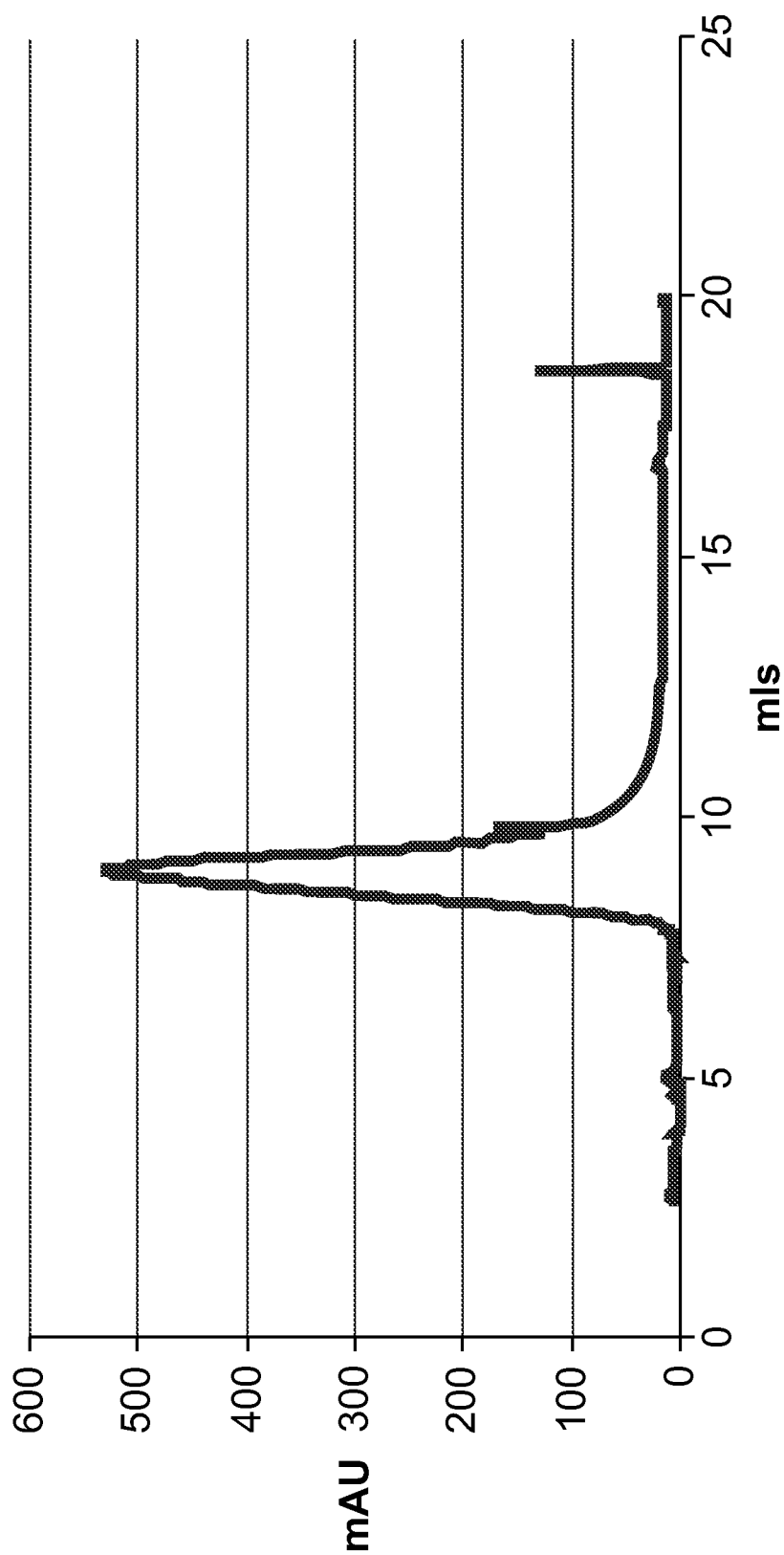

VLPs were selected using a sucrose shelf to remove protein not assembled into VLPs. The purified VLPs were analyzed for monomer content using SEC, native PAGE, DLS and electron microscopy. The results confirmed that the VLPs were >99% in a single large molecular weight species representative of a VLP (FIG. 17).

VLP Stability

The VLPs appeared stable in both MF59™ and in 25 mM Tris, 100 mM NaCl buffer for at least 3 months at 4° C. This was examined with Coomassie stained SDS-PAGE, Western with parvovirus specific antibodies, native PAGE and electron microscopy. Furthermore, the VLPs could be disrupted into monomers using 0.05% SDS but not 0.5% TRITON™ X-100.

Endotoxin Examination

The protein was analyzed for endotoxin with the Charles River Laboratories ENDOSAFE™-PTS system. This is a cartridge based system (Product Code PTS20) using *Limulus Amebocyte* Lysate detection of endotoxin. The assay was performed with Endotoxin Specific Buffer (Product Code BG120) as directed by the manufacturer to decrease spurious background signal generated by β-glucan (a component of the yeast cell wall) through a secondary activation pathway. The results from multiple assays demonstrated the range per 5 ug dose of material would be from 0.036 EU/dose to below the detectable limit of 0.013 EU/dose.

EXAMPLE 4

Mouse Immunogenicity Data

Immunogenicity was studied in Balb/c mice (n=10). Pre-immune serum was taken on the day before the first immunization. Immunizations were administered by IM at various concentrations (0.05, 0.5 or 5 μg) with different adjuvants (phosphate buffered saline, alum, or MF59™). Mice were bled on day 20 and received a second immunization on day 21. The mice were bled again three weeks after the second immunization (3wp2, day 41) and administered a third immunization on day 42. Serum samples were taken again on days 56 (2wp3-2 weeks post second) and 84 (6wp3-6 weeks post third).

Figure 12A:
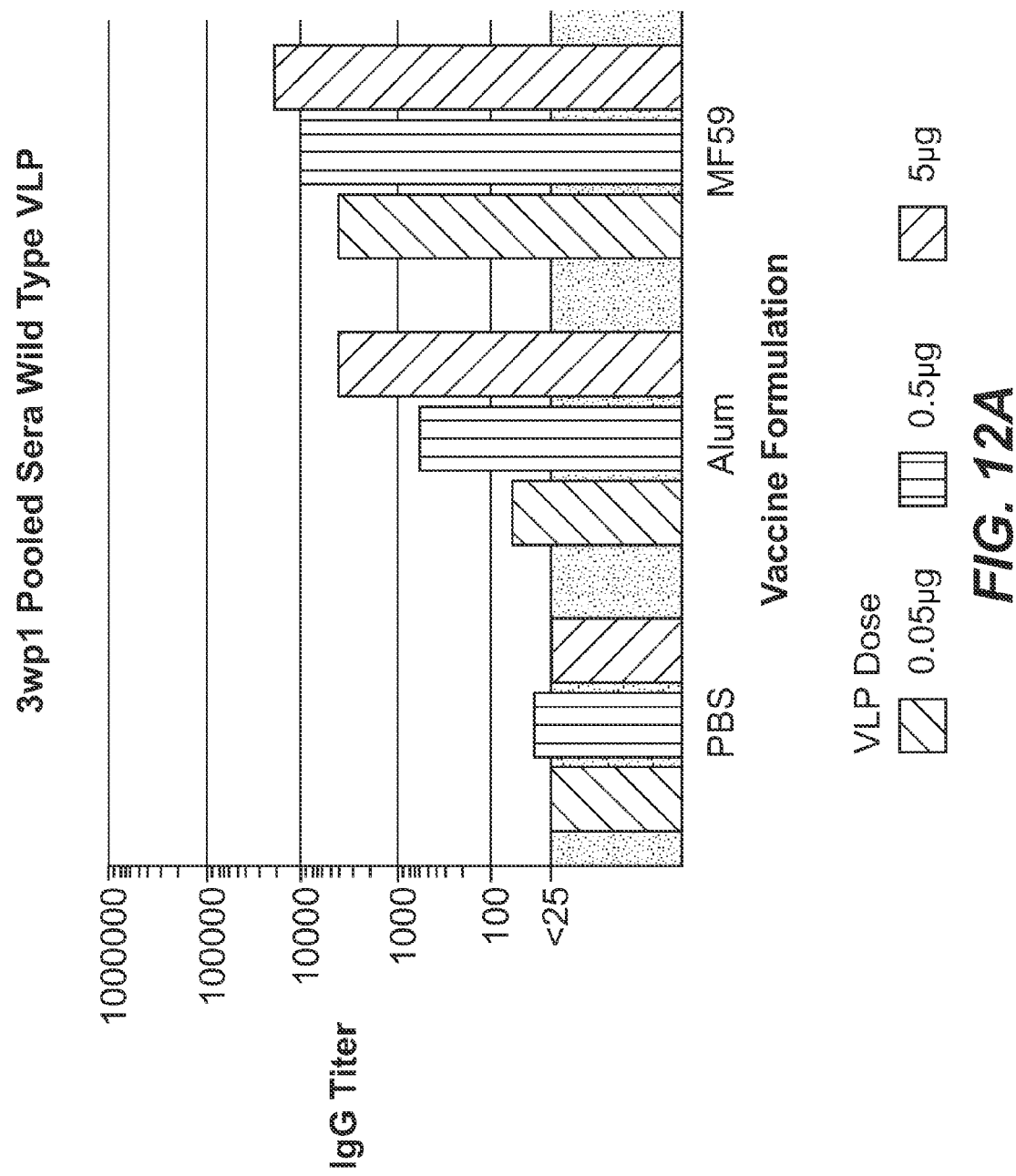
Figure 12C:
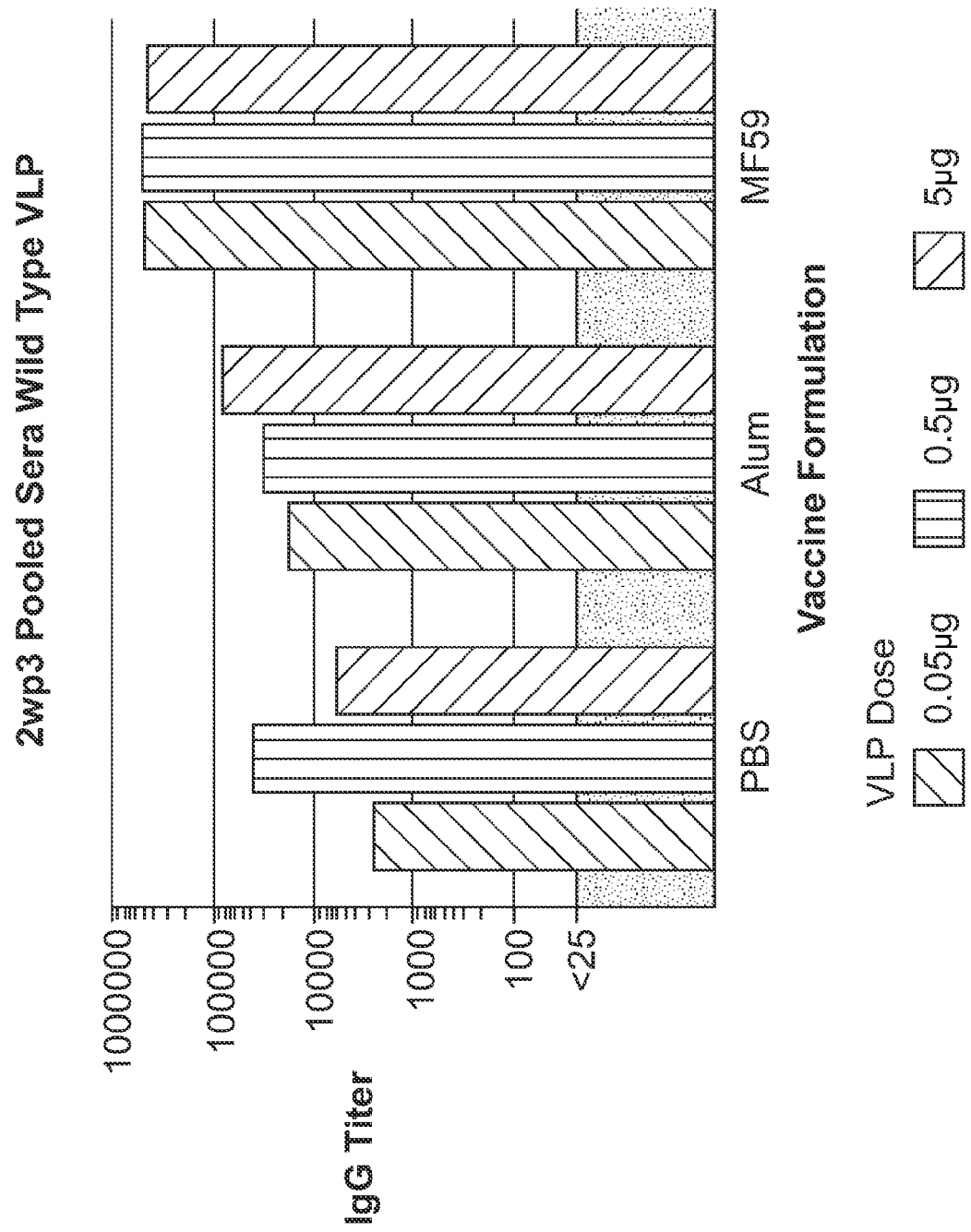
Figure 13:
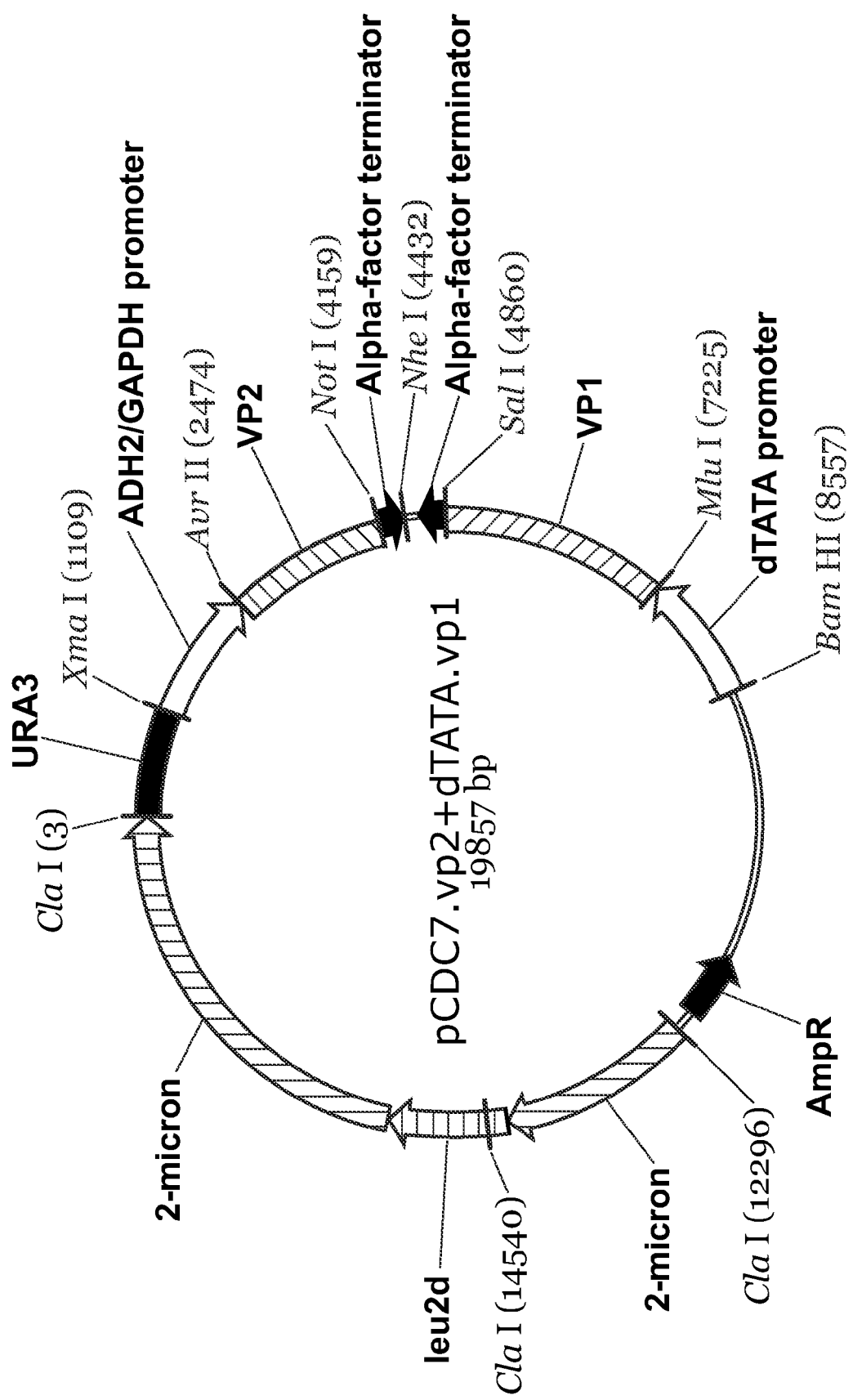
Figure 15:
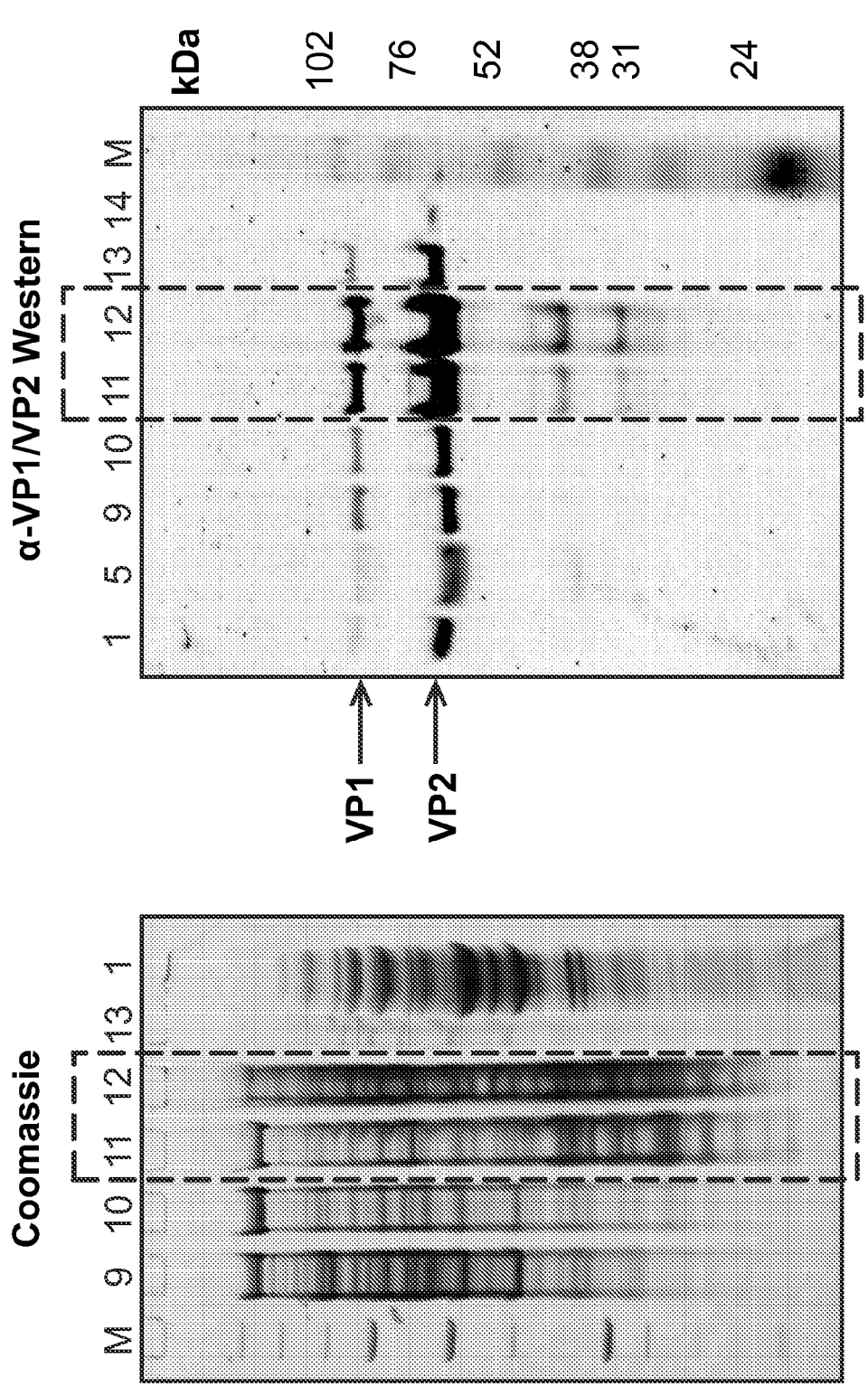

Sera for each vaccine group were pooled (n=5 for PBS vaccinated, n=10 for all other groups). IgG ELISAs were performed using plates coated with the parvovirus B19 VLPs (FIG. 12). Highest titers were demonstrated with the MF59™ formulations and were similar for each dose concentration.

EXAMPLE 5

Cell Based Neutralization

The neutralization assay was based on qRT-PCR and used erythroid progenitor cells that were CD36+ and globoside+ (the primary cell receptor) as the viral substrate. The assay measured the presence or absence of an RNA sequence that would only be present during infection. To determine neutralizing titers, the sera was pre-incubated with virus prior to mixing with the cells. The cells were harvested after 48 hours and probed for infection. Highest neutralizing titers for immunized mice were $6 \times 10^4$. Convalescent human sera tested in this assay gave a neutralizing titer (IC50) of $1 \times 10^4$.

TABLE 3

Table of ELISA titers (serum IgG) corresponding neutralizing titers from animal sera two weeks post third immunization.

| VLP (MF59 ™ ADJUVANTED) | Dose (ug) | ELISA titers (serum IgG) | Neutralizing titers (IC50) |
|---|---|---|---|
| VP2 alone | 0.05 | $5 \times 10^5$ | <10 |
| VP2 alone | 0.5 | $5 \times 10^5$ | <10 |
| VP2 alone | 5.0 | $5 \times 10^5$ | <10 |
| VP1/VP2 | 5.0 | $5 \times 10^5$ | $6 \times 10^4$ |

The invention claimed is:

1. A recombinant nucleic acid comprising a nucleotide sequence encoding parvoviris VP1 protein (VP1) operably linked to a first control element and a nucleotide sequence encoding parvovirus VP2 protein (VP2) operably linked to a second control element, wherein the recombinant nucleic acid comprises equivalent amounts of the nucleotide sequence encoding VP1 and the nucleotide sequence encoding VP2, the first control element is a weak promoter suitable for expression in a yeast cell and the second control element is a strong promoter suitable for expression in a yeast cell, wherein the second control element is an ADH/GAPDH promoter comprising SEQ ID NO: 19 and the first control element is a variant of said ADH/GAPDH promoter that results in decreased expression of VP1 relative VP2, wherein, when recombinant nucleic acid is expressed in a yeast cell, VP1 is produced in a lower abundance relative to VP2, and virus like particles (VLP) are formed that comprise VP1 and VP2.

2. The recombinant nucleic acid of claim 1, wherein the variant comprises a modification selected from the group consisting of: a deletion of at least a portion of the TATA box upstream of the nucleic acid encoding VP1, a deletion of a junction site upstream of the nucleic acid encoding VP1, introduction of a transcription start upstream of the nucleic acid encoding VP1, introduction of a transcription stop site upstream of the nucleic acid encoding VP1, and a combination thereof.

3. The recombinant nucleic acid of claim 1, wherein said nucleic acid is a nucleic acid selected from the group consisting of single stranded DNA, double stranded DNA, and RNA.

4. The recombinant nucleic acid of claim 3, wherein the recombinant nucleic acid comprises a plasmid.

5. The recombinant nucleic acid of claim 4, wherein the plasmid comprises a detectable marker.

6. A yeast cell comprising a recombinant nucleic acid according to claim 1.

7. The yeast cell of claim 6, wherein said recombinant nucleic acid is integrated into the genome of the yeast cell or is carried on an extra-chromosomal element.

8. The recombinant nucleic acid of claim 1, wherein the first control element comprises a nucleotide sequence selected from the group consisting of nucleotide 1-1379 of SEQ ID NO:20, SEQ ID NO:21, and nucleotide 7-24 of SEQ ID NO:22; and the second control element comprises SEQ ID NO:19.

* * * * *

SEQUENCE LISTING

```
<160> NUMBER OF SEQ ID NOS: 24

<210> SEQ ID NO 1
<211> LENGTH: 26
<212> TYPE: DNA
<213> ORGANISM: Artificial Sequence
<220> FEATURE:
<223> OTHER INFORMATION: Immunostimulatory nucleotide
<220> FEATURE:
<221> NAME/KEY: modified_base
<222> LOCATION: (1)..(1)
<223> OTHER INFORMATION: Inosine
<220> FEATURE:
<221> NAME/KEY: modified_base
<222> LOCATION: (3)..(3)
<223> OTHER INFORMATION: Inosine
<220> FEATURE:
<221> NAME/KEY: modified_base
<222> LOCATION: (5)..(5)
<223> OTHER INFORMATION: Inosine
<220> FEATURE:
<221> NAME/KEY: modified_base
<222> LOCATION: (7)..(7)
<223> OTHER INFORMATION: Inosine
<220> FEATURE:
<221> NAME/KEY: modified_base
<222> LOCATION: (9)..(9)
<223> OTHER INFORMATION: Inosine
<220> FEATURE:
<221> NAME/KEY: modified_base
<222> LOCATION: (11)..(11)
<223> OTHER INFORMATION: Inosine
<220> FEATURE:
<221> NAME/KEY: modified_base
<222> LOCATION: (13)..(13)
<223> OTHER INFORMATION: Inosine
<220> FEATURE:
<221> NAME/KEY: modified_base
<222> LOCATION: (15)..(15)
<223> OTHER INFORMATION: Inosine
<220> FEATURE:
<221> NAME/KEY: modified_base
```

```
<222> LOCATION: (17)..(17)
<223> OTHER INFORMATION: Inosine
<220> FEATURE:
<221> NAME/KEY: modified_base
<222> LOCATION: (19)..(19)
<223> OTHER INFORMATION: Inosine
<220> FEATURE:
<221> NAME/KEY: modified_base
<222> LOCATION: (21)..(21)
<223> OTHER INFORMATION: Inosine
<220> FEATURE:
<221> NAME/KEY: modified_base
<222> LOCATION: (23)..(23)
<223> OTHER INFORMATION: Inosine
<220> FEATURE:
<221> NAME/KEY: modified_base
<222> LOCATION: (25)..(25)
<223> OTHER INFORMATION: Inosine

<400> SEQUENCE: 1 ncncncnc ncncncncnc ncncnc                                       26

<210> SEQ ID NO 2
<211> LENGTH: 11
<212> TYPE: PRT
<213> ORGANISM: Artificial Sequence
<220> FEATURE:
<223> OTHER INFORMATION: Synthetic peptide

<400> SEQUENCE: 2

Lys Leu Lys Leu Leu Leu Leu Leu Lys Leu Lys
1               5                   10

<210> SEQ ID NO 3
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 3
ctgctgttga ttctgctgct agaattgctg atttcagata ctctcaatt            49

<210> SEQ ID NO 4
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 4
agatctacgc gtacaaaaca aaatgtctaa gaaatctggt aaatgg               46

<210> SEQ ID NO 5
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 5
agatctgtcg actcattaca atggatgaac tctagattta gcagtcc              47

<210> SEQ ID NO 6
<211> LENGTH: 48
<212> TYPE: DNA
<213> ORGANISM: Artificial Sequence
<220> FEATURE:
<223> OTHER INFORMATION: Synthetic oligonucleotide
```

```
<400> SEQUENCE: 6
agatctccta ggacaaaaca aaatgacatc tgttaattct gctgaagc                        48

<210> SEQ ID NO 7
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 7
agatctgcgg ccgctcatta caatggatga actctagatt tagcagtc                        48

<210> SEQ ID NO 8
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 8
agatctggat ccttcaatat gcgcacatac gctg                                       34

<210> SEQ ID NO 9
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 9
tctagaccta ggggaataat ttcagggaac tggtttcaac c                               41

<210> SEQ ID NO 10
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 10
ctagcattgt aattctgtaa atctatttct taaacttc                                   38

<210> SEQ ID NO 11
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 11
ttaaattcta cttttatagt tagtcttttt tttagtttta aaac                            44

<210> SEQ ID NO 12
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 12
accaagaact tagtttcgaa taaacacaca taaacaaaca                                 40

<210> SEQ ID NO 13
```

```
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 13
cgcgtgtttg tttatgtgtg tttattcgaa actaagttct tggtgtttta aaactaaaaa    60
aaagac                                                               66

<210> SEQ ID NO 14
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 14
taactataaa agtagaattt aagaagttta agaaatagat ttacagaatt acaatg        56

<210> SEQ ID NO 15
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 15
acaaaacaaa                                                           10

<210> SEQ ID NO 16
<211> LENGTH: 15872
<212> TYPE: DNA
<213> ORGANISM: Artificial Sequence
<220> FEATURE:
<223> OTHER INFORMATION: vector pCDC.7

<400> SEQUENCE: 16
atcgataagc ttttcaattc atcattttt ttttattctt ttttttgatt tcggtttcct     60
tgaaattttt ttgattcggt aatctccgaa cagaaggaag aacgaaggaa ggagcacaga   120
cttagattgg tatatatacg catatgtagt gttgaagaaa catgaaattg cccagtattc   180
ttaacccaac tgcacagaac aaaaacctgc aggaaacgaa gataaatcat gtcgaaagct   240
acatataagg aacgtgctgc tactcatcct agtcctgttg ctgccaagct atttaatatc   300
atgcacgaaa agcaaacaaa cttgtgtgct tcattggatg ttcgtaccac caaggaatta   360
ctggagttag ttgaagcatt aggtcccaaa atttgtttac taaaaacaca tgtggatatc   420
ttgactgatt tttccatgga gggcacagtt aagccgctaa aggcattatc cgccaagtac   480
aattttttac tcttcgaaga cagaaaattt gctgacattg gtaatacagt caaattgcag   540
tactctgcgg gtgtatacag aatagcagaa tgggcagaca ttacgaatgc acacggtgtg   600
gtgggcccag gtattgttag cggtttgaag caggcggcag aagaagtaac aaaggaacct   660
agaggccttt tgatgttagc agaattgtca tgcaagggct ccctatctac tggagaatat   720
actaagggta ctgttgacat tgcgaagagc gacaaagatt tgttatcgg ctttattgct   780 caaagagaca tgggtggaag agatgaaggt tacgattggt tgattatgac acccggtgtg   840
ggtttagatg acaagggaga cgcattgggt caacagtata gaaccgtgga tgatgtggtc   900
tctcacggat ctgacattat tattgttgga agaggactat tgcaaagggg aagggatgct   960
aaggtagagg gtgaacgtta cagaaaagca ggctgggaag catatttgag aagatgcggc  1020
```

```
cagcaaaact aaaaaactgt attataagta aatgcatgta tactaaactc acaaattaga   1080
gcttcaattt aattatatca gttattaccc gggttcaata tgcgcacata cgctgttatg   1140
ttcaaggtcc cttcgtttaa gaacgaaagc ggtcttcctt ttgagggatg tttcaagttg   1200
ttcaaatcta tcaaatttgc aaatccccag tctgtatcta gagcgttgaa tcggtgatgc   1260
gatttgttaa ttaaattgat ggtgtcacca ttaccaggtc tagatatacc aatggcaaac   1320
tgagcacaac ataccagtc cggatcaact ggcaccatct ctcccgtagt ctcatctaat   1380 tttcttccg gatgaggttc cagatatacc gcaacacctt tattatggtt ccctgaggg    1440 aataatagaa tgtcccattc gaatcacca attctaaacc tgggcgaatt gtatttcggg    1500
tttgttaact cgttccagtc aggaatgttc cacgtgaagc tatcttccag caaagtctcc   1560
acttcttcat caaattgtgg gagaatactc ccaatgctct tatctatggg acttccggga   1620
aacacagtac cgatacttcc caattcgtct tcagagctca ttgtttgttt gaagagacta   1680
atcaaagaat cgtttctca aaaaaattaa tatcttaact gatagtttga tcaaagggc    1740 aaaacgtagg ggcaaacaaa cggaaaaatc gtttctcaaa ttttctgatg ccaagaactc   1800
taaccagtct tatctaaaaa ttgccttatg atccgtctct ccggttacag cctgtgtaac   1860
tgattaatcc tgcctttcta atcaccattc taatgtttta attaagggat tttgtcttca   1920
ttaacggctt tcgctcataa aaatgttatg acgttttgcc cgcaggcggg aaaccatcca   1980
cttcacgaga ctgatctcct ctgccggaac accgggcatc tccaacttat aagttggaga   2040
aataagagaa tttcagattg agagaatgaa aaaaaaaac ccttagttca taggtccatt    2100
ctcttagcgc aactacagag aacaggggca caaacaggca aaaacgggc acaacctcaa    2160 tggagtgatg caacctgcct ggagtaaatg atgacacaag gcaattgacc cacgcatgta   2220
tctatctcat tttcttacac cttctattac cttctgctct ctctgatttg gaaaaagctg   2280
aaaaaaaagg ttgaaaccag ttccctgaaa ttattcccct acttgactaa taagtatata   2340
aagacggtag gtattgattg taattctgta aatctatttc ttaaacttct taaattctac   2400
ttttatagtt agtctttttt ttagttttaa aacaccaaga acttagtttc gaataaacac   2460
acataaacaa accctaggac ttctaagcgg ccgctttgtt cccactgtac ttttagctcg   2520
tacaaaatac aatatacttt tcatttctcc gtaaacaaca tgttttccca tgtaatatcc   2580
ttttctattt ttcgttccgt taccaacttt acacatactt tatatagcta ttcacttcta   2640
tacactaaaa aactaagaca atttaatt tgctgcctgc catatttcaa tttgttataa      2700
attcctataa tttatcctat tagtagctaa aaaagatga atgtgaatcg aatcctaaga    2760
gctagcgcta tatgcgttga tgcaatttct atgcgcaccc gttctcggag cactgtccga   2820
ccgctttggc cgccgcccag tcctgctcgc ttcgctactt ggagccacta tcgactacgc   2880
gatcatggcg accacacccg tcctgtggat cagatccaat tctcttagga ttcgattcac   2940
attcatcttt tttagctac taataggata aattatagga atttataaca aattgaaata    3000
tggcaggcag caaaattaaa attgtcttag ttttttagtg tatagaagtg aatagctata   3060
taaagtatgt gtaaagttgg taacggaacg aaaaatagaa aaggatatta catgggaaaa   3120
catgttgttt acggagaaat gaaaagtata ttgtattttg tacgagctaa agtacagtg    3180 ggaacaaagt cgactttcac aggcaacgcg tgtttgttta tgtgtgttta ttcgaaacta   3240
agttcttggt gttttaaaac taaaaaaaag actaactata aaagtagaat ttaagaagtt   3300
taagaaatag atttacagaa ttcaatcaa tacctaccgt ctttatatac ttattagtca    3360
```

```
agtagggaa taatttcagg gaactggttt caacctttt tttcagcttt ttccaaatca      3420
gagagagcag aaggtaatag aaggtgtaag aaaatgagat agatacatgc gtgggtcaat    3480
tgccttgtgt catcatttac tccaggcagg ttgcatcact ccattgaggt tgtgcccgtt    3540
ttttgcctgt ttgtgcccct gttctctgta gttgcgctaa gagaatggac ctatgaacta    3600
agggttttt tttttcattc tctcaatctg aaattctctt atttctccaa cttataagtt     3660
ggagatgccc ggtgttccgg cagaggagat cagtctcgtg aagtggatgg tttcccgcct    3720
gcgggcaaaa cgtcataaca ttttatgag cgaaagccgt taatgaagac aaaatccctt     3780
aattaaaaca ttagaatggt gattagaaag gcaggattaa tcagttacac aggctgtaac    3840
cggagagacg gatcataagg caattttag ataagactgg ttagagttct tggcatcaga     3900
aaatttgaga acgatttt ccgtttgttt gccctacgt tttgccctt tgatcaaact        3960
atcagttaag atattaattt ttttgagaaa acgattcttt gattagtctc ttcaaacaaa    4020
caatgagctc tgaagacgaa ttgggaagta tcggtactgt gtttcccgga agtcccatag    4080
ataagagcat tgggagtatt ctcccacaat ttgatgaaga agtggagact ttgctggaag    4140
atagcttcac gtggaacatt cctgactgga acgagttaac aaacccgaaa tacaattcgc    4200
ccaggtttag aattggtgat ttcgaatggg acattctatt attccctcag ggaaaccata    4260
ataaaggtgt tgcggtatat ctggaacctc atccggaaga aaaattagat gagactacgg    4320
gagagatggt gccagttgat ccggactggt attgttgtgc tcagtttgcc attggtatat    4380
ctagacctgg taatggtgac accatcaatt taattaacaa atcgcatcac cgattcaacg    4440
ctctagatac agactgggga tttgcaaatt tgatagattt gaacaacttg aaacatccct    4500
caaaaggaag accgctttcg ttcttaaacg aagggacctt gaacataaca gcgtatgtgc    4560
gcatattgaa ggatcctcga ccgatgccct tgagagcctt caacccagtc agctccttcc    4620
ggtgggcgcg gggcatgact atcgtcgccg cacttatgac tgtcttcttt atcatgcaac    4680
tcgtaggaca ggtgccggca gcgctctggg tcattttcgg cgaggaccgc tttcgctgga    4740
gcgcgacgat gatcggcctg tcgcttgcgg tattcggaat cttgcacgcc ctcgctcaag    4800
ccttcgtcac tggtcccgcc accaaacgtt tcggcgagaa gcaggccatt atcgccggca    4860
tggcggccga cgcgctgggc tacgtcttgc tggcgttcgc gacgcgaggc tggatggcct    4920
tccccattat gattcttctc gcttccggcg gcatcgggat gcccgcgttg caggccatgc    4980
tgtccaggca ggtagatgac gaccatcagg gacagcttca aggatcgctc gcggctctta    5040
ccagcctaac ttcgatcatt ggaccgctga tcgtcacggc gatttatgcc gcctcggcga    5100
gcacatggaa cgggttggca tggattgtag gcgccgccct ataccttgtc tgcctccccg    5160
cgttgcgtcg cggtgcatgg agccgggcca cctcgacctg aatggaagcc ggcggcacct    5220
cgctaacgga ttcaccactc caagaattgg agccaatcaa ttcttgcgga gaactgtgaa    5280
tgcgcaaacc aaccctggc agaacatatc catcgcgtcc gccatctcca gcagccgcac    5340
gcggcgcatc tcgggcagcg ttgggtcctg gccacgggtg cgcatgatcg tgctcctgtc    5400
gttgaggacc cggctaggct ggcggggttg ccttactggt tagcagaatg aatcaccgat    5460
acgcgagcga acgtgaagcg actgctgctg caaaacgtct gcgacctgag caacaacatg    5520
aatggtcttc ggtttccgtg tttcgtaaag tctggaaacg cggaagtcag cgccctgcac    5580
cattatgttc cggatctgca tcgcaggatg ctgctggcta ccctgtggaa cacctacatc    5640
tgtattaacg aagcgctggc attgaccctg agtgattttt ctctggtccc gccgcatcca    5700
taccgccagt tgtttaccct cacaacgttc cagtaaccgg gcatgttcat catcagtaac    5760
```

```
ccgtatcgtg agcatcctct ctcgtttcat cggtatcatt accccatga acagaaatcc     5820 cccttacacg gaggcatcag tgaccaaaca ggaaaaaacc gcccttaaca tggcccgctt     5880
tatcagaagc cagacattaa cgcttctgga gaaactcaac gagctggacg cggatgaaca     5940
ggcagacatc tgtgaatcgc ttcacgacca cgctgatgag ctttaccgca gctgcctcgc     6000
gcgtttcggt gatgacggtg aaaacctctg acacatgcag ctcccggaga cggtcacagc     6060
ttgtctgtaa gcgatgccg ggagcagaca agcccgtcag ggcgcgtcag cgggtgttgg     6120
cgggtgtcgg ggcgcagcca tgacccagtc acgtagcgat agcggagtgt atactggctt     6180
aactatgcgg catcagagca gattgtactg agagtgcacc atatgcggtg tgaaataccg     6240
cacagatgcg taaggagaaa ataccgcatc aggcgctctt ccgcttcctc gctcactgac     6300
tcgctgcgct cggtcgttcg gctgcggcga gcggtatcag ctcactcaaa ggcggtaata     6360
cggttatcca cagaatcagg ggataacgca ggaaagaaca tgtgagcaaa aggccagcaa     6420
aaggccagga accgtaaaaa ggccgcgttg ctggcgtttt tccataggct ccgcccccct     6480
gacgagcatc acaaaaatcg acgctcaagt cagaggtggc gaaacccgac aggactataa     6540
agataccagg cgtttccccc tggaagctcc ctcgtgcgct ctcctgttcc gaccctgccg     6600
cttaccggat acctgtccgc ctttctccct tcgggaagcg tggcgctttc tcatagctca     6660
cgctgtaggt atctcagttc ggtgtaggtc gttcgctcca agctgggctg tgtgcacgaa     6720
ccccccgttc agcccgaccg ctgcgcctta tccggtaact atcgtcttga gtccaacccg     6780
gtaagacacg acttatcgcc actggcagca gccactggta acaggattag cagagcgagg     6840
tatgtaggcg gtgctacaga gttcttgaag tggtggccta actacggcta cactagaagg     6900
acagtatttg gtatctgcgc tctgctgaag ccagttacct tcggaaaaag agttggtagc     6960
tcttgatccg gcaaacaaac caccgctggt agcggtggtt tttttgtttg caagcagcag     7020
attacgcgca gaaaaaaagg atctcaagaa gatcctttga tcttttctac ggggtctgac     7080
gctcagtgga acgaaaactc acgttaaggg attttggtca tgagattatc aaaaaggatc     7140
ttcacctaga tccttttaaa ttaaaaatga agttttaaat caatctaaag tatatatgag     7200
taaacttggt ctgacagtta ccaatgctta atcagtgagg cacctatctc agcgatctgt     7260
ctatttcgtt catccatagt tgcctgactc cccgtcgtgt agataactac gatacgggag     7320
ggcttaccat ctggccccag tgctgcaatg ataccgcgag acccacgctc accggctcca     7380
gatttatcag caataaacca gccagccgga agggccgagc gcagaagtgg tcctgcaact     7440
ttatccgcct ccatccagtc tattaattgt tgccgggaag ctagagtaag tagttcgcca     7500
gttaatagtt tgcgcaacgt tgttgccatt gctgcaggca tcgtggtgtc acgctcgtcg     7560
tttggtatgg cttcattcag ctccggttcc caacgatcaa ggcgagttac atgatccccc     7620
atgttgtgca aaaaagcggt tagctccttc ggtcctccga tcgttgtcag aagtaagttg     7680
gccgcagtgt tatcactcat ggttatggca gcactgcata attctcttac tgtcatgcca     7740
tccgtaagat gcttttctgt gactggtgag tactcaacca agtcattctg agaatagtgt     7800
atgcggcgac cgagttgctc ttgcccggcg tcaacacggg ataataccgc gccacatagc     7860
agaactttaa aagtgctcat cattggaaaa cgttcttcgg ggcgaaaact ctcaaggatc     7920
ttaccgctgt tgagatccag ttcgatgtaa cccactcgtg cacccaactg atcttcagca     7980
tcttttactt tcaccagcgt ttctgggtga gcaaaaacag gaaggcaaaa tgccgcaaaa     8040
aagggaataa gggcgacacg gaaatgttga atactcatac tcttcctttt tcaatattat     8100
```

```
tgaagcattt atcagggtta ttgtctcatg agcggataca tatttgaatg tatttagaaa    8160
aataaacaaa tagggttcc gcgcacattt ccccgaaaag tgccacctga cgtctaagaa     8220
accattatta tcatgacatt aacctataaa ataggcgta tcacgaggcc ctttcgtctt     8280
caagaattct catgtttgac agcttatcat cgatccactt gtatatttgg atgaatttt     8340 gaggaattct gaaccagtcc taaaacgagt aaataggacc ggcaattctt caagcaataa    8400
acaggaatac caattattaa aagataactt agtcagatcg tacaataaag ctttgaagaa    8460
aaatgcgcct tattcaatct ttgctataaa aaatggccca aaatctcaca ttggaagaca    8520
tttgatgacc tcatttcttt caatgaaggg cctaacggag ttgactaatg ttgtgggaaa    8580
ttggagcgat aagcgtgctt ctgccgtggc caggacaacg tatactcatc agataacagc    8640
aatacctgat cactacttcg cactagtttc tcggtactat gcatatgatc caatatcaaa    8700
ggaaatgata gcattgaagg atgagactaa tccaattgag gagtggcagc atatagaaca    8760
gctaaagggt agtgctgaag gaagcatacg atacccgca tggaatggga taatatcaca    8820
ggaggtacta gactaccttt catcctacat aaatagacgc atataagtac gcatttaagc    8880
ataaacacgc actatgccgt tcttctcatg tatatatata tacaggcaac acgcagatat    8940
aggtgcgacg tgaacagtga gctgtatgtg cgcagctcgc gttgcatttt cggaagcgct    9000
cgttttcgga aacgctttga agttcctatt ccgaagttcc tattctctag aaagtatagg    9060
aacttcagag cgcttttgaa aaccaaaagc gctctgaaga cgcacttttca aaaaaccaaa   9120 aacgcaccgg actgtaacga gctactaaaa tattgcgaat accgcttcca caaacattgc    9180 tcaaagtat ctctttgcta tatatctctg tgctatatcc ctatataacc tacccatcca    9240
cctttcgctc cttgaacttg catctaaact cgacctctac attttttatg tttatctcta    9300
gtattactct ttagacaaaa aaattgtagt aagaactatt catagagtga atcgaaaaca    9360
atacgaaaat gtaaacattt cctatacgta gtatatagag acaaaataga gaaaccgtt    9420 cataattttc tgaccaatga agaatcatca acgctatcac tttctgttca caagtatgc    9480 gcaatccaca tcggtataga atataatcgg ggatgccttt atcttgaaaa aatgcacccg    9540
cagcttcgct agtaatcagt aaacgcggga agtggagtca ggcttttttt atggaagaga    9600
aaatagacac caaagtagcc ttcttctaac cttaacggac ctacagtgca aaaagttatc    9660
aagagactgc attatagagc gcacaaagga gaaaaaagt aatctaagat gctttgttag     9720
aaaaatagcg ctctcgggat gcattttgt agaacaaaaa agaagtatag attctttgtt     9780
ggtaaaatag cgctctcgcg ttgcatttct gttctgtaaa aatgcagctc agattctttg    9840
tttgaaaaat tagcgctctc gcgttgcatt tttgttttac aaaaatgaag cacagattct    9900
tcgttggtaa aatagcgctt tcgcgttgca tttctgttct gtaaaatgc agctcagatt     9960 ctttgtttga aaaattagcg ctctcgcgtt gcatttttgt tctacaaaat gaagcacaga   10020
tgcttcgtta acaaagatat gctattgaag tgcaagatgg aaacgcagaa aatgaaccgg   10080
ggatgcgacg tgcaagatta cctatgcaat agatgcaata gtttctccag gaaccgaaat   10140
acatacattg tcttccgtaa agcgctagac tatatattat tatacaggtt caaatatact   10200
atctgtttca gggaaaactc ccaggttcgg atgttcaaaa ttcaatgatg ggtaacaagt   10260
acgatcgtaa atctgtaaaa cagtttgtcg gatattaggc tgtatctcct caaagcgtat   10320
tcgaatatca ttgagaagct gcattttttt tttttttttt tttttttttt tttatatat   10380 atttcaagga tataccattg taatgtctgc ccctaagaag atcgtcgttt tgccaggtga   10440
ccacgttggt caagaaatca cagccgaagc cattaaggtt cttaaagcta tttctgatgt   10500
```

```
tcgttccaat gtcaagttcg atttcgaaaa tcatttaatt ggtggtgctg ctatcgatgc   10560
tacaggtgtt ccacttccag atgaggcgct ggaagcctcc aagaaggctg atgccgtttt   10620
gttaggtgct gtgggtggtc ctaaatgggg taccggtagt gttagacctg aacaaggttt   10680
actaaaaatc cgtaaagaac ttcaattgta cgccaactta agaccatgta actttgcatc   10740
cgactctctt ttagacttat ctccaatcaa gccacaattt gctaaaggta ctgacttcgt   10800
tgttgttaga gaattagtgg gaggtattta ctttggtaag agaaaggaag acgatggtga   10860
tggtgtcgct tgggatagtg aacaatacac cgttccagaa gtgcaaagaa tcacaagaat   10920
ggccgctttc atggccctac aacatgagcc accattgcct atttggtcct ggataaagc    10980 taatgttttg gcctcttcaa gattatggag aaaaactgtg gaggaaacca tcaagaacga   11040
attccctaca ttgaaagttc aacatcaatt gattgattct gccgccatga tcctagttaa   11100
gaacccaacc cacctaaatg gtattataat caccagcaac atgtttggtg atatcatctc   11160
cgatgaagcc tccgttatcc caggctcctt gggtttgttg ccatctgcgt ccttggcctc   11220
tttgccagac aagaacaccg catttggttt gtacgaacca tgccatggtt ccgctccaga   11280
tttgccaaag aataaggtca accctatcgc cactatcttg tctgctgcaa tgatgttgaa   11340
attgtcattg aacttgcctg aagaaggtaa agccattgaa gatgcagtta aaaaggtttt   11400
ggatgcaggt atcagaactg gtgatttagg tggttccaac agtaccaccg aagtcggtga   11460
tgctgtcgcc gaagaagtta agaaaatcct tgcttaaaaa gattctcttt ttttatgata   11520
tttgtaccaa aaaaaaaaaa aaaaaaaaaa aaaaaaaaaa aaaaaaaaaa aaaaaaaaaa   11580
atgcagcgtc acatcggata taatgatgg cagccattgt agaagtgcct tttgcatttc    11640
tagtctcttt ctcggtctag ctagttttac tacatcgcga agatagaatc ttagatcaca   11700
ctgcctttgc tgagctggat caatagagta acaaaagagt ggtaaggcct cgttaaagga   11760
caaggacctg agcggaagtg tatcgtacag tagacggagt atactagtat agtctatagt   11820
ccgtggaatt ctaagtgcca gctttataat gtcattctcc ttactacaga cccgcctgaa   11880
agtagacaca tcatcatcag taagctttga caaaaagcat tgagtagcta actcttctat   11940
gcaatctata gctgtttat aaggcattca atggacagat tgaggttttt gaaacatact    12000
agtgaaatta gccttaatcc cttctcgaag ttaatcatgc attatggtgt aaaaaatgca   12060
actcgcgttg ctctacttt tccccgaattt ccaaatacgc agctggggtg attgctcgat   12120
ttcgtaacga aagttttgtt tataaaaacc gcgaaaacct tctgtaacag atagattttt   12180
acagcgctga tatacaatga catcagctgt aatggaaaat aactgaaata tgaatggcga   12240
gagactgctt gcttgtatta agcaatgtat tatgcagcac ttccaaccta tggtgtacga   12300
tgaaagtagg tgtgtaatcg agacgacaag ggggactttt ccagttcctg acaattataa   12360
gaaatacaaa acgttagcat ttgcatttgt tggacatgta ctgaatacag acgacacacc   12420
ggtaattgaa aaagaactgg attggcctga tcctgcacta gtgtacaata caattgtcga   12480
tcgaatcata aatcacccag aattatcaca gtttatatcg gttgcattta ttagtcagtt   12540
aaaggccacc atcggagagg gtttagatat taatgtaaaa ggcacgctaa accgcagggg   12600
aaagggtatc agaaggccta aaggcgtatt ttttagatac atggaatctc catttgtcaa   12660
tacaaaggtc actgcattct tctcttatct tcgagattat aataaaattg cctcagaata   12720
tcacaataat actaaattca ttctcacgtt ttcatgtcaa gcatattggg catctggccc   12780
aaacttctcc gccttgaaga atgttattag gtgctccata attcatgaat acatttctaa   12840
```

```
gtttgtggaa agagaacagg ataaaggtca tataggagat caggagctac cgcctgaaga    12900
ggacccttct cgtgaactaa acaatgtaca acatgaagtc aatagtttaa cggaacaaga    12960
tgcggaggcg gatgaaggat tgtggggtga aatagattca ttatgtgaaa aatggcagtc    13020
tgaagcggaa gatcaaactg aggcggagat aatagccgac aggataattg gaaatagcca    13080
gaggatggcg aacctcaaaa ttcgtcgtac aaagttcaaa agtgtcttgt atcatatact    13140
aaaggaacta attcaatctc agggaaccgt aaaggtttat cgcggtagta gttttttcaca   13200 cgattcgata aagataagct tacattatga agagcagcat attacagccg tatgggtcta    13260
cttgacagta aaatttgaag agcattggaa gcctgttgat gtagaggtcg agtttagatg    13320
caagttcaag gagcgaaagg tggatgggta ggttatatag ggatatagca cagagatata    13380
tagcaaagag atacttttga gcaatgtttg tggaagcggt attcgcaata ttttagtagc    13440
tcgttacagt ccggtgcgtt tttggttttt tgaaagtgcg tcttcagagc gcttttggtt    13500
ttcaaaagcg ctctgaagtt cctatacttt ctagagaata ggaacttcgg aataggaact    13560
tcaaagcgtt tccgaaaacg agcgcttccg aaaatgcaac gcgagctgcg cacatacagc    13620
tcactgttca cgtcgcacct atatctgcgt gttgcctgta tatatatata catgagaaga    13680
acggcatagt gcgtgtttat gcttaaatgc gtacttatat gcgtctattt atgtaggatg    13740
aaaggtagtc tagtacctcc tgtgatatta tcccattcca tgcggggtat cgtatgcttc    13800
cttcagcact acccttttagc tgttctatat gctgccactc ctcaattgga ttagtctcat    13860
ccttcaatgc tatcatttcc tttgatattg gatcataccc tagaagtatt acgtgatttt    13920 ctgccccctta ccctcgttgc tactctcctt tttttcgtgg gaaccgcttt agggccctca    13980
gtgatggtgt tttgtaattt atatgctcct cttgcatttg tgtctctact tcttgttcgc    14040
ctggagggaa cttcttcatt tgtattagca tggttcactt cagtccttcc ttccaactca    14100 ctctttttt gctgtaaacg attctctgcc gccagttcat tgaaactatt gaatatatcc    14160
tttagagatt ccgggatgaa taaatcacct attaaagcag cttgacgatc tggtggaact    14220
aaagtaagca attgggtaac gacgcttacg agcttcataa catcttcttc cgttggagct    14280
ggtgggacta ataactgtgt acaatccatt tttctcatga gcatttcggt agctctcttc    14340
ttgtctttct cgggcaatct tcctattatt atagcaatag atttgtatag ttgcttttcta   14400 ttgtctaaca gcttgttatt ctgtagcatc aaatctatgg cagcctgact tgcttcttgt    14460
gaagagagca taccatttcc aatcgaatca aaccttcct taaccatctt cgcagcaggc     14520
aaaattacct cagcactgga gtcagaagat acgctggaat cttctgcgct agaatcaaga    14580
ccatacggcc taccggttgt gagagattcc atgggcctta tgacatatcc tggaaagagt    14640
agctcatcag acttacgttt actctctata tcaatatcta catcaggagc aatcatttca    14700
ataaacagcc gacatacatc ccagacgcta taagctgtac gtgcttttac cgtcagattc    14760
ttggctgttt caatgtcgtc cattttggtt ttcttttacc agtattgttc gtttgataat    14820
gtattcttgc ttattacatt ataaaatctg tgcagatcac atgtcaaaac aactttttat    14880
cacaagatag taccgcaaaa cgaacctgcg ggccgtctaa aaattaagga aaagcagcaa    14940
aggtgcattt ttaaaatatg aaatgaagat accgcagtac caattatttt cgcagtacaa    15000
ataatgcgcg gccggtgcat ttttcgaaag aacgcgagac aaacaggaca attaaagtta    15060 gttttttcgag ttagcgtgtt tgaatactgc aagatacaag ataaatagag tagttgaaac   15120
tagatatcaa ttgcacacaa gatcggcgct aagcatgcca caatttgata tattatgtaa    15180
aacaccacct aaggtgcttg ttcgtcagtt tgtggaaagg tttgaaagac cttcaggtga    15240
```
gaaaatagca ttatgtgctg ctgaactaac ctatttatgt tggatgatta cacataacgg 15300
aacagcaatc aagagagcca cattcatgag ctataatact atcataagca attcgctgag 15360
tttcgatatt gtcaataaat cactccagtt taaatacaag acgcaaaaag caacaattct 15420
ggaagcctca ttaaagaaat tgattcctgc ttgggaattt acaattattc cttactatgg 15480
acaaaaacat caatctgata tcactgatat tgtaagtagt ttgcaattac agttcgaatc 15540
atcggaagaa gcagataagg gaaatagcca cagtaaaaaa atgcttaaag cacttctaag 15600
tgagggtgaa agcatctggg agatcactga gaaaatacta aattcgtttg agtatacttc 15660
gagatttaca aaaacaaaaa ctttatacca attcctcttc ctagctactt tcatcaattg 15720
tggaagattc agcgatatta agaacgttga tccgaaatca tttaaattag tccaaaataa 15780
gtatctggga gtaataatcc agtgtttagt gacagagaca aagacaagcg ttagtaggca 15840
catatacttc tttagcgcaa ggggtaggta gc 15872

<210> SEQ ID NO 17
<211> LENGTH: 2371
<212> TYPE: DNA
<213> ORGANISM: Artificial Sequence
<220> FEATURE:
<223> OTHER INFORMATION: optimized parvovirus B19 VP1

<400> SEQUENCE: 17
acgcgtacaa aacaaaatgt ctaagaaatc tggtaaatgg tgggaatctg atgataaatt 60
tgctaaggct gtttaccaac aatttgttga attttacgaa aaggttactg gtactgattt 120
ggaattgatt caaattttga aggatcatta caacatttct ttggataatc cattggaaaa 180
tccatcttca ttgtttgatt tggttgctag aattaagaac aacttgaaga actctccaga 240
tttgtattct catcatttcc aatctcatgg tcaattgtct gatcatccac atgctttatc 300
ttcatcttca tctcatgctg aaccaagagg tgaaaatgct gttttatctt ctgaagattt 360
gcataaacca ggtcaagttt ctgttcaatt gccaggtact aattacgttg gtccaggtaa 420
tgaattgcaa gctggtccac cacaatctgc tgttgattct gctgctagaa ttcatgattt 480
cagatactct caattggcta agttgggtat taatccatat actcattgga ctgttgctga 540
tgaagaattg ttgaagaaca ttaagaatga aactggtttt caagctcaag ttgttaaaga 600
ttacttcact ttgaaaggtg ctgctgctcc agttgctcat tttcaaggtt ctttgccaga 660
agttccagct tataacgctt ctgaaaaata tccatctatg acatctgtta attctgctga 720
agcatctact ggtgcaggtg gaggtggttc taattctgtt aaatctatgt ggtctgaagg 780
tgctactttt tctgctaatt cagttacttg tactttctct agacaattct tgattccata 840
tgatccagaa catcattaca aagttttttc accagctgct tcatcttgtc ataatgcttc 900
aggtaaagaa gctaaggttt gtactatttc tccaattatg ggttattcta ctccttggag 960
atacttggat tttaatgctt tgaacttgtt tttttctcca ttggaatttc aacatttgat 1020
tgaaaactac ggttctattg ctccagatgc tttgactgtt actatttctg aaattgctgt 1080
taaggatgtt actgataaaa caggtggtgg tgttcaagtt actgattcta ctactggtag 1140
attgtgcatg ttggttgatc atgaatacaa atacccatac gttttgggtc aaggtcaaga 1200
tactttggct ccagaattgc caatttgggt ttattttcca ccacaatacg cttatttgac 1260
tgttggtgat gttaatactc aaggtatttc tggtgattct aaaaagttgg cttctgaaga 1320
atctgctttt tacgttttgg aacattcttc ttttcaattg ttgggtactg gtggtactgc 1380

```
ttctatgtct tacaaatttc caccagttcc acctgaaaat ttggaaggtt gttctcaaca   1440
tttttacgaa atgtacaatc cattgtatgg ttctagattg ggtgttccag atactttggg   1500
tggtgatcca aaatttagat ctttgactca tgaagatcat gctattcaac cacaaaattt   1560
catgccaggt ccattggtta attctgtttc tactaaagaa ggtgattctt ctaatacagg   1620
tgctggtaaa gcattgactg gtttgtctac tggtacttct caaaacacta gaatttcttt   1680
aagaccaggt ccagtttcac aaccatatca tcattgggat actgataagt acgttactgg   1740
tattaatgct atttcacatg gtcaaactac ttatggtaat gctgaagata aagaatatca   1800
acaaggtgtt ggtagatttc caaacgaaaa agaacaattg aaacaattgc aaggtttgaa   1860
tatgcatact tactttccaa acaaaggtac tcaacaatac actgatcaaa ttgaaagacc   1920
attgatggtt ggttctgttt ggaatagaag agctttgcat tatgaatctc aattgtggtc   1980
taagattcca aatttagatg attctttcaa gactcaattt gctgctttgg gtggttgggg   2040
tttgcatcaa cctccaccac aaattttctt gaagattttg ccacaatctg gtccaattgg   2100
tggtattaaa tctatgggta ttactacttt ggttcaatat gctgttggta ttatgactgt   2160
tacaatgact tttaagttgg gtccaagaaa agctacaggt agatggaatc cacaaccagg   2220
tgtttatcca ccacatgctg ctggtcattt gccttacgtt ttgtatgatc caactgctac   2280
tgatgctaaa caacatcata gacatggtta tgaaaaacct gaagaattgt ggactgctaa   2340
atctagagtt catccattgt aatgagtcga c                                  2371
```

<210> SEQ ID NO 18
<211> LENGTH: 1692
<212> TYPE: DNA
<213> ORGANISM: Artificial Sequence
<220> FEATURE:
<223> OTHER INFORMATION: optimized parvovirus B19 VP2

<400> SEQUENCE: 18

```
cctaggacaa aacaaaatga catctgttaa ttctgctgaa gcatctactg gtgcaggtgg     60
aggtggttct aattctgtta aatctatgtg gtctgaaggt gctacttttt ctgctaattc    120
agttacttgt actttctcta gacaattctt gattccatat gatccagaac atcattacaa    180
agtttttttca ccagctgctt catcttgtca taatgcttca ggtaaagaag ctaaggtttg    240
tactatttct ccaattatgg gttattctac tccttggaga tacttggatt ttaatgcttt    300
gaacttgttt ttttctccat tggaatttca acatttgatt gaaaactacg gttctattgc    360
tccagatgct ttgactgtta ctatttctga aattgctgtt aaggatgtta ctgataaaac    420
aggtggtggt gttcaagtta ctgattctac tactggtaga ttgtgcatgt tggttgatca    480
tgaatacaaa tacccatacg ttttgggtca aggtcaagat actttggctc cagaattgcc    540
aatttgggtt tattttccac cacaatacgc ttatttgact gttggtgatg ttaatactca    600
aggtatttct ggtgattcta aaaagttggc ttctgaagaa tctgcttttt acgttttgga    660
acattcttct tttcaattgt tgggtactgg tggtactgct tctatgtctt acaaatttcc    720
accagttcca cctgaaaatt tggaaggttg ttctcaacat ttttacgaaa tgtacaatcc    780
attgtatggt tctagattgg gtgttccaga tactttgggt ggtgatccaa aatttagatc    840
tttgactcat gaagatcatg ctattcaacc acaaaatttc atgccaggtc cattggttaa    900
ttctgtttct actaaagaag gtgattcttc taatacaggt gctggtaaag cattgactgg    960
tttgtctact ggtacttctc aaaacactag aatttcttta agaccaggtc cagtttcaca   1020
accatatcat cattgggata ctgataagta cgttactggt attaatgcta tttcacatgg   1080
```

```
tcaaactact tatggtaatg ctgaagataa agaatatcaa caaggtgttg gtagatttcc    1140
aaacgaaaaa gaacaattga acaattgca aggtttgaat atgcatactt actttccaaa    1200
caaaggtact caacaataca ctgatcaaat tgaaagacca ttgatggttg gttctgtttg    1260
gaatagaaga gctttgcatt atgaatctca attgtggtct aagattccaa atttagatga    1320 ttcttcaag actcaatttg ctgctttggg tggttggggt ttgcatcaac ctccaccaca    1380
aattttcttg aagattttgc cacaatctgg tccaattggt ggtattaaat ctatgggtat    1440
tactactttg gttcaatatg ctgttggtat tatgactgtt acaatgactt ttaagttggg    1500
tccaagaaaa gctacaggta gatggaatcc acaaccaggt gtttatccac acatgctgc     1560 tggtcatttg ccttacgttt tgtatgatcc aactgctact gatgctaaac aacatcatag    1620
acatggttat gaaaaacctg aagaattgtg gactgctaaa tctagagttc atccattgta    1680
atgagcggcc gc                                                        1692
```

<210> SEQ ID NO 19
<211> LENGTH: 1371
<212> TYPE: DNA
<213> ORGANISM: Artificial Sequence
<220> FEATURE:
<223> OTHER INFORMATION: ADH2/GAPDH promoter

<400> SEQUENCE: 19

```
ggatccttca atatgcgcac atacgctgtt atgttcaagg tcccttcgtt taagaacgaa      60
agcggtcttc cttttgaggg atgtttcaag ttgttcaaat ctatcaaatt tgcaaatccc     120
cagtctgtat ctagagcgtt gaatcggtga tgcgatttgt taattaaatt gatggtgtca     180
ccattaccag gtctagatat accaatggca aactgagcac aacaatacca gtccggatca    240
actggcacca tctctcccgt agtctcatct aattttctt ccggatgagg ttccagatat     300
accgcaacac ctttattatg gtttccctga gggaataata gaatgtccca ttcgaaatca    360
ccaattctaa acctgggcga attgtatttc gggtttgtta actcgttcca gtcaggaatg    420
ttccacgtga agctatcttc cagcaaagtc tccacttctt catcaaattg tgggagaata    480
ctcccaatgc tcttatctat gggacttccg ggaaacacag taccgatact tcccaattcg    540
tcttcagagc tcattgtttg tttgaagaga ctaatcaaag aatcgttttc tcaaaaaaat    600
taatatctta actgatagtt tgatcaaagg ggcaaacgt aggggcaaac aaacggaaaa     660
atcgtttctc aaattttctg atgccaagaa ctctaaccag tcttatctaa aaattgcctt    720
atgatccgtc tctccggtta cagcctgtgt aactgattaa tcctgccttt ctaatcacca    780
ttctaatgtt ttaattaagg gattttgtct tcattaacgg ctttcgctca taaaatgtt    840 atgacgtttt gcccgcaggc gggaaaccat ccacttcacg agactgatct cctctgccgg    900
aacaccgggc atctccaact ataagttgg agaaataaga gaatttcaga ttgagagaat    960
gaaaaaaaaa aaacccttagt tcataggtcc attctcttag cgcaactaca gagaacaggg   1020
gcacaaacag gcaaaaaacg ggcacaacct caatggagtg atgcaacctg cctggagtaa   1080
atgatgacac aaggcaattg acccacgcat gtatctatct cattttctta caccttctat   1140
taccttctgc tctctctgat ttggaaaaag ctgaaaaaaa aggttgaaac cagttccctg   1200
aaattattcc cctacttgac taataagtat ataaagacgg taggtattga ttgtaattct   1260
gtaaatctat ttcttaaact tcttaaattc tactttata gttagtcttt tttttagttt    1320
taaaacacca agaacttagt ttcgaataaa cacacataaa caaacaagct t             1371
```

<210> SEQ ID NO 20
<211> LENGTH: 1382
<212> TYPE: DNA
<213> ORGANISM: Artificial Sequence
<220> FEATURE:
<223> OTHER INFORMATION: delta As version of the ADH2/GAPDH promoter

<400> SEQUENCE: 20

| | | | | | |
|---|---|---|---|---|---|
| ggatccttca | atatgcgcac | atacgctgtt | atgttcaagg | tcccttcgtt | taagaacgaa | 60 |
| agcggtcttc | cttttgaggg | atgtttcaag | ttgttcaaat | ctatcaaatt | tgcaaatccc | 120 |
| cagtctgtat | ctagagcgtt | gaatcggtga | tgcgatttgt | taattaaatt | gatggtgtca | 180 |
| ccattaccag | gtctagatat | accaatggca | aactgagcac | aacaatacca | gtccggatca | 240 |
| actggcacca | tctctcccgt | agtctcatct | aattttttctt | ccggatgagg | ttccagatat | 300 |
| accgcaacac | ctttattatg | gtttccctga | gggaataata | gaatgtccca | ttcgaaatca | 360 |
| ccaattctaa | acctgggcga | attgtatttc | gggtttgtta | actcgttcca | gtcaggaatg | 420 |
| ttccacgtga | agctatcttc | cagcaaagtc | tccacttctt | catcaaattg | tgggagaata | 480 |
| ctcccaatgc | tcttatctat | gggacttccg | ggaaacacag | taccgatact | tcccaattcg | 540 |
| tcttcagagc | tcattgtttg | tttgaagaga | ctaatcaaag | aatcgttttc | tcaaaaaaat | 600 |
| taatatctta | actgatagtt | tgatcaaagg | ggcaaaacgt | aggggcaaac | aaacggaaaa | 660 |
| atcgtttctc | aaattttctg | atgccaagaa | ctctaaccag | tcttatctaa | aaattgcctt | 720 |
| atgatccgtc | tctccggtta | cagcctgtgt | aactgattaa | tcctgccttt | ctaatcacca | 780 |
| ttctaatgtt | ttaattaagg | gattttgtct | tcattaacgg | ctttcgctca | taaaaatgtt | 840 |
| atgacgtttt | gcccgcaggc | gggaaaccat | ccacttcacg | agactgatct | cctctgccgg | 900 |
| aacaccgggc | atctccaact | tataagttgg | agaaataaga | gaatttcaga | ttgagagaat | 960 |
| gaaaaaaaa | aaccccttagt | tcataggtcc | attctcttag | cgcaactaca | gagaacaggg | 1020 |
| gcacaaacag | gcaaaaaacg | ggcacaacct | caatggagtg | atgcaacctg | cctggagtaa | 1080 |
| atgatgacac | aaggcaattg | acccacgcat | gtatctatct | catttctta | caccttctat | 1140 |
| taccttctgc | tctctctgat | ttggaaaaag | ctgaaaaaaa | aggttgaaac | cagttccctg | 1200 |
| aaattattcc | cctacttgac | taataagtat | ataaagacgg | taggtattga | ttgtaattct | 1260 |
| gtaaatctat | ttcttaaact | tcttaaattc | tactttata | gttagtcttt | ttttttagttt | 1320 |
| taaaacacca | agaacttagt | ttcgaataaa | cacacataaa | caaacaagct | ttgtagatta | 1380 |
| tg | | | | | | 1382 |

<210> SEQ ID NO 21
<211> LENGTH: 1338
<212> TYPE: DNA
<213> ORGANISM: Artificial Sequence
<220> FEATURE:
<223> OTHER INFORMATION: ADH2/GAPDH promoter with TATA deletion

<400> SEQUENCE: 21

| | | | | | |
|---|---|---|---|---|---|
| ggatccttca | atatgcgcac | atacgctgtt | atgttcaagg | tcccttcgtt | taagaacgaa | 60 |
| agcggtcttc | cttttgaggg | atgtttcaag | ttgttcaaat | ctatcaaatt | tgcaaatccc | 120 |
| cagtctgtat | ctagagcgtt | gaatcggtga | tgcgatttgt | taattaaatt | gatggtgtca | 180 |
| ccattaccag | gtctagatat | accaatggca | aactgagcac | aacaatacca | gtccggatca | 240 |
| actggcacca | tctctcccgt | agtctcatct | aattttttctt | ccggatgagg | ttccagatat | 300 |
| accgcaacac | ctttattatg | gtttccctga | gggaataata | gaatgtccca | ttcgaaatca | 360 |

```
ccaattctaa acctgggcga attgtatttc gggtttgtta actcgttcca gtcaggaatg    420
ttccacgtga agctatcttc cagcaaagtc tccacttctt catcaaattg tgggagaata    480
ctcccaatgc tcttatctat gggacttccg ggaaacacag taccgatact tcccaattcg    540
tcttcagagc tcattgtttg tttgaagaga ctaatcaaag aatcgttttc tcaaaaaaat    600
taatatctta actgatagtt tgatcaaagg ggcaaaacgt aggggcaaac aaacggaaaa    660
atcgtttctc aaattttctg atgccaagaa ctctaaccag tcttatctaa aaattgcctt    720
atgatccgtc tctccggtta cagcctgtgt aactgattaa tcctgccttt ctaatcacca    780
ttctaatgtt ttaattaagg gattttgtct tcattaacgg ctttcgctca taaaaatgtt    840
atgacgtttt gcccgcaggc gggaaaccat ccacttcacg agactgatct cctctgccgg    900
aacaccgggc atctccaact tataagttgg agaaataaga gaatttcaga ttgagagaat    960
gaaaaaaaaa aacccttagt tcataggtcc attctcttag cgcaactaca gagaacaggg   1020
gcacaaacag gcaaaaaacg ggcacaacct caatggagtg atgcaacctg cctggagtaa   1080
atgatgacac aaggcaattg acccacgcat gtatctatct cattttctta caccttctat   1140
taccttctgc tctctctgat ttggaaaaag ctgaaaaaaa aggttgaaac cagttccctg   1200
aaattattcc cctagcattg taattctgta aatctatttc ttaaacttct taaattctac   1260
ttttatagtt agtctttttt ttagttttaa aacaccaaga acttagtttc gaataaacac   1320
acataaacaa acacgcgt                                                 1338
```

<210> SEQ ID NO 22
<211> LENGTH: 2389
<212> TYPE: DNA
<213> ORGANISM: Artificial Sequence
<220> FEATURE:
<223> OTHER INFORMATION: parvovirus B19 VP1 with 1SS

<400> SEQUENCE: 22

```
acgcgtatga tgcctagtta atgaacaaaa caaaatgtct aagaaatccg gaaaatggtg     60
ggaatctgat gataaatttg ctaaggctgt ttaccaacaa tttgttgaat tttacgaaaa    120
ggttactggt actgatttgg aattgattca aattttgaag gatcattaca acatttcttt    180
ggataatcca ttggaaaatc catcttcatt gtttgatttg gttgctagaa ttaagaacaa    240
cttgaagaac tctccagatt tgtattctca tcatttccaa tctcatggtc aattgtctga    300
tcatccacat gctttatctt catcttcatc tcatgctgaa ccaagaggtg aaaatgctgt    360
tttatcttct gaagatttgc ataaaccagg tcaagtttct gttcaattgc caggtactaa    420
ttacgttggt ccaggtaatg aattgcaagc tggtccacca caatctgctg ttgattctgc    480
tgctagaatt catgatttca gatactctca attggctaag ttgggtatta atccatatac    540
tcattggact gttgctgatg aagaattgtt gaagaacatt aagaatgaaa ctggttttca    600
agctcaagtt gttaaagatt acttcacttt gaaaggtgct gctgctccag ttgctcattt    660
tcaaggttct ttgccagaag ttccagctta taacgcttct gaaaaatatc catctatgac    720
atctgttaat tctgctgaag catctactgg tgcaggtgga ggtggttcta attctgttaa    780
atctatgtgg tctgaaggtg ctactttttc tgctaattca gttacttgta ctttctctag    840
acaattcttg attccatatg atccagaaca tcattacaaa gtttttttcac cagctgcttc    900
atcttgtcat aatgcttcag gtaaagaagc taaggtttgt actatttctc caattatggg    960
ttattctact ccttggagat acttggattt taatgctttg aacttgtttt tttctccatt   1020
```

| | | |
|---|---|---|
| ggaatttcaa catttgattg aaaactacgg ttctattgct ccagatgctt tgactgttac | 1080 | |
| tatttctgaa attgctgtta aggatgttac tgataaaaca ggtggtggtg ttcaagttac | 1140 | |
| tgattctact actggtagat tgtgcatgtt ggttgatcat gaatacaaat acccatacgt | 1200 | |
| tttgggtcaa ggtcaagata ctttggctcc agaattgcca atttgggttt attttccacc | 1260 | |
| acaatacgct tatttgactg ttggtgatgt taatactcaa ggtatttctg gtgattctaa | 1320 | |
| aaagttggct tctgaagaat ctgctttta cgttttggaa cattcttctt ttcaattgtt | 1380 | |
| gggtactggt ggtactgctt ctatgtctta caaatttcca ccagttccac ctgaaaattt | 1440 | |
| ggaaggttgt tctcaacatt tttacgaaat gtacaatcca ttgtatggtt ctagattggg | 1500 | |
| tgttccagat actttgggtg gtgatccaaa atttagatct ttgactcatg aagatcatgc | 1560 | |
| tattcaacca caaaatttca tgccaggtcc attggttaat tctgtttcta ctaaagaagg | 1620 | |
| tgattcttct aatacaggtg ctggtaaagc attgactggt ttgtctactg gtacttctca | 1680 | |
| aaacactaga atttctttaa gaccaggtcc agtttcacaa ccatatcatc attgggatac | 1740 | |
| tgataagtac gttactggta ttaatgctat ttcacatggt caaactactt atggtaatgc | 1800 | |
| tgaagataaa gaatatcaac aaggtgttgg tagatttcca aacgaaaaag aacaattgaa | 1860 | |
| acaattgcaa ggtttgaata tgcatactta ctttccaaac aaaggtactc aacaatacac | 1920 | |
| tgatcaaatt gaaagaccat tgatggttgg ttctgtttgg aatagaagag ctttgcatta | 1980 | |
| tgaatctcaa ttgtggtcta agattccaaa tttagatgat tctttcaaga ctcaatttgc | 2040 | |
| tgctttgggt ggttggggtt tgcatcaacc tccaccacaa attttcttga agattttgcc | 2100 | |
| acaatctggt ccaattggtg gtattaaatc tatgggtatt actactttgg ttcaatatgc | 2160 | |
| tgttggtatt atgactgtta caatgacttt taagttgggt ccaagaaaag ctacaggtag | 2220 | |
| atggaatcca caaccaggtg tttatccacc acatgctgct ggtcatttgc cttacgtttt | 2280 | |
| gtatgatcca actgctactg atgctaaaca acatcataga catggttatg aaaaacctga | 2340 | |
| agaattgtgg actgctaaat ctagagttca tccattgtaa tgagtcgac | 2389 | |

```
<210> SEQ ID NO 23
<211> LENGTH: 781
<212> TYPE: PRT
<213> ORGANISM: Parvovirus B19
<220> FEATURE:
<223> OTHER INFORMATION: B19 VP1

<400> SEQUENCE: 23
```

Met Ser Lys Lys Ser Gly Lys Trp Trp Glu Ser Asp Asp Lys Phe Ala
1               5                   10                  15

Lys Ala Val Tyr Gln Gln Phe Val Glu Phe Tyr Glu Lys Val Thr Gly
                20                  25                  30

Thr Asp Leu Glu Leu Ile Gln Ile Leu Lys Asp His Tyr Asn Ile Ser
            35                  40                  45

Leu Asp Asn Pro Leu Glu Asn Pro Ser Ser Leu Phe Asp Leu Val Ala
        50                  55                  60

Arg Ile Lys Asn Asn Leu Lys Asn Ser Pro Asp Leu Tyr Ser His His
65                  70                  75                  80

Phe Gln Ser His Gly Gln Leu Ser Asp His Pro His Ala Leu Ser Ser
                85                  90                  95

Ser Ser Ser His Ala Glu Pro Arg Gly Glu Asn Ala Val Leu Ser Ser
                100                 105                 110

Glu Asp Leu His Lys Pro Gly Gln Val Ser Val Gln Leu Pro Gly Thr
            115                 120                 125

```
Asn Tyr Val Gly Pro Gly Asn Glu Leu Gln Ala Gly Pro Pro Gln Ser
        130                 135                 140

Ala Val Asp Ser Ala Ala Arg Ile His Asp Phe Arg Tyr Ser Gln Leu
145                 150                 155                 160

Ala Lys Leu Gly Ile Asn Pro Tyr Thr His Trp Thr Val Ala Asp Glu
                165                 170                 175

Glu Leu Leu Lys Asn Ile Lys Asn Glu Thr Gly Phe Gln Ala Gln Val
            180                 185                 190

Val Lys Asp Tyr Phe Thr Leu Lys Gly Ala Ala Ala Pro Val Ala His
        195                 200                 205

Phe Gln Gly Ser Leu Pro Glu Val Pro Ala Tyr Asn Ala Ser Glu Lys
210                 215                 220

Tyr Pro Ser Met Thr Ser Val Asn Ser Ala Glu Ala Ser Thr Gly Ala
225                 230                 235                 240

Gly Gly Gly Gly Ser Asn Ser Val Lys Ser Met Trp Ser Glu Gly Ala
                245                 250                 255

Thr Phe Ser Ala Asn Ser Val Thr Cys Thr Phe Ser Arg Gln Phe Leu
            260                 265                 270

Ile Pro Tyr Asp Pro Glu His His Tyr Lys Val Phe Ser Pro Ala Ala
        275                 280                 285

Ser Ser Cys His Asn Ala Ser Gly Lys Glu Ala Lys Val Cys Thr Ile
290                 295                 300

Ser Pro Ile Met Gly Tyr Ser Thr Pro Trp Arg Tyr Leu Asp Phe Asn
305                 310                 315                 320

Ala Leu Asn Leu Phe Phe Ser Pro Leu Glu Phe Gln His Leu Ile Glu
                325                 330                 335

Asn Tyr Gly Ser Ile Ala Pro Asp Ala Leu Thr Val Thr Ile Ser Glu
            340                 345                 350

Ile Ala Val Lys Asp Val Thr Asp Lys Thr Gly Gly Gly Val Gln Val
        355                 360                 365

Thr Asp Ser Thr Thr Gly Arg Leu Cys Met Leu Val Asp His Glu Tyr
370                 375                 380

Lys Tyr Pro Tyr Val Leu Gly Gln Gly Gln Asp Thr Leu Ala Pro Glu
385                 390                 395                 400

Leu Pro Ile Trp Val Tyr Phe Pro Pro Gln Tyr Ala Tyr Leu Thr Val
                405                 410                 415

Gly Asp Val Asn Thr Gln Gly Ile Ser Gly Asp Ser Lys Lys Leu Ala
            420                 425                 430

Ser Glu Glu Ser Ala Phe Tyr Val Leu Glu His Ser Ser Phe Gln Leu
        435                 440                 445

Leu Gly Thr Gly Gly Thr Ala Ser Met Ser Tyr Lys Phe Pro Pro Val
450                 455                 460

Pro Pro Glu Asn Leu Glu Gly Cys Ser Gln His Phe Tyr Glu Met Tyr
465                 470                 475                 480

Asn Pro Leu Tyr Gly Ser Arg Leu Gly Val Pro Asp Thr Leu Gly Gly
                485                 490                 495

Asp Pro Lys Phe Arg Ser Leu Thr His Glu Asp His Ala Ile Gln Pro
            500                 505                 510

Gln Asn Phe Met Pro Gly Pro Leu Val Asn Ser Val Ser Thr Lys Glu
        515                 520                 525

Gly Asp Ser Ser Asn Thr Gly Ala Gly Lys Ala Leu Thr Gly Leu Ser
530                 535                 540
```

```
Thr Gly Thr Ser Gln Asn Thr Arg Ile Ser Leu Arg Pro Gly Pro Val
545                 550                 555                 560

Ser Gln Pro Tyr His His Trp Asp Thr Asp Lys Tyr Val Thr Gly Ile
            565                 570                 575

Asn Ala Ile Ser His Gly Gln Thr Thr Tyr Gly Asn Ala Glu Asp Lys
        580                 585                 590

Glu Tyr Gln Gln Gly Val Gly Arg Phe Pro Asn Glu Lys Glu Gln Leu
    595                 600                 605

Lys Gln Leu Gln Gly Leu Asn Met His Thr Tyr Phe Pro Asn Lys Gly
610                 615                 620

Thr Gln Gln Tyr Thr Asp Gln Ile Glu Arg Pro Leu Met Val Gly Ser
625                 630                 635                 640

Val Trp Asn Arg Arg Ala Leu His Tyr Glu Ser Gln Leu Trp Ser Lys
            645                 650                 655

Ile Pro Asn Leu Asp Asp Ser Phe Lys Thr Gln Phe Ala Ala Leu Gly
        660                 665                 670

Gly Trp Gly Leu His Gln Pro Pro Gln Ile Phe Leu Lys Ile Leu
    675                 680                 685

Pro Gln Ser Gly Pro Ile Gly Gly Ile Lys Ser Met Gly Ile Thr Thr
690                 695                 700

Leu Val Gln Tyr Ala Val Gly Ile Met Thr Val Thr Met Thr Phe Lys
705                 710                 715                 720

Leu Gly Pro Arg Lys Ala Thr Gly Arg Trp Asn Pro Gln Pro Gly Val
            725                 730                 735

Tyr Pro Pro His Ala Ala Gly His Leu Pro Tyr Val Leu Tyr Asp Pro
        740                 745                 750

Thr Ala Thr Asp Ala Lys Gln His Arg His Gly Tyr Glu Lys Pro
    755                 760                 765

Glu Glu Leu Trp Thr Ala Lys Ser Arg Val His Pro Leu
770                 775                 780

<210> SEQ ID NO 24
<211> LENGTH: 554
<212> TYPE: PRT
<213> ORGANISM: Parvovirus B19
<220> FEATURE:
<223> OTHER INFORMATION: B19 VP2

<400> SEQUENCE: 24

Met Thr Ser Val Asn Ser Ala Glu Ala Ser Thr Gly Ala Gly Gly Gly
1               5                   10                  15

Gly Ser Asn Ser Val Lys Ser Met Trp Ser Glu Gly Ala Thr Phe Ser
            20                  25                  30

Ala Asn Ser Val Thr Cys Thr Phe Ser Arg Gln Phe Leu Ile Pro Tyr
        35                  40                  45

Asp Pro Glu His His Tyr Lys Val Phe Ser Pro Ala Ala Ser Ser Cys
    50                  55                  60

His Asn Ala Ser Gly Lys Glu Ala Lys Val Cys Thr Ile Ser Pro Ile
65                  70                  75                  80

Met Gly Tyr Ser Thr Pro Trp Arg Tyr Leu Asp Phe Asn Ala Leu Asn
            85                  90                  95

Leu Phe Phe Ser Pro Leu Glu Phe Gln His Leu Ile Glu Asn Tyr Gly
        100                 105                 110

Ser Ile Ala Pro Asp Ala Leu Thr Val Thr Ile Ser Glu Ile Ala Val
    115                 120                 125
```

-continued

```
Lys Asp Val Thr Asp Lys Thr Gly Gly Val Gln Val Thr Asp Ser
            130                 135                 140
Thr Thr Gly Arg Leu Cys Met Leu Val Asp His Glu Tyr Lys Tyr Pro
145                 150                 155                 160
Tyr Val Leu Gly Gln Gly Gln Asp Thr Leu Ala Pro Glu Leu Pro Ile
                165                 170                 175
Trp Val Tyr Phe Pro Pro Gln Tyr Ala Tyr Leu Thr Val Gly Asp Val
            180                 185                 190
Asn Thr Gln Gly Ile Ser Gly Asp Ser Lys Lys Leu Ala Ser Glu Glu
                195                 200                 205
Ser Ala Phe Tyr Val Leu Glu His Ser Ser Phe Gln Leu Leu Gly Thr
210                 215                 220
Gly Gly Thr Ala Ser Met Ser Tyr Lys Phe Pro Pro Val Pro Pro Glu
225                 230                 235                 240
Asn Leu Glu Gly Cys Ser Gln His Phe Tyr Glu Met Tyr Asn Pro Leu
                245                 250                 255
Tyr Gly Ser Arg Leu Gly Val Pro Asp Thr Leu Gly Gly Asp Pro Lys
            260                 265                 270
Phe Arg Ser Leu Thr His Glu Asp His Ala Ile Gln Pro Gln Asn Phe
            275                 280                 285
Met Pro Gly Pro Leu Val Asn Ser Val Ser Thr Lys Glu Gly Asp Ser
            290                 295                 300
Ser Asn Thr Gly Ala Gly Lys Ala Leu Thr Gly Leu Ser Thr Gly Thr
305                 310                 315                 320
Ser Gln Asn Thr Arg Ile Ser Leu Arg Pro Gly Pro Val Ser Gln Pro
                325                 330                 335
Tyr His His Trp Asp Thr Asp Lys Tyr Val Thr Gly Ile Asn Ala Ile
            340                 345                 350
Ser His Gly Gln Thr Thr Tyr Gly Asn Ala Glu Asp Lys Glu Tyr Gln
            355                 360                 365
Gln Gly Val Gly Arg Phe Pro Asn Glu Lys Glu Gln Leu Lys Gln Leu
            370                 375                 380
Gln Gly Leu Asn Met His Thr Tyr Phe Pro Asn Lys Gly Thr Gln Gln
385                 390                 395                 400
Tyr Thr Asp Gln Ile Glu Arg Pro Leu Met Val Gly Ser Val Trp Asn
                405                 410                 415
Arg Arg Ala Leu His Tyr Glu Ser Gln Leu Trp Ser Lys Ile Pro Asn
            420                 425                 430
Leu Asp Asp Ser Phe Lys Thr Gln Phe Ala Ala Leu Gly Gly Trp Gly
            435                 440                 445
Leu His Gln Pro Pro Gln Ile Phe Leu Lys Ile Leu Pro Gln Ser
450                 455                 460
Gly Pro Ile Gly Gly Ile Lys Ser Met Gly Ile Thr Thr Leu Val Gln
465                 470                 475                 480
Tyr Ala Val Gly Ile Met Thr Val Thr Met Thr Phe Lys Leu Gly Pro
                485                 490                 495
Arg Lys Ala Thr Gly Arg Trp Asn Pro Gln Pro Gly Val Tyr Pro Pro
            500                 505                 510
His Ala Ala Gly His Leu Pro Tyr Val Leu Tyr Asp Pro Thr Ala Thr
            515                 520                 525
```

-continued

```
Asp Ala Lys Gln His His Arg His Gly Tyr Glu Lys Pro Glu Glu Leu
    530                 535                 540

Trp Thr Ala Lys Ser Arg Val His Pro Leu
545                 550
```